(12) United States Patent
Taylor et al.

(10) Patent No.: US 7,381,708 B2
(45) Date of Patent: Jun. 3, 2008

(54) SUPPRESSION OF EIF5A1 EXPRESSION BY THE USE OF ANTISENSE OLIGONUCLEOTIDES FOR THE PREVENTION OF RETINAL CELL DEATH IN THE GLAUCOMATOUS EYE

(75) Inventors: Catherine Taylor, Waterloo (CA); Dominic Cliché, Kitchener (CA); Elizabeth Margaret Heikkila, Waterloo (CA); Diane Michelle Senchyna, Waterloo (CA); John Gerard Flanagan, Waterloo (CA); John E. Thompson, Waterloo (CA)

(73) Assignee: Sensco Technologies, Inc., New Brunswick, NJ (US)

( * ) Notice: Subject to any disclaimer, the term of this patent is extended or adjusted under 35 U.S.C. 154(b) by 667 days.

(21) Appl. No.: 10/383,614

(22) Filed: Mar. 10, 2003

(65) Prior Publication Data
US 2003/0225022 A1   Dec. 4, 2003

Related U.S. Application Data

(63) Continuation-in-part of application No. 10/277,969, filed on Oct. 23, 2002, now Pat. No. 7,217,517, which is a continuation-in-part of application No. 10/200,148, filed on Jul. 23, 2002, which is a continuation-in-part of application No. 10/141,647, filed on May 7, 2002, now Pat. No. 7,166,467, which is a continuation-in-part of application No. 09/909,796, filed on Jul. 23, 2001, now Pat. No. 6,867,237.

(60) Provisional application No. 60/451,677, filed on May 5, 2003.

(51) Int. Cl.
*A01N 43/04* (2006.01)
*C12Q 1/68* (2006.01)
*C12P 19/34* (2006.01)
*C07H 21/02* (2006.01)
*C07H 21/04* (2006.01)

(52) U.S. Cl. .................. 514/44; 435/6; 435/91.1; 435/91.31; 435/455; 536/23.1; 536/24.5

(58) Field of Classification Search .................. 514/44; 435/6, 325, 375, 91.1, 91.31, 455, 458; 536/23.1, 536/24.5
See application file for complete search history.

(56) References Cited

U.S. PATENT DOCUMENTS

2003/0225022 A1   12/2003   Taylor et al.

FOREIGN PATENT DOCUMENTS

| WO | 94/15596 A1 | 7/1994 |
| WO | WO 96/25492 | 8/1996 |
| WO | 96/41639 A1 | 12/1996 |
| WO | WO 99/01551 | 1/1999 |
| WO | 01/02592 A3 | 1/2001 |
| WO | WO 01/10906 | 2/2001 |
| WO | WO 03/010286 | 2/2003 |
| WO | WO 03/095613 | 11/2003 |
| WO | 2004/078940 A2 | 9/2004 |
| WO | 2005/007853 A2 | 1/2005 |

OTHER PUBLICATIONS

Braasch, D. A. Biochemistry. Apr. 2002; 41(14): 4503-4510.*
Branch, A. D., Trends Biochem Sci. Feb. 1998;23(2):45-50.*
Opalinska and Gewirtz Nature Reviews, 2002. 1:503-514.*
Jen et al. (Stem Cells 2000, vol. 18, p. 307-319).*
Tamm, I. et al. The Lancet. 2001, Aug. 358: 489-497.*
Jin, Bao-Feng et al., "Proteomic analysis of ubiquitin-proteasome effects: insight into the future of eukaryotic initiation factor 5A," ONCOGENE, Jul. 31, 2003, pp. 4819-4830, vol. 22, No. 31, Nature Publishing Group, XP-002388453, ISSN: 0950-9232.
Annexes to Form PCT/ISA/206, Invitation to Pay Additional Fees, Communication Relating to the Results of the Partial International Search, PCT/US2005/044266, Aug. 11, 2006, comprised of the Annex first, continuation and 4th of 5 extra sheets and the Patent Family Annex, European Patent Office, International Searching Authority, Rijswijk, NL.
Tome M E et al: "Excess putrescine accumulation inhibits the formation of modified eukaryotic initiation factor 5A (eIF-5A) and induces apoptosis", Biochemical Journal, Portland Press, London, GB, vol. 328, pp. 847-854, 1997, ISSN: 0264-6021.
Database EMBL (Online) Dec. 14, 1999, "uo59b11.y1 NCI_CGAP_Mam1 Mus musculus cDNA clone, Image: 2646813 5' similar to gb:M23419 Initiation Factor 5A (Human);, mRNA sequence", retrieved from EBI accession No. EM_PRO:AW229460.
Bevec Dorian et al: "Molecular characterization of a cDNA encoding functional human deoxyhypusine synthase and chromosomal mapping of the corresponding gene locus", FEBS Letters, vol. 378, No. 2, 1996, pp. 195-198, ISSN: 0014-5793.
Database EMBL (Online) Dec. 11, 1995, "Human deoxyhypusine synthase mRNA, complete cds." retrieved from EBI accession No. EM_HUM:U40579.
Wolff Edith C et al: "Deoxyhypusine synthase from rat testis: Purification and characterization", Journal of Biological Chemistry, vol. 270, No. 15, 1995, pp. 8660-8666, ISSN: 0021-9258.

(Continued)

*Primary Examiner*—Jane Zara
(74) *Attorney, Agent, or Firm*—Womble Carlyle Sandridge & Rice, PLLC

(57) ABSTRACT

The present invention provides methods for preventing retinal ganglion cell death in the glaucomatous eye and methods for suppressing apoptosis-specific eIF5A1 expression through the use of antisense oligonucleotides targeted to human apoptosis-specific eIF5A1.

7 Claims, 69 Drawing Sheets

OTHER PUBLICATIONS

Joe Young Ae et al: "Cloning and expression of human deoxyhypusine synthase cDNA: Structure-function studies with recombinant enzyme and mutant proteins", Journal of Biological Chemistry, vol. 270, No. 38, 1995, pp. 22386-22392, ISSN: 0021-9258.

Database EMBL (Online) Jul. 7, 2000, "hv36b09.x1 NCI_CGAP_Lu24 Homo sapiens cDNA clone, Image:3175481 3' similar to SW:DHYS_Human P49366 Deoxyhypusine Synthase ;, mRNA sequence." retrieved from EBI accession No. EM_EST:BE218247.

Caraglia et al., "The role of eukaryotic initiation factor 5A in the contori of cell proliferation and apoptosis," Amino Acids, (2001) 20: pp. 91-104.

Chen, et al., "RNA interference analysis of the function of hypusine-containing eukaryotic initiation factor 5A in C. elegans", FASEB Journal, Mar. 20, 2002, vol. 16, No. 4; Annual Meeting of the Professional Research Scientists on Experimental Biology; New Orleans, LA, USA, Apr. 20-24, 2002, XP008033807.

Hayashizaki et al., "Analysis of the Mouse Transcriptome Based on Functional Annotation of 60,770 Full-Length cDNAs," Nature, United Kingdom, vol. 420, No. 6915, pp. 563-573, ISSN: 0028-0836, XP002965277, Dec. 5, 2002.

* cited by examiner

```
TCGAAGACCGGTAAGCACGGCCATGCCAAGGTCCATCTGGTTGGTATTGATATTTTTACTGGGAAGAAATAT
 S  K  T  G  K  H  G  H  A  K  V  H  L  V  G  I  D  I  F  T  G  K  K  Y
GAAGATATCTGCCCGTCGACTCATAACATGGATGTCCCCAACATCAAAAGGAATGATTTCCAGCTGATTGGC
 E  D  I  C  P  S  T  H  N  M  D  V  P  N  I  K  R  N  D  F  Q  L  I  G
ATCCAGGATGGGTACCTATCCCTGCTCCAGGACAGTGGGGAGGTACGAGAGGACCTTCGTCTGCCTGAGGGA
 I  Q  D  G  Y  L  S  L  L  Q  D  S  G  E  V  R  E  D  L  R  L  P  E  G
GACCTTGGCAAGGAGATTGAGCAGAAGTATGACTGTGGAGAAGAGATCCTGATCACAGTGCTGTCCGCCATG
 D  L  G  K  E  I  E  Q  K  Y  D  C  G  E  E  I  L  I  T  V  L  S  A  M
ACAGAGGAGGCAGCTGTTGCAATCAAGGCCATGGCAAAATAACTGGCTTCCAGGGTGGCGGTGGTGGCAGCA
 T  E  E  A  A  V  A  I  K  A  M  A  K
GTGATCCATGAGCCTACAGAGGCCCCTCCCCCAGCTCTGGCTGGGCCCTTGGCTGGACTCCTATCCAATTTA
TTTGACGTTTTATTTTGGTTTTCCTCACCCCTTCAAACTGTCGGGGAGACCCTGCCCTTCACCTAGCTCCCT
TGGCCAGGCATGAGGGAGCCATGGCCTTGGTGAAGCTACCTGCCTCTTCTCTCGCAGCCCTGATGGGGGAAA
GGGAGTGGGTACTGCCTGTGGTTTAGGTTCCCCTCTCCCTTTTTCTTTTTAATTCAATTTGGAATCAGAAAG
CTGTGGATTCTGGCAAATGGTCTTGTGTCCTTTATCCCACTCAAACCCATCTGGTCCCCTGTTCTCCATAGT
CCTTCACCCCCAAGCACCACTGACAGACTGGGGACCAGCCCCCTTCCCTGCCTGTGTCTCTTCCCAAACCCC
TCTATAGGGGTGACAAGAAGAGGAGGGGGGAGGGGACACGATCCCTCCTCAGGCATCTGGGAAGGCCTTGC
CCCCATGGGCTTTACCCTTTCCTGTGGGCTTTCTCCCTGACACATTTGTTAAAAATCAAACCTGAATAAAAC
TACAAGTTTAATATGAAAAAAAAAAAAAAAAAAAAAA
(972 NT, 109 aa)
```

FIG.1

```
CAGGTCTAGAGTTGGAATCGAAGCCTCTTAAAATGGCAGATGATTTGGACTTCGAGACAGGAGATGCAGGGG
                                 M  A  D  D  L  D  F  E  T  G  D  A  G
CCTCAGCCACCTTCCCAATGCAGTGCTCAGCATTACGTAAGAATGGTTTTGTGGTGCTCAAGGGCCGGCCAT
 A  S  A  T  F  P  M  Q  C  S  A  L  R  K  N  G  F  V  V  L  K  G  R  P
GTAAGATCGTCGAGATGTCTACTTCGAAGACTGGCAAGCATGGCCATGCCAAGGTCCATCTGGTTGGTATTG
 C  K  I  V  E  M  S  T  S  K  T  G  K  H  G  H  A  K  V  H  L  V  G  I
ATATTTTTACTGGGAAGAAATATGAAGATATCTGCCCGTCGACTCATAACATGGATGTCCCCAACATCAAAA
 D  I  F  T  G  K  K  Y  E  D  I  C  P  S  T  H  N  M  D  V  P  N  I  K
GGAATGATTTCCAGCTGATTGGCATCCAGGATGGGTACCTATCCCTGCTCCAGGACAGTGGGGAGGTACGAG
 R  N  D  F  Q  L  I  G  I  Q  D  G  Y  L  S  L  L  Q  D  S  G  E  V  R
AGGACCTTCGTCTGCCTGAGGGAGACCTTGGCAAGGAGATTGAGCAGAAGTATGACTGTGGAGAAGAGATCC
 E  D  L  R  L  P  E  G  D  L  G  K  E  I  E  Q  K  Y  D  C  G  E  E  I
TGATCACAGTGCTGTCCGCCATGACAGAGGAGGCAGCTGTTGCAATCAAGGCTCGAG
 L  I  T  V  L  S  A  M  T  E  E  A  A  V  A  I  K  A
```

```
CAGGTCTAGAGTTGGAATCGAAGCCTCTTAAAATGGCAGATGATTTGGACTTCGAGACAGGAGATGCAGGGG
                                M  A  D  D  L  D  F  E  T  G  D  A  G      13
CCTCAGCCACCTTCCCAATGCAGTGCTCAGCATTACGTAAGAATGGTTTTGTGGTGCTCAAGGGCCGGCCAT   144
 A  S  A  T  F  P  M  Q  C  S  A  L  R  K  N  G  F  V  V  L  K  G  R  P
GTAAGATCGTCGAGATGTCTACTTCGAAGACTGGCAAGCATGGCCATGCCAAGGTCCATCTGGTTGGTATTG
 C  K  I  V  E  M  S  T  S  K  T  G  K  H  G  H  A  K  V  H  L  V  G  I    61
ATATTTTTACTGGGAAGAAATATGAAGATATCTGCCCGTCGACTCATAACATGGATGTCCCCAACATCAAAA   288
 D  I  F  T  G  K  K  Y  E  D  I  C  P  S  T  H  N  M  D  V  P  N  I  K
GGAATGATTTCCAGCTGATTGGCATCCAGGATGGGTACCTATCCCTGCTCCAGGACAGTGGGGAGGTACGAG
 R  N  D  F  Q  L  I  G  I  Q  D  G  Y  L  S  L  L  Q  D  S  G  E  V  R    109
AGGACCTTCGTCTGCCTGAGGGAGACCTTGGCAAGGAGATTGAGCAGAAGTATGACTGTGGAGAAGAGATCC   432
 E  D  L  R  L  P  E  G  D  L  G  K  E  I  E  Q  K  Y  D  C  G  E  E  I
TGATCACAGTGCTGTCCGCCATGACAGAGGAGGCAGCTGTTGCAATCAAGGCCATGGCAAAATAACTGGCTT
 L  I  T  V  L  S  A  M  T  E  E  A  A  V  A  I  K  A  M  A  K  *          154
CCAGGGTGGCGGTGGTGGCAGCAGTGATCCATGAGCCTACAGAGGCCCCTCCCCCAGCTCTGGCTGGGCCCT   576
TGGCTGGACTCCTATCCAATTTATTTGACGTTTTATTTTGGTTTTCCTCACCCCTTCAAACTGTCGGGGAGA
CCCTGCCCTTCACCTAGCTCCCTTGGCCAGGCATGAGGGAGCCATGGCCTTGGTGAAGCTACCTGCCTCTTC   720
TCTCGCAGCCCTGATGGGGGAAAGGGAGTGGGTACTGCCTGTGGTTTAGGTTCCCCTCTCCCTTTTTCTTTT
TAATTCAATTTGGAATCAGAAAGCTGTGGATTCTGGCAAATGGTCTTGTGTCCTTTATCCCACTCAAACCCA   864
TCTGGTCCCCTGTTCTCCATAGTCCTTCACCCCCAAGCACCACTGACAGACTGGGGACCAGCCCCCTTCCCT
GCCTGTGTCTCTTCCCAAACCCCTCTATAGGGGTGACAAGAAGAGGAGGGGGGAGGGGACACGATCCCTCC  1008
TCAGGCATCTGGGAAGGCCTTGCCCCCATGGGCTTTACCCTTTCCTGTGGGCTTTCTCCCTGACACATTTGT
TAAAAATCAAACCTGAATAAAACTACAAGTTTAATATGAAAAAAAAAAAAAAAAAAAAA               1139
```

```
GCTGTGTATTATTGGGCCCATAAGAACCACATACCTGTGCTGAGTCCTGCACTCACAGACGGCTCACTGGGT
  A  V  Y  Y  W  A  H  K  N  H  I  P  V  L  S  P  A  L  T  D  G  S  L  G
GACATGATCTTTTTTCCATTCCTATAAAAACCCAGGCTTGGTCCTGGACATCGTTGAAGACCTGCGGCTCATC
  D  M  I  F  F  H  S  Y  K  N  P  G  L  V  L  D  I  V  E  D  L  R  L  I
AACATGCAGGCCATTTTCGCCAAGCGCACTGGGATGATCATCCTGGGTGGAGGCGTGGTCAAGCACCACATC
  N  M  Q  A  I  F  A  K  R  T  G  M  I  I  L  G  G  G  V  V  K  H  H  I
GCCAATGCTAACCTCATGCGGAATGGAGCTGACTACGCTGTTTATATCAACACAGCCCAGGAGTTTGATGGC
  A  N  A  N  L  M  R  N  G  A  D  Y  A  V  Y  I  N  T  A  Q  E  F  D  G
TCAGACTCAGGAGCCCGGCCAGATGAGGCTGTCTCCTGGGGCAAGATCCGGATGGATGCACAGCCAGTAAAG
  S  D  S  G  A  R  P  D  E  A  V  S  W  G  K  I  R  M  D  A  Q  P  V  K
GTCTATGCTGATGCATCTCTGGTTTTCCCCTTGCTGGTGGCTGAGACATTCGCCCAAAAGGCAGATGCCTTC
  V  Y  A  D  A  S  L  V  F  P  L  L  V  A  E  T  F  A  Q  K  A  D  A  F
AGAGCTGAGAAGAATGAGGACTGAGCAGATGGGTAAAGACGGAGGCTTCTGCCACACCTTTATTTATTATTT
  R  A  E  K  N  E  D
GCATACCAACCCCTCCTGGGCCCTCTCCTTGGTCAGCAGCATCTTGAGAATAAATGGCCTTTTTGTTGGTTT
CTGTAAAAAAAGGACTTTAAAAAAAAAAAA (606 NT, 151 aa)
```

FIG.4 rat vs. human(BC000751 or NM_001970) 96.5% identity (coding)

```
            10        20        30        40        50        60
rat  ATGGCAGATGATTTGGACTTCGAGACAGGAGATGCAGGGGCCTCAGCCACCTTCCCAATG
     :::::::::: :::::::::::::::::::::::::::::::::::::::::::::::::
human ATGGCAGATGACTTGGACTTCGAGACAGGAGATGCAGGGGCCTCAGCCACCTTCCCAATG
            10        20        30        40        50        60

70        80        90       100       110       120
rat  CAGTGCTCAGCATTACGTAAGAATGGTTTTGTGGTGCTCAAGGGCCGGCCATGTAAGATC
     :::::::::::::::::::::::::::: :::::::::::::: ::::::::::::::::
human CAGTGCTCAGCATTACGTAAGAATGGCTTTGTGGTGCTCAAAGGCCGGCCATGTAAGATC
            70        80        90       100       110       120

130       140       150       160       170       180
rat  GTCGAGATGTCTACTTCGAAGACTGGCAAGCATGGCCATGCCAAGGTCCATCTGGTTGGT
     :::::::::::::::::::::::::::::::::: ::::: :::::::::::::::::::
human GTCGAGATGTCTACTTCGAAGACTGGCAAGCACGGCCACGCCAAGGTCCATCTGGTTGGT
           130       140       150       160       170       180

190       200       210       220       230       240
rat  ATTGATATTTTTACTGGGAAGAAATATGAAGATATCTGCCCGTCGACTCATAACATGGAT
     ::::: :: ::::::::::::::::::::::::::::::::: :::::::: ::::::::
human ATTGACATCTTTACTGGGAAGAAATATGAAGATATCTGCCCGTCAACTCATAATATGGAT
           190       200       210       220       230       240

250       260       270       280       290       300
rat  GTCCCCAACATCAAAAGGAATGATTTCCAGCTGATTGGCATCCAGGATGGGTACCTATCC
     :::::::::::::::::::::::: :::::::::::::::::::::::::::::::::: 
human GTCCCCAACATCAAAAGGAATGACTTCCAGCTGATTGGCATCCAGGATGGGTACCTATCA
           250       260       270       280       290       300

310       320       330       340       350       360
rat  CTGCTCCAGGACAGTGGGGAGGTACGAGAGGACCTTCGTCTGCCTGAGGGAGACCTTGGC
     :::::::::::::: ::::::::::::::::::::::::::: :::::::::::::::::
human CTGCTCCAGGACAGCGGGGAGGTACGAGAGGACCTTCGTCTCCCTGAGGGAGACCTTGGC
           310       320       330       340       350       360

370       380       390       400       410       420
rat  AAGGAGATTGAGCAGAAGTATGACTGTGGAGAAGAGATCCTGATCACAGTGCTGTCCGCC
     :::::::::::::::::::: :::::::::::::::::::::::::: ::::::::: ::
human AAGGAGATTGAGCAGAAGTACGACTGTGGAGAAGAGATCCTGATCACGGTGCTGTCTGCC
           370       380       390       400       410       420

430       440       450       460
rat  ATGACAGAGGAGGCAGCTGTTGCAATCAAGGCCATGGCAAAA
     :::::::::::::::::::::::::::::::::::::::::
human ATGACAGAGGAGGCAGCTGTTGCAATCAAGGCCATGGCAAAA
           430       440       450       460
```

FIG.5 rat vs. human(NM_020390) 72.5% identity (coding)

```
              10         20         30         40         50         60
rat    ATGGCAGATGATTTGGACTTCGAGACAGGAGATGCAGGGGCCTCAGCCACCTTCCCAATG
       :::::::::: ::  :   :  :: :::    ::  ::::::  :::::  ::    :::  :  :::  :::
human  ATGGCAGACGAAATTGATTTCACTACTGGAGATGCCGGGGCTTCCAGCACTTACCCTATG
              10         20         30         40         50         60

70         80         90        100        110        120
rat    CAGTGCTCAGCATTACGTAAGAATGGTTTTGTGGTGCTCAAGGGCCGGCCATGTAAGATC
       ::::::::: ::  :: :: :: :: :: ::  :::::::::::: :: :: ::::::  :: ::
human  CAGTGCTCGGCCTTGCGCAAAAACGGCTTCGTGGTGCTCAAAGGACGACCATGCAAAATA
              70         80         90        100        110        120

130        140        150        160        170        180
rat    GTCGAGATGTCTACTTCGAAGACTGGCAAGCATGGCCATGCCAAGGTCCATCTGGTTGGT
       ::  ::::::::: ::::: ::  ::  :::::::::  ::::::::::::: :: ::: :::::
human  GTGGAGATGTCAACTTCCAAAAACTGGAAAGCATGGTCATGCCAAGGTTCACCTTGTTGGA
             130        140        150        160        170        180

190        200        210        220        230        240
rat    ATTGATATTTTTACTGGGAAGAAATATGAAGATATCTGCCCGTCGACTCATAACATGGAT
       :::::::::::: ::  ::  ::::::::::: :::::::: ::: ::  ::  ::  ::::: :::::::::
human  ATTGATATTTTTCACGGGCAAAAAATATGAAGATATTTGTCCTTCTACTCACAACATGGAT
             190        200        210        220        230        240

250        260        270        280        290        300
rat    GTCCCCAACATCAAAAGGAATGATTTCCAGCTGATTGGCATCCAGGATGGGTACCTATCC
       ::  ::  :: :: :: :: :: :::::::: :: :::::  :::::   ::::: :::::  :::
human  GTTCCAAATATTAAGAGAAATGATTATCAACTGATATGCATTCAAGATGGTTACCTTTCC
             250        260        270        280        290        300

310        320        330        340        350        360
rat    CTGCTCCAGGACAGTGGGGAGGTACGAGAGGACCTTCGTCTGCCTGAGGGAGACCTTGGC
       :::::  :: : :::  :: :: ::::: :::  :::::  ::::: :: :: :: :::
human  CTGCTGACAGAAACTGGTGAAGTTCGTGAGGATCTTAAACTGCCAGAAGGTGAACTAGGC
             310        320        330        340        350        360

370        380        390        400        410        420
rat    AAGGAGATTGAGCAGAAGTATGACTGTGGAGAAGAGATCCTGATCACAGTGCTGTCCGCC
       :: :: :: :::   ::  ::   ::  :: :::::  :  : : :  : :   ::
human  AAAGAAATAGAGGGAAAATACAATGCAGGTGAAGATGTACAGGTGTCTGTCATGTGTGCA
             370        380        390        400        410        420

430        440        450        460
rat    ATGACAGAGGAGGCAGCTGTTGCAATCAAGGCCATGGCAAAA
       ::::  ::  ::  :::::::: ::  ::  ::  ::   :::::
human  ATGAGTGAAGAATATGCTGTAGCCATAAAACCCT--GCAAAT
             430        440        450        460
```

FIG.6 rat vs. mouse (BC003889) 98.3% identity (coding)

```
              10        20        30        40        50        60
rat    ATGGCAGATGATTTGGACTTCGAGACAGGAGATGCAGGGGCCTCAGCCACCTTCCCAATG
       ::::::::::::::::::::::::::::::::::::::::::::::::::::::::::::
mouse  ATGGCAGATGATTTGGACTTCGAGACAGGAGATGCAGGGGCCTCAGCCACCTTCCCAATG
              10        20        30        40        50        60

70        80        90       100       110       120
rat    CAGTGCTCAGCATTACGTAAGAATGGTTTTGTGGTGCTCAAGGGCCGGCCATGTAAGATC
       ::::::::::::::::::::::::::::::::::::::: ::::::::::::::::::::
mouse  CAGTGCTCAGCATTACGTAAGAATGGTTTTGTGGTGCTCAAAGGCCGGCCATGTAAGATC
              70        80        90       100       110       120

130       140       150       160       170       180
rat    GTCGAGATGTCTACTTCGAAGACTGGCAAGCATGGCCATGCCAAGGTCCATCTGGTTGGT
       :::::::::::::::::::::::::::::::::::::::::::::::::::::::::::
mouse  GTCGAGATGTCTACTTCGAAGACTGGCAAGCATGGCCATGCCAAGGTCCATCTGGTTGGC
             130       140       150       160       170       180

190       200       210       220       230       240
rat    ATTGATATTTTTACTGGGAAGAAATATGAAGATATCTGCCCGTCGACTCATAACATGGAT
       ::::: :::::::::::::::::::::::::::::::::::::::::::::::: :::::
mouse  ATTGACATTTTTACTGGGAAGAAATATGAAGATATCTGCCCGTCGACTCATAATATGGAT
             190       200       210       220       230       240

250       260       270       280       290       300
rat    GTCCCCAACATCAAAAGGAATGATTTCCAGCTGATTGGCATCCAGGATGGGTACCTATCC
       :::::::::::::::: ::::::: ::::::::::::::::::::::::::::::::::
mouse  GTCCCCAACATCAAACGGAATGACTTCCAGCTGATTGGCATCCAGGATGGGTACCTATCC
             250       260       270       280       290       300

310       320       330       340       350       360
rat    CTGCTCCAGGACAGTGGGGAGGTACGAGAGGACCTTCGTCTGCCTGAGGGAGACCTTGGC
       :::::::::::::::::::::::::::::::::::::::::::::::: :::::::::::
mouse  CTGCTCCAGGACAGTGGGGAGGTACGAGAGGACCTTCGTCTGCCTGAAGGAGACCTTGGC
             310       320       330       340       350       360

370       380       390       400       410       420
rat    AAGGAGATTGAGCAGAAGTATGACTGTGGAGAAGAGATCCTGATCACAGTGCTGTCCGCC
       ::::::::::::::::::::::::::::::::::::::::::::::::::::::::: :::
mouse  AAGGAGATTGAGCAGAAGTATGACTGTGGAGAAGAGATCCTGATCACAGTGCTGTCTGCC
             370       380       390       400       410       420

430       440       450       460
rat    ATGACAGAGGAGGCAGCTGTTGCAATCAAGGCCATGGCAAAA
       ::::::::::::::::::::::::::::::::::::::::::
mouse  ATGACAGAGGAGGCAGCTGTTGCAATCAAGGCCATGGCAAAA
             430       440       450       460
```

FIG.7 rat vs. human(BC000751 or NM_001970) 100.0% identity

```
             10        20        30        40        50        60
rat    MADDLDFETGDAGASATFPMQCSALRKNGFVVLKGRPCKIVEMSTSKTGKHGHAKVHLVG
       ::::::::::::::::::::::::::::::::::::::::::::::::::::::::::::
human  MADDLDFETGDAGASATFPMQCSALRKNGFVVLKGRPCKIVEMSTSKTGKHGHAKVHLVG
             10        20        30        40        50        60

70        80        90       100       110       120
rat    IDIFTGKKYEDICPSTHNMDVPNIKRNDFQLIGIQDGYLSLLQDSGEVREDLRLPEGDLG
       ::::::::::::::::::::::::::::::::::::::::::::::::::::::::::::
human  IDIFTGKKYEDICPSTHNMDVPNIKRNDFQLIGIQDGYLSLLQDSGEVREDLRLPEGDLG
             70        80        90       100       110       120

130       140       150
rat    KEIEQKYDCGEEILITVLSAMTEEAAVAIKAMAK
       :::::::::::::::::::::::::::::::::
human  KEIEQKYDCGEEILITVLSAMTEEAAVAIKAMAK
            130       140       150
```

FIG.8 rat vs. human(NM_020390) 82.5% identity

```
              10        20        30        40        50        60
rat    MADDLDFETGDAGASATFPMQCSALRKNGFVVLKGRPCKIVEMSTSKTGKHGHAKVHLVG
       :::..::  :::::::::.:::::::::::::::::::::::::::::::::::::::::
human  MADEIDFTTGDAGASSTYPMQCSALRKNGFVVLKGRPCKIVEMSTSKTGKHGHAKVHLVG
              10        20        30        40        50        60

70        80        90       100       110       120
rat    IDIFTGKKYEDICPSTHNMDVPNIKRNDFQLIGIQDGYLSLLQDSGEVREDLRLPEGDLG
       :::::::::::::::::::::::::::::.::: :::::::::  ..:::::::.::::::
human  IDIFTGKKYEDICPSTHNMDVPNIKRNDYQLICIQDGYLSLLTETGEVREDLKLPEGELG
              70        80        90       100       110       120

130       140       150
rat    KEIEQKYDCGEEILITVLSAMTEEAAVAIKAMAK
       ::::  ::. :::.  ::::..:: :::::    :
human  KEIEGKYNAGEDVQVSVMCAMSEEYAVAIKP-CK
              130       140       150
```

FIG.9 rat vs. mouse (BC003889)100.0% identity

```
           10        20        30        40        50        60
rat    MADDLDFETGDAGASATFPMQCSALRKNGFVVLKGRPCKIVEMSTSKTGKHGHAKVHLVG
       ::::::::::::::::::::::::::::::::::::::::::::::::::::::::::::
mouse  MADDLDFETGDAGASATFPMQCSALRKNGFVVLKGRPCKIVEMSTSKTGKHGHAKVHLVG
           10        20        30        40        50        60

70        80        90       100       110       120
rat    IDIFTGKKYEDICPSTHNMDVPNIKRNDFQLIGIQDGYLSLLQDSGEVREDLRLPEGDLG
       ::::::::::::::::::::::::::::::::::::::::::::::::::::::::::::
mouse  IDIFTGKKYEDICPSTHNMDVPNIKRNDFQLIGIQDGYLSLLQDSGEVREDLRLPEGDLG
           70        80        90       100       110       120

130       140       150
rat    KEIEQKYDCGEEILITVLSAMTEEAAVAIKAMAK
       :::::::::::::::::::::::::::::::::
mouse  KEIEQKYDCGEEILITVLSAMTEEAAVAIKAMAK
          130       140       150
```

FIG. 10 rat vs. human (BC000333) 87.4% identity (coding)

```
              10        20        30        40        50        60
rat   GCTGTGTATTATTGGGCCCATAAGAACCACATACCTGTGCTGAGTCCTGCACTCACAGAC
       : ::::::::: :::::::::: ::::::::::::: ::::::: : ::::: ::::: ::::::
human TCCGTGTATTACTGGGCCCAGAAGAACCACATCCCTGTGTTTAGTCCCGCACTTACAGAC
              10        20        30        40        50        60

70        80        90       100       110       120
rat   GGCTCACTGGGTGACATGATCTTTTTCCATTCCTATAAAAACCCAGGCTTGGTCCTGGAC
      ::::: :::::: ::::::::::::: ::::::::::::::: :: ::::: ::: ::::::::::::
human GGCTCGCTGGGCGACATGATCTTCTTCCATTCCTACAAGAACCCGGGCCTGGTCCTGGAC
              70        80        90       100       110       120

130       140       150       160       170       180
rat   ATCGTTGAAGACCTGCGGCTCATCAACATGCAGGCCATTTTCGCCAAGCGCACTGGGATG
      :::::::: :::::: ::::::::::::::: :::::::::: :::::: :: :::::: ::::::::::::
human ATCGTTGAGGACCTGAGGCTCATCAACACACAGGCCATCTTTGCCAAGTGCACTGGGATG
             130       140       150       160       170       180

190       200       210       220       230       240
rat   ATCATCCTGGGTGGAGGCGTGGTCAAGCACCACATCGCCAATGCTAACCTCATGCGGAAT
      :::::: :::::: :: ::::::::::::::::::::::::: :::::::: :::::: ::::::::::::
human ATCATTCTGGGCGGGGGCGTGGTCAAGCACCACATTGCCAATGCCAACCTCATGCGGAAC
             190       200       210       220       230       240

250       260       270       280       290       300
rat   GGAGCTGACTACGCTGTTTATATCAACACAGCCCAGGAGTTTGATGGCTCAGACTCAGGA
      :: :: :::::::::::::::: :::::::::::::::::::::::::::::::::: :::::::::
human GGGGCCGACTACGCTGTTTACATCAACACAGCCCAGGAGTTTGATGGCTCTGACTCAGGT
             250       260       270       280       290       300

310       320       330       340       350       360
rat   GCCCGGCCAGATGAGGCTGTCTCCTGGGGCAAGATCCGGATGGATGCACAGCCAGTAAAG
      :::::: :::::: :: ::::::::::::::::::::::::::::::: :::::::::::::: :: ::::
human GCCCGACCAGACGAGGCTGTCTCCTGGGGCAAGATCCGGGTGGATGCACAGCCCGTCAAG
             310       320       330       340       350       360

370       380       390       400       410       420
rat   GTCTATGCTGATGCATCTCTGGTTTTCCCCTTGCTGGTGGCTGAGACATTCGCCCAAAAG
      :::::::::::: :: :: ::::: :::::: :::: ::::::::::: :: :: :::::: :::
human GTCTATGCTGACGCCTCCCTGGTCTTCCCCCTGCTTGTGGCTGAAACCTTTGCCCAGAAG
             370       380       390       400       410       420

430       440       450
rat   GCAGATGCCTTCAGAGCTGAGAAGAATGAGGAC
      :::::::::: :::::::::: :::::::
human ATGGATGCCTTCATGCATGAGAAGAACGAGGAC
             430       440       450
```

FIG.11

3' rat eIF-5A 
Ethidium Bromide-Stained RNA
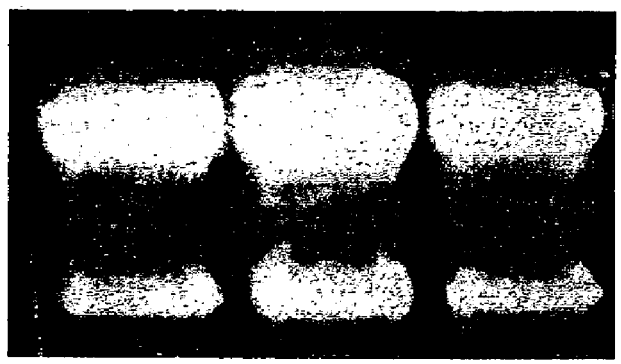
FIG.22

Hoescht Staining of Transformed
COS-7 Cells Deprived of Serum
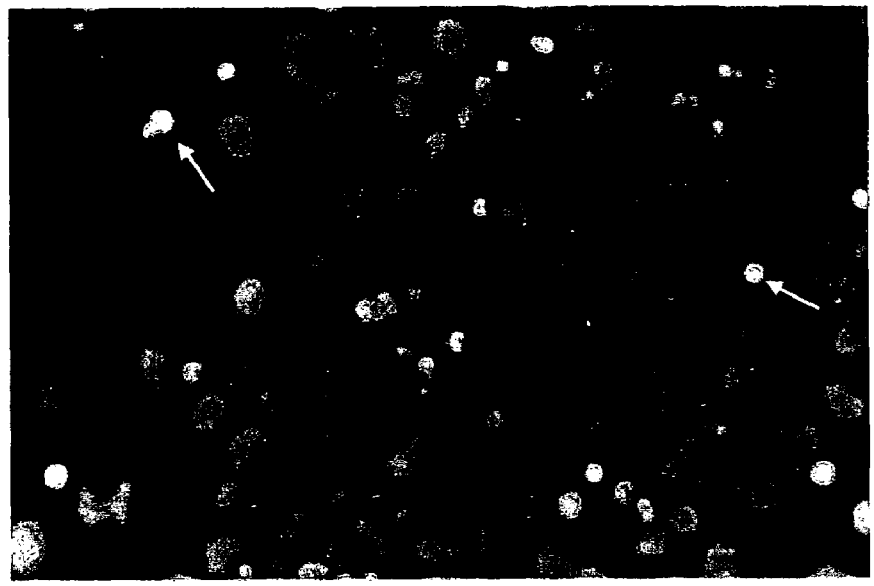
Mock Transformed
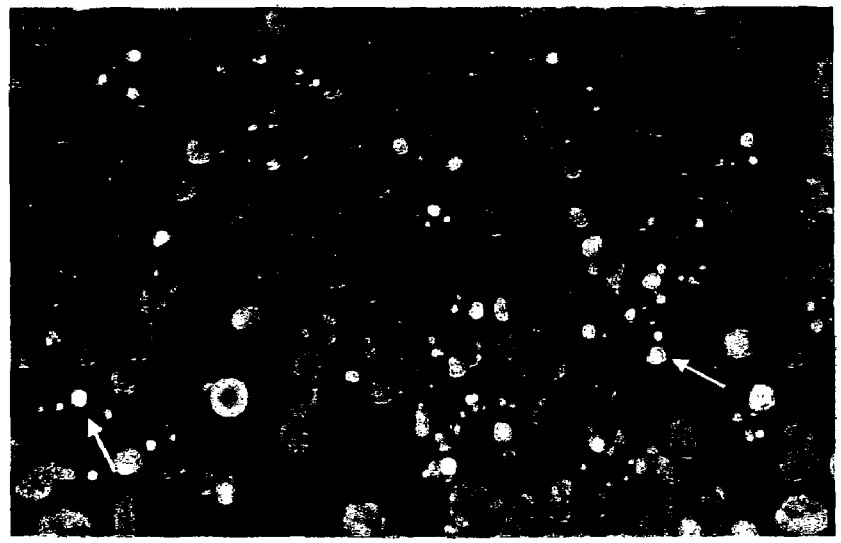
pHm6-Sense rat F5A
FIG. 27

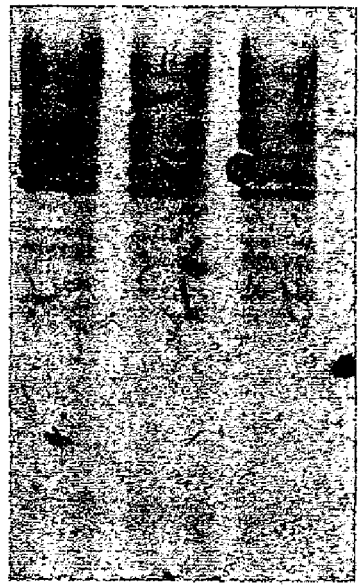 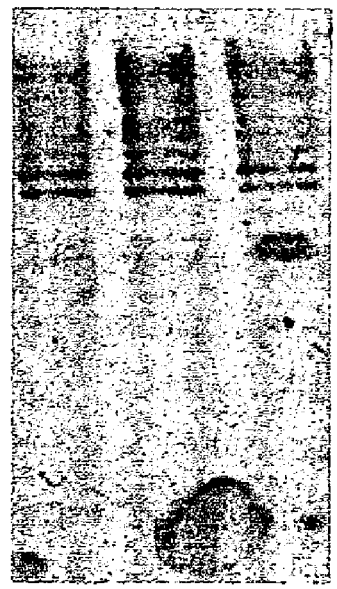
FIG.37A

Sequence and Alignment of human eIF5A2 isolated from RKO cells with sequence of human eIF5A2 in Genbank (ACCESSION XM_113401)

```
XM_113401  MADEIDFTTG DAGASSTYPM QCSALRKNGF VVLKGRPCKI VEMSTSKTGK
      PCR  MADEIDFTTG DAGASSTYPM QCSALRKNGF VVLKGRPCKI VEMSTSKTGK
Consensus  MADEIDFTTG DAGASSTYPM QCSALRKNGF VVLKGRPCKI VEMSTSKTGK 51                                                 100
XM_113401  HGHAKVHLVG IDIFTGKKYE DICPSTHNMD VPNIKRNDYQ LICIQDGYLS
      PCR  HGHAKVHLVG IDIFTGKKYE DICPSTHNMD VPNIKRNDYQ LICIQDGCLS
Consensus  HGHAKVHLVG IDIFTGKKYE DICPSTHNMD VPNIKRNDYQ LICIQDGcLS 101                                                150
XM_113401  LLTETGEVRE DLKLPEGELG KEIEGKYNAG EDVQVSVMCA MSEEYAVAIK
      PCR  LLTETGEVRE DLKLPEGELG KEIEGKYNAG EDVQVSVMCA MSEEYAVAIK
Consensus  LLTETGEVRE DLKLPEGELG KEIEGKYNAG EDVQVSVMCA MSEEYAVAIK 151
XM_113401  PCK
      PCR  PCK
Consensus  PCK
```

FIG.38

| TRANSFECTED PLASMID | PERCENT APOPTOSIS |
|---|---|
| UNTRANSFECTED | 21.2% |
| pHM6-Lac Z | 21.7% |
| pHM6-eIF5A1 | 60.7% (80%)* |
| pHM6-eIF5A2 | 20.5% |
| pHM6-TRUNCATED eIF5A1 | 24.1% |

*CORRECTED FOR BACKGROUND APOPTOSIS IN UNTRANSFECTED CELLS AND FOR TRANSFECTION EFFICIENCY

| PATIENT | Ds | IF5a1 pg/ng rRNA | IF5a2 pg/ng rRNA | 0.5 | 2.0 | IL-18 pg/ng rRNA | IL-1b pg/ng rRNA |
|---|---|---|---|---|---|---|---|
| 207 | CABG | 9.0 | 2.4 | 3.8 | 0.3 | 10.1 | 7.2 |
| 21 | CABG | 123.2 | 81.6 | 1.5 | 0.7 | 405.9 | 41.5 |
| 23 | CABG | 0.1 | 0.0 | 11.0 | 0.1 | 0.0 | 0.0 |
| 26 | CABG | | | | | | |
| 28 | CABG | 200.4 | 294.6 | 0.7 | 1.5 | 894.1 | 49.7 |
| 30 | CABG | 279.4 | 921.2 | 0.3 | 3.3 | 669.8 | 71.0 |
| 33 | CABG | 260.1 | 723.9 | 0.4 | 2.8 | 545.6 | 105.1 |
| 34 | CABG | 263.4 | 309.3 | 0.9 | 1.2 | 520.0 | 19.9 |
| 65 | CABG | 82.9 | 43.1 | 1.9 | 0.5 | 98.2 | 20.2 |
| 139 | CABG | 23.9 | 7.0 | 3.4 | 0.3 | 22.7 | 57.3 |
| 140 | CABG | 0.9 | 0.0 | #DIV/0! | 0.0 | 0.1 | 0.0 |
| 143 | CABG | 137.7 | 169.5 | 0.8 | 1.2 | 338.7 | 77.9 |

FIG.50A

| PATIENT | Ds | IF5a1 pg/ng rRNA | IF5a2 pg/ng rRNA | 0.5 | 2.0 | IL-18 pg/ng rRNA | IL-1b pg/ng rRNA |
|---|---|---|---|---|---|---|---|
| 206 | VALVE | 44.4 | 33.1 | 1.3 | 0.7 | 50.0 | 67.2 |
| 330 | VALVE | | | | | | |
| 331 | VALVE | 11.3 | 0.2 | 68.9 | 0.0 | 0.1 | 0.0 |
| 332 | VALVE | 224.5 | 194.0 | 1.2 | 0.9 | 510.5 | 37.2 |
| 289 | VALVE | 286.3 | 674.1 | 0.4 | 2.4 | 888.0 | 167.5 |
| 290 | VALVE | 303.9 | 540.4 | 0.6 | 1.8 | 545.8 | 20.6 |
| 291 | VALVE | 148.1 | 311.8 | 0.5 | 2.1 | 229.2 | 31.1 |
| 292 | VALVE | 221.1 | 367.2 | 0.6 | 1.7 | 280.8 | 55.0 |
| 312 | VALVE | 361.1 | 262.5 | 1.4 | 0.7 | 198.0 | 44.2 |
| 314 | VALVE | 6.5 | 1.6 | 4.0 | 0.2 | 74.7 | 18.6 |
| 318 | VALVE | 83.3 | 48.5 | 1.7 | 0.6 | 69.3 | 13.3 |
| 324 | VALVE | 485.9 | 414.1 | 1.2 | 0.9 | 584.9 | 98.6 |

FIG.50B

| Expt # | Age | Sex | DM | Unstable engine | Operation | Misc.... | date RNA |
|---|---|---|---|---|---|---|---|
| 19 | 61 | M | Y | N | CABG | Metoprolol, Lovastatin, NTG | |
| 20 | 72 | M | Y | N | CABG | Metoprolol, Lipitor | |
| 21 | 55 | M | N | N | CABG | CYA, Imuran, Prednisone, Lasix, INS, Metoprolol | 7/30/02 |
| 23 | 71 | M | N | N | CABG | Imipramine, Isordil, NTG, Metoprolol | 7/30/02 |
| 24 | 75 | M | Y | Y | CABG | Lisinopril, Glipizide, Metoprolol, NTG | |
| ? | 61 | M | N | N | CABG | Lisinopril, digoxin, Lasix, NTG, ASA | 7/30/02 |
| 26 | 57 | M | N | N | CABG | Atenolol, Norvasc, HCTZ, NTG, ASA | 9-Aug |
| 28 | 48 | F | N | N | CABG | Atenolol, INS, Lisinopril | |
| 29 | 64 | M | N | N | MVR | Lasix, Lisinopril | 9-Aug |
| 30 | 76 | M | N | N | CABG | | |
| 31 | 65 | M | Y | N | CABG | | 9-Aug |
| 33 | 54 | M | N | N | CABG | Simvastatin, metoprolol | 9-Aug |
| 34 | 63 | M | N | N | CABG | Lisinopril, Felodipoine, NTG | |
| 35 | 74 | M | Y | N | CABG | Amlodipine, Glyburide, Prazosin | |
| 36 | 62 | M | Y | N | CABG | Simvastatin, INS, Felodipine, Spironolactone, Metoprtolol, Lisinopril, | |
| 37 | 63 | M | N | N | CABG | Famotidine, Atenolol, Fosinopril, Procardia, Zocor, NTG | |
| 38 | 63 | M | N | N | CABG | A-fib, Dig, Atenolol, Zocor, Coumadin | |

CONT'D FROM FIG.51

| | | | | | | |
|---|---|---|---|---|---|---|
| 39 | 77 | M | N | N | CABG | Coumadin, Cozar, Zocor, HCTZ, Cortioarone |
| 41 | 74 | F | N | Y | AVR/CABG | Dig, Zestril |
| 42 | 59 | M | Y | N | CABG | Statin, Atenolol, Glucotrol, Lisinopril |
| 44 | 64 | M | Y | N | CABG | Atenolol, NTG, Lisinopril, Simvastatin, Verapamil |
| 47 | 64 | M | N | N | CABG | NTG, Lisinopril, Synthroid, simvastatin |
| 48 | 56 | M | Y | Y | CABG | NTG, Metoprolol, Glipizide, Simvastatin |
| 52 | 70 | M | Y | N | CABG | Fosinopril, Glipizide, HCTZ, Felodipine, Metoprolol, |
| 53 | 55 | M | Y | N | CABG | Lasix, Lisinopril, Glyburide, Nifedipine |
| 54 | 48 | M | Y | Y | CABG | Lisinopril, Metoprolol, NTG, Lasiz, ASA<Simvastatin, INS |
| 55 | 67 | M | N | N | CABG | ASA, prednisone, Atenolol |
| 56 | 71 | M | Y | N | CABG | ASA, Simvastatin, Atenolol, Lisinopril, NTG |
| 58 | 70 | M | Y | N | CABG | Coumadin, Synthroid, NTG, Glyburide |
| 59 | 55 | M | Y | N | CABG | Lisinopril, NTG, Glyburide, metoprolol, Simvastatin |
| 60 | 55 | M | Y | N | CABG | Metformin, Glyburide, ASA, Atenolol, Lisinopril, Simvastatin |
| 61 | 68 | M | Y | N | CABG | Atenolol, Lasix, Fosinopril, Simvastatin, Glyburide |
| 61 | 68 | M | Y | N | CABG | Atenolol, Lasix, Fosinopril, Simvastatin, Glyburide |
| 62 | 76 | M | N | N | CABG | Gemfibrozil, ASA, Metoprolol, NTG |
| 64 | 61 | M | N | N | MVR | |

CONT'D FROM FIG.51A

| | | | | | | | |
|---|---|---|---|---|---|---|---|
| 64 | 61 | M | N | N | MVR | | 12-Sep |
| 65 | 72 | M | N | Y | CABG | ASA, NTG | |
| 67 | 69 | M | Y | N | CABG | | |
| 138 | 75 | M | Y | N | CABG | Lisinopril, Simvastatin, metoprolol, Metformin, glyburide | |
| 139 | 71 | M | N | Y | CABG | Metoprolol, Dyazide, Lipitor, Cardura, Lotrol | 12-Sep |
| 140 | 86 | M | N | Y | CABG | Metoprolol, Amlodipine, NTG, Heparin | 12-Sep |
| 141 | 65 | M | Y | N | CABG | ASA, Clopidogril, Glipizide, Lisinopril, INS, | |
| 142 | 75 | F | Y | N | CABG | Glyburide, Atenolol, Lisinopril, Maxide, Methyldopa | |
| 141 | 44 | M | N | N | CABG | Atenolol, Lisinopril, Simvastatin, | 12-Sep |
| 144 | 57 | M | N | N | AVR | Allopurinol, Colchicine, Minoxidil, Atenol, Lasix, Prednisone, Simvastatin | |
| 145 | 67 | M | N | N | CABG | Lipitor, Metoprolol, NTG, ASA | |
| 146 | 42 | M | N | N | CABG | Atenolol, Norvasc, NTG | |
| 147 | 71 | M | N | N | MVR | Dig, Verapamil, Coumadin | |
| 148 | 71 | F | N | N | CABG | | |
| 150 | 70 | M | Y | N | CABG | Felodipine, HCTZ, INS, Synthroid, Losartin, Simvastatin, Atenolol, | |
| 151 | 78 | F | Y | N | CABG | Dig, NTG, Lisinopril, Cavedolol, INS | |

CONT'D FROM FIG.51B

| | | | | | |
|---|---|---|---|---|---|
| 152 | 50 | M | N | N | CABG | Lisinopril, NTG, Lasix, Metoprolol |
| 153 | 48 | M | N | N | AVR | |
| 154 | 67 | M | N | N | CABG | Simvastatin, Lisinopril, Atenolol |
| 155 | 59 | M | N | N | CABG | Lisinopril, ASA, Metoprolol, Simvastatin |
| 156 | 62 | M | Y | N | CABG | NTG, Glyburide, Atorvastatin, Atenolol |
| 161 | 56 | M | Y | N | MVR | INS, Metoprolol, NTG, Simvastatin, Lisinopril |
| 162 | 23 | F | N | N | MVR | |
| 163 | 72 | M | N | N | AVR | Simvastatin, Felodipine, Cimetidine |
| 164 | 65 | F | N | N | MVR | Multi valve Dz. A-fib Metoprolol, DIG, Coumadin |
| 166 | 57 | F | N | N | MVR | Synthroid |
| 173 | 60 | M | N | N | AVR | |
| 177 | 66 | F | N | N | MVR | Severe MR, Lisinopril |
| 184 | 46 | M | N | N | MVR | Vasotec |
| 185 | 75 | M | Y | Y | CABG,MVR | Tropolol, Capoten, Plavix, Synthroid |
| 201 | 50 | M | N | N | AVR | Lasix, Incubated in ICE prior to D/C |

CONT'D FROM FIG.51C

| | | | | | |
|---|---|---|---|---|---|
| 206 | 58 | M | N | AVR | |
| 207 | 68 | M | N | CABG | Vasotec |
| 211 | 51 | M | N | AVR | Simvastatin, Atenolol |
| 289 | 45 | M | N | AVR | EF<20% |
| 290 | 77 | M | N | MVR | |
| 291 | 55 | F | N | AVR | |
| 292 | 39 | M | N | MVR | |
| 310 | 67 | F | N | AVR/MVY | |
| 312 | 72 | F | N | AVR | |
| 314 | 75 | F | N | AVR | |
| 318 | 62 | M | N | AVR | |
| 329 | 70 | M | N | AVR | |
| 330 | 67 | M | N | AVR | |
| 331 | 58 | M | N | AVR | |
| 339 | 69 | M | N | AVR | |

| |
|---|
| |
| |
| |
| 9-Aug |
| 9-Aug |
| 9-Aug |
| 9-Aug |
| |
| 12-Sep |
| 12-Sep |
| 12-Sep |
| 12-Sep |
| 7/30/02 |
| 7/30/02 |
| 7/30/02 |

FIG.51D

Position of Antisense Oligonucleotides Within Nucleotide Sequence of Human eIF5A1 (ACCESSION NM_001970; Translation Start and Stop in Bold)

*Antisense eIF5A1 # 1 (SEQ ID NO:25)* - binds to *GACTTGGACTTCGAGAGACAGG*
Antisense eIF5A1 # 2 (SEQ ID NO:26) - binds to GCACGGCCACGCCAAGGTC
Antisense eIF5A1 # 3 (SEQ ID NO:27) - binds to GGACAGCGGGGAGGTACGAG GGCACGAGGGCGGGCGGGGTAGAGGCGGGGCGGGGGCTCGGAGGGCAGGGTTGGGCTCGCGGGCGAGGGAGGCGGGACGGGGTCGAGTCAGTGCGTTCG
CGCGAGTTGGAATCGAAGCCTCTTAAATGGCAGAT*GACTTGGACTTCGAGAGACAGG*AGATGCAGGGGCCTCAGCGACTACTTCGAAGACTGTCTACTTCGAGATCGAGTGCTCAGCATTACGTA
AGAATGGCTTTGTGGTGCTCAAAGGCCGGCCATGTAAGATCGTGCCGTCAACTCATGATGAGATCGTCCCCAACATCAAAAGGAATGACTTCCAGCTGATTGGCATCCAGGATGGG
CATCTTTACTGGGAAGAATATGAAGATATCTGCCCGTCAACTCATGATGTCCCAACATCAAAAGGAATGACTTCCAGCTGATTGGCATCCAGGATGGG
TACCTATCACTGCTCCAGGACAGCGGGGAGGTACGAGAGAGCCTCCATGCCATGAGAGGCAGCTGTTGCAATCAAGGCCATGGCAAAATAACTGGCTCCTACACAATTATTTGACGTTTATTTTGGTTTTTCCCCA
TCCTGATCACGGTGCTGTCTGCCATGACAGAGGAGCCTGGCCTGCTGGCCTGCTAAGCTTCCTCACCTAGCCCCTTCACCAGGTGCTGCCCAAAATCATCTGGAAGCATTAAATGCTGAAAGGGTGGAT
CGTGAACCTGCAGAGGCCCCCCTCGTCGGGAGCCCTGCTGGGGTGGGTGTGAGTCTTTTAGTCTTTTTTTTTTTTTTCCCTTTGCCCATAGCCCCTTTACCCTGCCCCCCTTGCCCCCTGTTGCCCATAGCCCCTTTACCCTGAGCACCACACCCAACAGACTGGGGACCAGCCC
CCCCTCAATCTGTCGGGAGCCCTGCTGGGGTGGGTGTGAGTCTTTTTTTTTTTTTTCCCTTTGCCCATAGCCCCTTTACCCTGAGCACCACACCCAACAGACTGGGGACCAGCCC
TACAGCCCTGGTGGGGAGAAGGGGTCCTTGTGCCTCCCCAAACCCTTTAGATGGGGAGGAAGAGAGGAAGAGGGACCTGCCCCTCCTCAGGCATCTGGGAGGGCCCTGCCCC
TCTGGCAAATGTCCTTGTGCCTCCCCAAACCCTTTAGATGGGGAGGAAGAGAGGAAGAGGGACCTGCCCCTCCTCAGGCATCTGGGAGGGCCCTGCCCC
ATGGGCTTTACCCTTCCCGCGGGCTCTCTCCCCGACACATTTGTTAAAATCAAACCTGAATAAAACTACACAAGTTTAATATGAAAAAAAAAAAAAAAAAAAAA
AAAAAAAAAAAAAAAAAAAAAAAAAAAA

FIG.58

Nucleotide Alignment of Human eIF5A1 (ACC. NM_001970) and Human eIF5A2 (ACC. NM_020390)

```
eIF5a1    1  ATGGCAGATG ACTTGGACTT CGAGACAGGA GATGCAGGGG CCTCAGCCAC
eIF5a2    1  ATGGCAGACG AAATTGATTT CACTACTGGA GATGCCGGGG CTTCCAGCAC eIF5a1   51  CTTCCCAATG CAGTGCTCAG CATTACGtAA GAATGGCTTT GTGGTGCTCA
eIF5a2   51  TTACCCTATG CAGTGCTCGG CCTTGCGCAA AAACGGCTTC GTGGTGCTCA eIF5a1  101  AAGGCCGGCC ATGtAAGATC GTCGAGATGT CTACTTCGAA GACTGGCAAG
eIF5a2  101  AAGGACGACC ATGcAAAATA GTGGAGATGT CAACTTCCAA AACTGGAAAG eIF5a1  151  CAcGGCCACG CCAAGGTCCA TCTGGTTGGT ATTGACATCT TtACTGGGAA
eIF5a2  151  CAtGGTCATG CCAAGGTTCA CCTTGTTGGA ATTGATATTT TcACGGGCAA eIF5a1  201  GAAATATGAA GATATCTGCC CGTCAACTCA tAATATGGAT GTCCCCAACA
eIF5a2  201  AAAATATGAA GATATTTGTC CTTCTACTCA CAACATGGAT GTTCCAAATA eIF5a1  251  TCAAAAGGAA TGACTtCCAG CTGATTGGCA TCCAGGATGG GTACCTATCA
eIF5a2  251  TTAAGAGAAA TGATTatCAA CTGATATGCA TTCAAGATGG TTACCTTTCC eIF5a1  301  CTGCTccagG ACAGCGGGGA GGTACGAGAG GACCTTCGTC TcCCTGAGGG
eIF5a2  301  CTGCTgacaG AAACTGGTGA AGTTCGTGAG GATCTTAAAC TgCCAGAAGG eIF5a1  351  AGACCTTGGC AAGGAGATTG AGcagAAGTA CGACTGTGGA GAAGAGATCC
eIF5a2  351  TGAACTAGGC AAAGAAATAG AGggaAAATA CAATGCAGGT GAAGATGTAC eIF5a1  401  TGATCACGGT GCTGTcTGCC ATGACAGAGG AGGCAGCTGT TGCAATCAAG
eIF5a2  401  AGGTGTCTGT CATGtGTGCA ATGAGTGAAG AATATGCTGT AGCCATAAAA eIF5a1  451  GCCatgGCAA AATAa
eIF5a2  451  CCCt--GCAA ATAA-
```

FIG.59A

Amino Acid Alignment of Human eIF5A1 (ACC. NM_001970) and Human eIF5A2 (ACC. NM_020390)

```
eIF5a1        1  MADDLDFETG  DAGASATFPM  QCSALRKNGF  VVLKGwPCKI  VEMSASKTGK
eIF5a2        1  MADEIDFTTG  DAGASSTYPM  QCSALRKNGF  VVLKGrPCKI  VEMSTSKTGK eIF5a1       51  HGHAKVHLVG  IDIFTGKKYE  DICPSTHNMD  VPNIKRNDFQ  LIGIQDGYLS
eIF5a2       51  HGHAKVHLVG  IDIFTGKKYE  DICPSTHNMD  VPNIKRNDYQ  LICIQDGYLS eIF5a1      101  LLQDSGEVPE  DLRLPEGDLG  KEIEQKYDCG  EEILITLLSA  MTEEAAVAIK
eIF5a2      101  LLTETGEVRE  DLKLPEGELG  KEIEGKYNAG  EDVQVSVMCA  MSEEYAVAIK eIF5a1      151  amak
eIF5a2      151  pck-
```

FIG.59B

SEQUENCE LISTING

<160> NUMBER OF SEQ ID NOS: 48

<210> SEQ ID NO 1
<211> LENGTH: 1139
<212> TYPE: DNA
<213> ORGANISM: Rattus sp.
<220> FEATURE:
<221> NAME/KEY: CDS
<222> LOCATION: (33)..(494)

<400> SEQUENCE: 1

```
caggtctaga gttggaatcg aagcctctta aa atg gca gat gat ttg gac ttc          53
                                    Met Ala Asp Asp Leu Asp Phe
                                      1               5 gag aca gga gat gca ggg gcc tca gcc acc ttc cca atg cag tgc tca         101
Glu Thr Gly Asp Ala Gly Ala Ser Ala Thr Phe Pro Met Gln Cys Ser
         10                  15                  20 gca tta cgt aag aat ggt ttt gtg gtg ctc aag ggc cgg cca tgt aag         149
Ala Leu Arg Lys Asn Gly Phe Val Val Leu Lys Gly Arg Pro Cys Lys
     25                  30                  35 atc gtc gag atg tct act tcg aag act ggc aag cat ggc cat gcc aag         197
Ile Val Glu Met Ser Thr Ser Lys Thr Gly Lys His Gly His Ala Lys
 40                  45                  50                  55 gtc cat ctg gtt ggt att gat att ttt act ggg aag aaa tat gaa gat         245
Val His Leu Val Gly Ile Asp Ile Phe Thr Gly Lys Lys Tyr Glu Asp
                 60                  65                  70 atc tgc ccg tcg act cat aac atg gat gtc ccc aac atc aaa agg aat         293
Ile Cys Pro Ser Thr His Asn Met Asp Val Pro Asn Ile Lys Arg Asn
             75                  80                  85 gat ttc cag ctg att ggc atc cag gat ggg tac cta tcc ctg ctc cag         341
Asp Phe Gln Leu Ile Gly Ile Gln Asp Gly Tyr Leu Ser Leu Leu Gln
         90                  95                 100 gac agt ggg gag gta cga gag gac ctt cgt ctg cct gag gga gac ctt         389
Asp Ser Gly Glu Val Arg Glu Asp Leu Arg Leu Pro Glu Gly Asp Leu
    105                 110                 115 ggc aag gag att gag cag aag tat gac tgt gga gaa gag atc ctg atc         437
Gly Lys Glu Ile Glu Gln Lys Tyr Asp Cys Gly Glu Glu Ile Leu Ile
120                 125                 130                 135 aca gtg ctg tcc gcc atg aca gag gag gca gct gtt gca atc aag gcc         485
Thr Val Leu Ser Ala Met Thr Glu Glu Ala Ala Val Ala Ile Lys Ala
                140                 145                 150 atg gca aaa taactggctt ccagggtggc ggtggtggca gcagtgatcc                  534
Met Ala Lys atgagcctac agaggcccct cccccagctc tggctgggcc cttggctgga ctcctatcca       594
atttatttga cgttttattt tggttttcct caccccttca aactgtcggg gagaccctgc       654
ccttcaccta gctcccttgg ccaggcatga gggagccatg ccttggtga agctacctgc        714 ctcttctctc gcagccctga tgggggaaag ggagtgggta ctgcctgtgg tttaggttcc       774
cctctccctt tttcttttta attcaatttg gaatcagaaa gctgtggatt ctggcaaatg       834
gtcttgtgtc ctttatccca ctcaaaccca tctggtcccc tgttctccat agtccttcac       894
ccccaagcac cactgacaga ctggggacca gccccttcc ctgcctgtgt ctcttcccaa        954 accccctctat aggggtgaca agaagaggag gggggaggg gacacgatcc ctcctcaggc      1014
atctgggaag gccttgcccc catgggcttt acccttcct gtgggctttc tccctgacac       1074
atttgttaaa aatcaaacct gaataaaact acaagtttaa tatgaaaaaa aaaaaaaaa       1134 aaaaa                                                                   1139
```

<210> SEQ ID NO 2
<211> LENGTH: 154
<212> TYPE: PRT
<213> ORGANISM: Rattus sp.

<400> SEQUENCE: 2

```
Met Ala Asp Asp Leu Asp Phe Glu Thr Gly Asp Ala Gly Ala Ser Ala
 1               5                  10                  15

Thr Phe Pro Met Gln Cys Ser Ala Leu Arg Lys Asn Gly Phe Val Val
            20                  25                  30

Leu Lys Gly Arg Pro Cys Lys Ile Val Glu Met Ser Thr Ser Lys Thr
        35                  40                  45

Gly Lys His Gly His Ala Lys Val His Leu Val Gly Ile Asp Ile Phe
    50                  55                  60

Thr Gly Lys Lys Tyr Glu Asp Ile Cys Pro Ser Thr His Asn Met Asp
65                  70                  75                  80

Val Pro Asn Ile Lys Arg Asn Asp Phe Gln Leu Ile Gly Ile Gln Asp
                85                  90                  95

Gly Tyr Leu Ser Leu Leu Gln Asp Ser Gly Glu Val Arg Glu Asp Leu
            100                 105                 110

Arg Leu Pro Glu Gly Asp Leu Gly Lys Glu Ile Glu Gln Lys Tyr Asp
        115                 120                 125

Cys Gly Glu Glu Ile Leu Ile Thr Val Leu Ser Ala Met Thr Glu Glu
    130                 135                 140

Ala Ala Val Ala Ile Lys Ala Met Ala Lys
145                 150
```

<210> SEQ ID NO 3
<211> LENGTH: 462
<212> TYPE: DNA
<213> ORGANISM: Homo sapiens

<400> SEQUENCE: 3

```
atggcagatg acttggactt cgagacagga gatgcagggg cctcagccac cttcccaatg    60
cagtgctcag cattacgtaa gaatggcttt gtggtgctca aaggccggcc atgtaagatc   120
gtcgagatgt ctacttcgaa gactggcaag cacggccacg ccaaggtcca tctggttggt   180
attgacatct ttactgggaa gaaatatgaa gatatctgcc cgtcaactca taatatggat   240
gtccccaaca tcaaaaggaa tgacttccag ctgattggca tccaggatgg gtacctatca   300
ctgctccagg acagcgggga ggtacgagag gaccttcgtc tccctgaggg agaccttggc   360
aaggagattg agcagaagta cgactgtgga gaagagatcc tgatcacggt gctgtctgcc   420
atgacagagg aggcagctgt tgcaatcaag gccatggcaa aa                     462
```

<210> SEQ ID NO 4
<211> LENGTH: 462
<212> TYPE: DNA
<213> ORGANISM: Homo sapiens
<220> FEATURE:
<221> NAME/KEY: modified_base
<222> LOCATION: (455)..(456)
<223> OTHER INFORMATION: a, t, c or g

<400> SEQUENCE: 4

```
atggcagacg aaattgattt cactactgga gatgccgggg cttccagcac ttaccctatg    60
cagtgctcgg ccttgcgcaa aaacggcttc gtggtgctca aaggacgacc atgcaaaata   120
```

```
gtggagatgt caacttccaa aactggaaag catggtcatg ccaaggttca ccttgttgga      180
attgatattt tcacgggcaa aaatatgaa gatatttgtc cttctactca caacatggat       240
gttccaaata ttaagagaaa tgattatcaa ctgatatgca ttcaagatgg ttacctttcc      300
ctgctgacag aaactggtga agttcgtgag atcttaaac tgccagaagg tgaactaggc       360
aaagaaatag agggaaaata caatgcaggt gaagatgtac aggtgtctgt catgtgtgca      420
atgagtgaag aatatgctgt agccataaaa ccctnngcaa at                        462

<210> SEQ ID NO 5
<211> LENGTH: 462
<212> TYPE: DNA
<213> ORGANISM: Rattus sp.

<400> SEQUENCE: 5
atggcagatg atttggactt cgagacagga gatgcagggg cctcagccac cttcccaatg      60
cagtgctcag cattacgtaa gaatggtttt gtggtgctca aaggccggcc atgtaagatc     120
gtcgagatgt ctacttcgaa gactggcaag catggccatg ccaaggtcca tctggttggc     180
attgacattt ttactgggaa gaaatatgaa gatatctgcc cgtcgactca taatatggat     240
gtccccaaca tcaaacggaa tgacttccag ctgattggca tccaggatgg gtacctatcc     300
ctgctccagg acagtgggga ggtacgagag gaccttcgtc tgcctgaagg agaccttggc     360
aaggagattg agcagaagta tgactgtgga aagagatcc tgatcacagt gctgtctgcc      420
atgacagagg aggcagctgt tgcaatcaag gccatggcaa aa                        462

<210> SEQ ID NO 6
<211> LENGTH: 606
<212> TYPE: DNA
<213> ORGANISM: Rattus sp.
<220> FEATURE:
<221> NAME/KEY: CDS
<222> LOCATION: (1)..(453)

<400> SEQUENCE: 6 gct gtg tat tat tgg gcc cat aag aac cac ata cct gtg ctg agt cct         48
Ala Val Tyr Tyr Trp Ala His Lys Asn His Ile Pro Val Leu Ser Pro
  1               5                  10                  15 gca ctc aca gac ggc tca ctg ggt gac atg atc ttt ttc cat tcc tat         96
Ala Leu Thr Asp Gly Ser Leu Gly Asp Met Ile Phe Phe His Ser Tyr
             20                  25                  30 aaa aac cca ggc ttg gtc ctg gac atc gtt gaa gac ctg cgg ctc atc        144
Lys Asn Pro Gly Leu Val Leu Asp Ile Val Glu Asp Leu Arg Leu Ile
         35                  40                  45 aac atg cag gcc att ttc gcc aag cgc act ggg atg atc atc ctg ggt        192
Asn Met Gln Ala Ile Phe Ala Lys Arg Thr Gly Met Ile Ile Leu Gly
     50                  55                  60 gga ggc gtg gtc aag cac cac atc gcc aat gct aac ctc atg cgg aat        240
Gly Gly Val Val Lys His His Ile Ala Asn Ala Asn Leu Met Arg Asn
 65                  70                  75                  80 gga gct gac tac gct gtt tat atc aac aca gcc cag gag ttt gat ggc        288
Gly Ala Asp Tyr Ala Val Tyr Ile Asn Thr Ala Gln Glu Phe Asp Gly
                 85                  90                  95 tca gac tca gga gcc cgg cca gat gag gct gtc tcc tgg ggc aag atc        336
Ser Asp Ser Gly Ala Arg Pro Asp Glu Ala Val Ser Trp Gly Lys Ile
            100                 105                 110 cgg atg gat gca cag cca gta aag gtc tat gct gat gca tct ctg gtt        384
Arg Met Asp Ala Gln Pro Val Lys Val Tyr Ala Asp Ala Ser Leu Val
        115                 120                 125
```

```
ttc ccc ttg ctg gtg gct gag aca ttc gcc caa aag gca gat gcc ttc      432
Phe Pro Leu Leu Val Ala Glu Thr Phe Ala Gln Lys Ala Asp Ala Phe
    130                 135                 140 aga gct gag aag aat gag gac tgagcagatg ggtaaagacg gaggcttctg         483
Arg Ala Glu Lys Asn Glu Asp
145                 150 ccacacctttt atttattatt tgcataccaa cccctcctgg gccctctcct tggtcagcag   543
catcttgaga ataaatggcc ttttgttgg tttctgtaaa aaaggactt taaaaaaaaa      603 aaa                                                                  606

<210> SEQ ID NO 7
<211> LENGTH: 151
<212> TYPE: PRT
<213> ORGANISM: Rattus sp.

<400> SEQUENCE: 7

Ala Val Tyr Tyr Trp Ala His Lys Asn His Ile Pro Val Leu Ser Pro
  1               5                  10                  15

Ala Leu Thr Asp Gly Ser Leu Gly Asp Met Ile Phe Phe His Ser Tyr
             20                  25                  30

Lys Asn Pro Gly Leu Val Leu Asp Ile Val Glu Asp Leu Arg Leu Ile
         35                  40                  45

Asn Met Gln Ala Ile Phe Ala Lys Arg Thr Gly Met Ile Ile Leu Gly
     50                  55                  60

Gly Gly Val Val Lys His His Ile Ala Asn Ala Asn Leu Met Arg Asn
 65                  70                  75                  80

Gly Ala Asp Tyr Ala Val Tyr Ile Asn Thr Ala Gln Glu Phe Asp Gly
                 85                  90                  95

Ser Asp Ser Gly Ala Arg Pro Asp Glu Ala Val Ser Trp Gly Lys Ile
            100                 105                 110

Arg Met Asp Ala Gln Pro Val Lys Val Tyr Ala Asp Ala Ser Leu Val
        115                 120                 125

Phe Pro Leu Leu Val Ala Glu Thr Phe Ala Gln Lys Ala Asp Ala Phe
    130                 135                 140

Arg Ala Glu Lys Asn Glu Asp
145                 150

<210> SEQ ID NO 8
<211> LENGTH: 453
<212> TYPE: DNA
<213> ORGANISM: Homo sapiens

<400> SEQUENCE: 8
tccgtgtatt actgggccca gaagaaccac atccctgtgt ttagtcccgc acttacagac    60
ggctcgctgg gcgacatgat cttcttccat tcctacaaga cccgggcct ggtcctggac    120 atcgttgagg acctgaggct catcaacaca caggccatct tgccaagtg cactgggatg    180 atcattctgg gcgggggcgt ggtcaagcac acattgcca atgccaacct catgcggaac    240
ggggccgact acgctgttta catcaacaca gcccaggagt ttgatggctc tgactcaggt    300
gcccgaccag acgaggctgt ctcctggggc aagatccggg tggatgcaca gcccgtcaag    360
gtctatgctg acgcctccct ggtcttcccc ctgcttgtgg ctgaaacctt gcccagaag    420 atggatgcct tcatgcatga agaacgag gac                                   453

<210> SEQ ID NO 9
<211> LENGTH: 20
```

<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (12)
<223> OTHER INFORMATION: a, t, c or g

<400> SEQUENCE: 9
tcsaarachg gnaagcaygg                                              20

<210> SEQ ID NO 10
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
gcgaagcttc catggctcga gttttttttt tttttttttt tt                     42

<210> SEQ ID NO 11
<211> LENGTH: 972
<212> TYPE: DNA
<213> ORGANISM: Rattus sp.
<220> FEATURE:
<221> NAME/KEY: CDS
<222> LOCATION: (1)..(327)

<400> SEQUENCE: 11

| tcg | aag | acc | ggt | aag | cac | ggc | cat | gcc | aag | gtc | cat | ctg | gtt | ggt | att | 48 |
| Ser | Lys | Thr | Gly | Lys | His | Gly | His | Ala | Lys | Val | His | Leu | Val | Gly | Ile | |
| 1 | | | | 5 | | | | | 10 | | | | | 15 | | |

| gat | att | ttt | act | ggg | aag | aaa | tat | gaa | gat | atc | tgc | ccg | tcg | act | cat | 96 |
| Asp | Ile | Phe | Thr | Gly | Lys | Lys | Tyr | Glu | Asp | Ile | Cys | Pro | Ser | Thr | His | |
| | | | 20 | | | | | 25 | | | | | 30 | | | |

| aac | atg | gat | gtc | ccc | aac | atc | aaa | agg | aat | gat | ttc | cag | ctg | att | ggc | 144 |
| Asn | Met | Asp | Val | Pro | Asn | Ile | Lys | Arg | Asn | Asp | Phe | Gln | Leu | Ile | Gly | |
| | | 35 | | | | | 40 | | | | | 45 | | | | |

| atc | cag | gat | ggg | tac | cta | tcc | ctg | ctc | cag | gac | agt | ggg | gag | gta | cga | 192 |
| Ile | Gln | Asp | Gly | Tyr | Leu | Ser | Leu | Leu | Gln | Asp | Ser | Gly | Glu | Val | Arg | |
| 50 | | | | | 55 | | | | | 60 | | | | | | |

| gag | gac | ctt | cgt | ctg | cct | gag | gga | gac | ctt | ggc | aag | gag | att | gag | cag | 240 |
| Glu | Asp | Leu | Arg | Leu | Pro | Glu | Gly | Asp | Leu | Gly | Lys | Glu | Ile | Glu | Gln | |
| 65 | | | | 70 | | | | | 75 | | | | | 80 | | |

| aag | tat | gac | tgt | gga | gaa | gag | atc | ctg | atc | aca | gtg | ctg | tcc | gcc | atg | 288 |
| Lys | Tyr | Asp | Cys | Gly | Glu | Glu | Ile | Leu | Ile | Thr | Val | Leu | Ser | Ala | Met | |
| | | | | 85 | | | | | 90 | | | | | 95 | | |

| aca | gag | gag | gca | gct | gtt | gca | atc | aag | gcc | atg | gca | aaa | taactggctt | | | 337 |
| Thr | Glu | Glu | Ala | Ala | Val | Ala | Ile | Lys | Ala | Met | Ala | Lys | | | | |
| | | | 100 | | | | | 105 | | | | | | | | | ccagggtggc ggtggtggca gcagtgatcc atgagcctac agaggcccct ccccagctc    397
tggctgggcc cttggctgga ctcctatcca atttatttga cgttttattt tggttttcct    457
caccccttca aactgtcggg gagaccctgc ccttcaccta gctcccttgg ccaggcatga    517
gggagccatg gccttggtga agctacctgc ctcttctctc gcagcccctga tgggggaaag    577
ggagtgggta ctgcctgtgg tttaggttcc cctctccctt tttcttttta attcaatttg    637
gaatcagaaa gctgtggatt ctggcaaatg tcttgtgtc cttatccca ctcaaaccca     697
tctggtcccc tgttctccat agtccttcac ccccaagcac cactgacaga ctggggacca    757

-continued

```
gcccccttcc ctgcctgtgt ctcttcccaa acccctctat aggggtgaca agaagaggag    817 gggggggaggg gacacgatcc ctcctcaggc atctgggaag gccttgcccc catgggcttt    877
acccttccct gtgggctttc tcctgacac atttgttaaa aatcaaacct gaataaaact     937
acaagtttaa tatgaaaaaa aaaaaaaaaa aaaaa                               972

<210> SEQ ID NO 12
<211> LENGTH: 109
<212> TYPE: PRT
<213> ORGANISM: Rattus sp.

<400> SEQUENCE: 12

Ser Lys Thr Gly Lys His Gly His Ala Lys Val His Leu Val Gly Ile
  1               5                  10                  15

Asp Ile Phe Thr Gly Lys Lys Tyr Glu Asp Ile Cys Pro Ser Thr His
                 20                  25                  30

Asn Met Asp Val Pro Asn Ile Lys Arg Asn Asp Phe Gln Leu Ile Gly
             35                  40                  45

Ile Gln Asp Gly Tyr Leu Ser Leu Leu Gln Asp Ser Gly Glu Val Arg
         50                  55                  60

Glu Asp Leu Arg Leu Pro Glu Gly Asp Leu Gly Lys Glu Ile Glu Gln
 65                  70                  75                  80

Lys Tyr Asp Cys Gly Glu Glu Ile Leu Ile Thr Val Leu Ser Ala Met
                 85                  90                  95

Thr Glu Glu Ala Ala Val Ala Ile Lys Ala Met Ala Lys
            100                 105

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
caggtctaga gttggaatcg aagc                                            24

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
atatctcgag ccttgattgc aacagctgcc                                      30

<210> SEQ ID NO 15
<211> LENGTH: 489
<212> TYPE: DNA
<213> ORGANISM: Rattus sp.
<220> FEATURE:
<221> NAME/KEY: CDS
<222> LOCATION: (33)..(485)

<400> SEQUENCE: 15
caggtctaga gttggaatcg aagcctctta aa atg gca gat gat ttg gac ttc      53
                                    Met Ala Asp Asp Leu Asp Phe
                                      1               5
```

```
gag aca gga gat gca ggg gcc tca gcc acc ttc cca atg cag tgc tca      101
Glu Thr Gly Asp Ala Gly Ala Ser Ala Thr Phe Pro Met Gln Cys Ser
        10                  15                  20 gca tta cgt aag aat ggt ttt gtg gtg ctc aag ggc cgg cca tgt aag      149
Ala Leu Arg Lys Asn Gly Phe Val Val Leu Lys Gly Arg Pro Cys Lys
    25                  30                  35 atc gtc gag atg tct act tcg aag act ggc aag cat ggc cat gcc aag      197
Ile Val Glu Met Ser Thr Ser Lys Thr Gly Lys His Gly His Ala Lys
40                  45                  50                  55 gtc cat ctg gtt ggt att gat att ttt act ggg aag aaa tat gaa gat      245
Val His Leu Val Gly Ile Asp Ile Phe Thr Gly Lys Lys Tyr Glu Asp
                60                  65                  70 atc tgc ccg tcg act cat aac atg gat gtc ccc aac atc aaa agg aat      293
Ile Cys Pro Ser Thr His Asn Met Asp Val Pro Asn Ile Lys Arg Asn
            75                  80                  85 gat ttc cag ctg att ggc atc cag gat ggg tac cta tcc ctg ctc cag      341
Asp Phe Gln Leu Ile Gly Ile Gln Asp Gly Tyr Leu Ser Leu Leu Gln
        90                  95                  100 gac agt ggg gag gta cga gag gac ctt cgt ctg cct gag gga gac ctt      389
Asp Ser Gly Glu Val Arg Glu Asp Leu Arg Leu Pro Glu Gly Asp Leu
    105                 110                 115 ggc aag gag att gag cag aag tat gac tgt gga gaa gag atc ctg atc      437
Gly Lys Glu Ile Glu Gln Lys Tyr Asp Cys Gly Glu Glu Ile Leu Ile
120                 125                 130                 135 aca gtg ctg tcc gcc atg aca gag gag gca gct gtt gca atc aag gct      485
Thr Val Leu Ser Ala Met Thr Glu Glu Ala Ala Val Ala Ile Lys Ala
                140                 145                 150 cgag                                                                  489
```

<210> SEQ ID NO 16
<211> LENGTH: 151
<212> TYPE: PRT
<213> ORGANISM: Rattus sp.

<400> SEQUENCE: 16

```
Met Ala Asp Asp Leu Asp Phe Glu Thr Gly Asp Ala Gly Ala Ser Ala
1               5                   10                  15

Thr Phe Pro Met Gln Cys Ser Ala Leu Arg Lys Asn Gly Phe Val Val
            20                  25                  30

Leu Lys Gly Arg Pro Cys Lys Ile Val Glu Met Ser Thr Ser Lys Thr
        35                  40                  45

Gly Lys His Gly His Ala Lys Val His Leu Val Gly Ile Asp Ile Phe
    50                  55                  60

Thr Gly Lys Lys Tyr Glu Asp Ile Cys Pro Ser Thr His Asn Met Asp
65                  70                  75                  80

Val Pro Asn Ile Lys Arg Asn Asp Phe Gln Leu Ile Gly Ile Gln Asp
                85                  90                  95

Gly Tyr Leu Ser Leu Leu Gln Asp Ser Gly Glu Val Arg Glu Asp Leu
            100                 105                 110

Arg Leu Pro Glu Gly Asp Leu Gly Lys Glu Ile Glu Gln Lys Tyr Asp
        115                 120                 125

Cys Gly Glu Glu Ile Leu Ile Thr Val Leu Ser Ala Met Thr Glu Glu
    130                 135                 140

Ala Ala Val Ala Ile Lys Ala
145                 150
```

<210> SEQ ID NO 17
<211> LENGTH: 20

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gtctgtgtat tattgggccc                                                   20

<210> SEQ ID NO 18
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcgaagcttc catggctcga gttttttttt tttttttttt tt                          42

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ttgaaggggt gaggaaaa                                                     18

<210> SEQ ID NO 20
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ttgagtggga taaag                                                        15

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aatcatctgc cattttaa                                                     18

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gccaagctta atggcagatg atttgg                                            26

<210> SEQ ID NO 23
<211> LENGTH: 25
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 23
ctgaattcca gttatttgc catgg                                          25

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aatgaattcc gccatgacag aggaggc                                       27

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 25
cctgtctcga agtccaagtc                                               20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 26
ggaccttggc gtggccgtgc                                               20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 27
ctcgtacctc cccgctgtcc                                               20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
aaactaccat ctccctgcc                                                20

<210> SEQ ID NO 29
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 29
tgccctacac aggctgaaag                                                      20

<210> SEQ ID NO 30
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
atcaagcttg cccaccatgg cagacg                                               26

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
aacgaattcc atgcctgatg tttccg                                               26

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tccgaattcg tacttctgct caatc                                                25

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Cys Arg Leu Pro Glu Gly Asp Leu Gly Lys Glu Ile Glu Gln Lys Tyr
 1               5                  10                  15

Asp

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      control oligonucleotide

<400> SEQUENCE: 34
cgtaacggta cggttccagg                                                      20

<210> SEQ ID NO 35
<211> LENGTH: 20
```

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 35
ggaccttggc gtggccgtgc                                                 20

<210> SEQ ID NO 36
<211> LENGTH: 460
<212> TYPE: DNA
<213> ORGANISM: Homo sapiens

<400> SEQUENCE: 36
atggcagacg aaattgattt cactactgga gatgccgggg cttccagcac ttaccctatg     60
cagtgctcgg ccttgcgcaa aaacggcttc gtggtgctca aaggacgacc atgcaaaata    120
gtggagatgt caacttccaa aactggaaag catggtcatg ccaaggttca ccttgttgga    180
attgatattt tcacgggcaa aaaatatgaa gatatttgtc cttctactca aacatggat    240 gttccaaata ttaagagaaa tgattatcaa ctgatatgca ttcaagatgg ttacctttcc    300
ctgctgacag aaactggtga agttcgtgag atcttaaac tgccagaagg tgaactaggc    360
aaagaaatag gggaaaaata caatgcaggt gaagatgtac aggtgtctgt catgtgtgca    420
atgagtgaag aatatgctgt agccataaaa ccctgcaaat                          460

<210> SEQ ID NO 37
<211> LENGTH: 462
<212> TYPE: DNA
<213> ORGANISM: Mus musculus

<400> SEQUENCE: 37
atggcagatg atttggactt cgagacagga gatgcagggg cctcagccac cttcccaatg     60
cagtgctcag cattacgtaa gaatggtttt gtggtgctca aaggccggcc atgtaagatc    120
gtcgagatgt ctacttcgaa gactggcaag catggccatg ccaaggtcca tctggttggc    180
attgacattt ttactgggaa gaaatatgaa gatatctgcc cgtcgactca taatatggat    240
gtccccaaca tcaaacgaaa tgacttccag ctgattggca tccaggatgg gtacctatcc    300
ctgctccagg acagtgggga ggtacgagag gaccttcgtc tgcctgaagg agaccttggc    360
aaggagattg agcagaagta tgactgtgga gaagagatcc tgatcacagt gctgtctgcc    420
atgacagagg aggcagctgt tgcaatcaag gccatggcaa aa                       462

<210> SEQ ID NO 38
<211> LENGTH: 154
<212> TYPE: PRT
<213> ORGANISM: Homo sapiens

<400> SEQUENCE: 38

Met Ala Asp Asp Leu Asp Phe Glu Thr Gly Asp Ala Gly Ala Ser Ala
 1               5                  10                  15

Thr Phe Pro Met Gln Cys Ser Ala Leu Arg Lys Asn Gly Phe Val Val
            20                  25                  30

Leu Lys Gly Arg Pro Cys Lys Ile Val Glu Met Ser Thr Ser Lys Thr
        35                  40                  45

Gly Lys His Gly His Ala Lys Val His Leu Val Gly Ile Asp Ile Phe
    50                  55                  60

Thr Gly Lys Lys Tyr Glu Asp Ile Cys Pro Ser Thr His Asn Met Asp

```
              65                  70                  75                  80
Val Pro Asn Ile Lys Arg Asn Asp Phe Gln Leu Ile Gly Ile Gln Asp
                    85                  90                  95

Gly Tyr Leu Ser Leu Gln Asp Ser Gly Glu Val Arg Glu Asp Leu
                100                 105                 110

Arg Leu Pro Glu Gly Asp Leu Gly Lys Glu Ile Glu Gln Lys Tyr Asp
            115                 120                 125

Cys Gly Glu Glu Ile Leu Ile Thr Val Leu Ser Ala Met Thr Glu Glu
    130                 135                 140

Ala Ala Val Ala Ile Lys Ala Met Ala Lys
145                 150

<210> SEQ ID NO 39
<211> LENGTH: 153
<212> TYPE: PRT
<213> ORGANISM: Homo sapiens

<400> SEQUENCE: 39

Met Ala Asp Glu Ile Asp Phe Thr Thr Gly Asp Ala Gly Ala Ser Ser
  1               5                  10                  15

Thr Tyr Pro Met Gln Cys Ser Ala Leu Arg Lys Asn Gly Phe Val Val
                 20                  25                  30

Leu Lys Gly Arg Pro Cys Lys Ile Val Glu Met Ser Thr Ser Lys Thr
            35                  40                  45

Gly Lys His Gly His Ala Lys Val His Leu Val Gly Ile Asp Ile Phe
        50                  55                  60

Thr Gly Lys Lys Tyr Glu Asp Ile Cys Pro Ser Thr His Asn Met Asp
 65                 70                  75                  80

Val Pro Asn Ile Lys Arg Asn Asp Tyr Gln Leu Ile Cys Ile Gln Asp
                    85                  90                  95

Gly Tyr Leu Ser Leu Leu Thr Glu Thr Gly Glu Val Arg Glu Asp Leu
                100                 105                 110

Lys Leu Pro Glu Gly Glu Leu Gly Lys Glu Ile Glu Gly Lys Tyr Asn
            115                 120                 125

Ala Gly Glu Asp Val Gln Val Ser Val Met Cys Ala Met Ser Glu Glu
    130                 135                 140

Tyr Ala Val Ala Ile Lys Pro Cys Lys
145                 150

<210> SEQ ID NO 40
<211> LENGTH: 154
<212> TYPE: PRT
<213> ORGANISM: Mus musculus

<400> SEQUENCE: 40

Met Ala Asp Asp Leu Asp Phe Glu Thr Gly Asp Ala Gly Ala Ser Ala
  1               5                  10                  15

Thr Phe Pro Met Gln Cys Ser Ala Leu Arg Lys Asn Gly Phe Val Val
                 20                  25                  30

Leu Lys Gly Arg Pro Cys Lys Ile Val Glu Met Ser Thr Ser Lys Thr
            35                  40                  45

Gly Lys His Gly His Ala Lys Val His Leu Val Gly Ile Asp Ile Phe
        50                  55                  60

Thr Gly Lys Lys Tyr Glu Asp Ile Cys Pro Ser Thr His Asn Met Asp
 65                 70                  75                  80

Val Pro Asn Ile Lys Arg Asn Asp Phe Gln Leu Ile Gly Ile Gln Asp
```

-continued

```
                85                  90                  95
Gly Tyr Leu Ser Leu Leu Gln Asp Ser Gly Glu Val Arg Glu Asp Leu
            100                 105                 110
Arg Leu Pro Glu Gly Asp Leu Gly Lys Glu Ile Glu Gln Lys Tyr Asp
        115                 120                 125
Cys Gly Glu Glu Ile Leu Ile Thr Val Leu Ser Ala Met Thr Glu Glu
130                 135                 140
Ala Ala Val Ala Ile Lys Ala Met Ala Lys
145                 150

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gacttggact tcgagacagg                                                  20

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gcacggccac gccaaggtc                                                   19

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ggacagcggg gaggtacgag                                                  20

<210> SEQ ID NO 44
<211> LENGTH: 1299
<212> TYPE: DNA
<213> ORGANISM: Homo sapiens

<400> SEQUENCE: 44
ggcacgaggg cggcggcggc ggtagaggcg gcggcggcgg cggcagcggg ctcggaggca      60
gcggttgggc tcgcggcgag cggacggggt cgagtcagtg cgttcgcgcg agttggaatc     120
gaagcctctt aaaatggcag atgacttgga cttcgagaca ggagatgcag gggcctcagc     180
caccttccca atgcagtgct cagcattacg taagaatggc tttgtggtgc tcaaaggccg     240
gccatgtaag atcgtcgaga tgtctacttc gaagactggc aagcacggcc acgccaaggt     300
ccatctggtt ggtattgaca tctttactgg gaagaaatat gaagatatct gcccgtcaac     360
tcataatatg gatgtcccca acatcaaaag gaatgacttc cagctgattg catccagga     420 tgggtaccta tcactgctcc aggacagcgg ggaggtacga gaggccttc gtctccctga     480 gggagacctt ggcaaggaga ttgagcagaa gtacgactgt ggagaagaga tcctgatcac     540
```

```
ggtgctgtct gccatgacag aggaggcagc tgttgcaatc aaggccatgg caaaataact    600
ggctcccagg atggcggtgg tggcagcagt gatcctctga acctgcagag gcccctccc     660 cgagcctggc ctggctctgg cccggtccta agctggactc ctcctacaca atttatttga    720
cgttttattt tggttttccc cacccctca atctgtcggg gagccctgc ccttcaccta      780 gctcccttgg ccaggagcga gcgaagctgt ggccttggtg aagctgccct cctcttctcc    840
cctcacacta cagccctggt gggggagaag ggggtgggtc tgcttgtgg tttagtcttt     900 tttttttttt tttttttttt tttaaattca atctggaatc agaaagcggt ggattctggc    960
aaatggtcct tgtgccctcc ccactcatcc ctggtctggt ccctgttgc ccatagccct     1020 ttaccctgag caccacccca acagactggg gaccagcccc ctcgcctgcc tgtgtctctc    1080
cccaaacccc tttagatggg gagggaagag gaggagaggg gaggggacct gcccctcct     1140 caggcatctg ggagggccct gccccatgg gctttaccct tccctgcggg ctctctcccc     1200
gacacatttg ttaaaatcaa acctgaataa aactacaagt ttaatatgaa aaaaaaaa      1260 aaaaaaaaa aaaaaaaaa aaaaaaaaa aaaaaaaa                               1299

<210> SEQ ID NO 45
<211> LENGTH: 465
<212> TYPE: DNA
<213> ORGANISM: Homo sapiens

<400> SEQUENCE: 45
atggcagatg acttggactt cgagacagga gatgcagggg cctcagccac cttcccaatg    60
cagtgctcag cattacgtaa gaatggcttt gtggtgctca aaggccggcc atgtaagatc    120
gtcgagatgt ctacttcgaa gactggcaag cacggccacg ccaaggtcca tctggttggt    180
attgacatct ttactgggaa gaaatatgaa gatatctgcc cgtcaactca taatatggat    240
gtccccaaca tcaaaaggaa tgacttccag ctgattggca tccaggatgg gtacctatca    300
ctgctccagg acagcgggga ggtacgagag gaccttcgtc tccctgaggg agaccttggc    360
aaggagattg agcagaagta cgactgtgga gaagagatcc tgatcacggt gctgtctgcc    420
atgacagagg aggcagctgt tgcaatcaag gccatggcaa ataa                     465

<210> SEQ ID NO 46
<211> LENGTH: 462
<212> TYPE: DNA
<213> ORGANISM: Homo sapiens

<400> SEQUENCE: 46
atggcagacg aaattgattt cactactgga gatgccgggg cttccagcac ttaccctatg    60
cagtgctcgg ccttgcgcaa aaacggcttc gtggtgctca aggacgacc atgcaaaata     120 gtggagatgt caacttccaa aactggaaag catggtcatg ccaaggttca ccttgttgga    180
attgatattt tcacgggcaa aaaatatgaa gatatttgtc cttctactca aacatggat     240 gttccaaata ttaagagaaa tgattatcaa ctgatatgca ttcaagatgg ttacctttcc    300
ctgctgacag aaactggtga agttcgtgag atcttaaac tgccagaagg tgaactaggc     360
aaagaaatag agggaaaata caatgcaggt gaagatgtac aggtgtctgt catgtgtgca    420
atgagtgaag aatatgctgt agccataaaa ccctgcaaat aa                       462

<210> SEQ ID NO 47
<211> LENGTH: 154
<212> TYPE: PRT
<213> ORGANISM: Homo sapiens
```

<400> SEQUENCE: 47

Met Ala Asp Asp Leu Asp Phe Glu Thr Gly Asp Ala Gly Ala Ser Ala
1               5                   10                  15

Thr Phe Pro Met Gln Cys Ser Ala Leu Arg Lys Asn Gly Phe Val Val
            20                  25                  30

Leu Lys Gly Trp Pro Cys Lys Ile Val Glu Met Ser Ala Ser Lys Thr
        35                  40                  45

Gly Lys His Gly His Ala Lys Val His Leu Val Gly Ile Asp Ile Phe
    50                  55                  60

Thr Gly Lys Lys Tyr Glu Asp Ile Cys Pro Ser Thr His Asn Met Asp
65              70                  75                  80

Val Pro Asn Ile Lys Arg Asn Asp Phe Gln Leu Ile Gly Ile Gln Asp
            85                  90                  95

Gly Tyr Leu Ser Leu Leu Gln Asp Ser Gly Glu Val Pro Glu Asp Leu
        100                 105                 110

Arg Leu Pro Glu Gly Asp Leu Gly Lys Glu Ile Glu Gln Lys Tyr Asp
        115                 120                 125

Cys Gly Glu Glu Ile Leu Ile Thr Leu Leu Ser Ala Met Thr Glu Glu
130                 135                 140

Ala Ala Val Ala Ile Lys Ala Met Ala Lys
145                 150

<210> SEQ ID NO 48
<211> LENGTH: 153
<212> TYPE: PRT
<213> ORGANISM: Homo sapiens

<400> SEQUENCE: 48

Met Ala Asp Glu Ile Asp Phe Thr Thr Gly Asp Ala Gly Ala Ser Ser
1               5                   10                  15

Thr Tyr Pro Met Gln Cys Ser Ala Leu Arg Lys Asn Gly Phe Val Val
            20                  25                  30

Leu Lys Gly Arg Pro Cys Lys Ile Val Glu Met Ser Thr Ser Lys Thr
        35                  40                  45

Gly Lys His Gly His Ala Lys Val His Leu Val Gly Ile Asp Ile Phe
    50                  55                  60

Thr Gly Lys Lys Tyr Glu Asp Ile Cys Pro Ser Thr His Asn Met Asp
65              70                  75                  80

Val Pro Asn Ile Lys Arg Asn Asp Tyr Gln Leu Ile Cys Ile Gln Asp
            85                  90                  95

Gly Tyr Leu Ser Leu Leu Thr Glu Thr Gly Glu Val Arg Glu Asp Leu
        100                 105                 110

Lys Leu Pro Glu Gly Glu Leu Gly Lys Glu Ile Glu Gly Lys Tyr Asn
        115                 120                 125

Ala Gly Glu Asp Val Gln Val Ser Val Met Cys Ala Met Ser Glu Glu
130                 135                 140

Tyr Ala Val Ala Ile Lys Pro Cys Lys
145                 150

SUPPRESSION OF EIF5A1 EXPRESSION BY THE USE OF ANTISENSE OLIGONUCLEOTIDES FOR THE PREVENTION OF RETINAL CELL DEATH IN THE GLAUCOMATOUS EYE

RELATED APPLICATIONS

This application claims priority to provisional application No. 60/451,677, filed Mar. 5, 2003, and also claims priority to U.S. application Ser. No. 10/277,969, filed Oct. 23, 2002, now U.S. Pat. No. 7,217,517 issued May 15, 2007, which is a continuation-in-part of U.S. application Ser. No. 10/200,148, filed Jul. 23, 2002, which is pending, which is a continuation-in-part of U.S. application Ser. No. 10/141,647, filed May 7, 2002, now U.S. Pat. No. 7,166,467 issued Jan. 23, 2007, which is a continuation-in-part of U.S. application Ser. No. 09/909,796, filed Jul. 23, 2001, now U.S. Pat. No. 6,867,237, issued Mar. 15, 2005.

FIELD OF THE INVENTION

The present invention relates to apoptosis-specific eucaryotic initiation Factor-5A (eIF-5A or also referred to herein as eIF5A1) and methods for suppression of eIF5A1 expression by the use of antisene oligonucleotides for the prevention of rentinal cell death in the glaucomatous eye.

BACKGROUND OF THE INVENTION

Apoptosis is a genetically programmed cellular event that is characterized by well-defined morphological features, such as cell shrinkage, chromatin condensation, nuclear fragmentation, and membrane blebbing. Kerr et al. (1972) Br. J. Cancer, 26, 239-257; Wyllie et al. (1980) Int. Rev. Cytol., 68, 251-306. It plays an important role in normal tissue development and homeostasis, and defects in the apoptotic program are thought to contribute to a wide range of human disorders ranging from neurodegenerative and autoimmunity disorders to neoplasms. Thompson (1995) Science, 267, 1456-1462; Mullauer et al. (2001) Mutat. Res, 488, 211-231. Although the morphological characteristics of apoptotic cells are well characterized, the molecular pathways that regulate this process have only begun to be elucidated.

One group of proteins that is thought to play a key role in apoptosis is a family of cysteine proteases, termed caspases, which appear to be required for most pathways of apoptosis. Creagh & Martin (2001) Biochem. Soc. Trans, 29, 696-701; Dales et al. (2001) Leuk. Lymphoma, 41, 247-253. Caspases trigger apoptosis in response to apoptotic stimuli by cleaving various cellular proteins, which results in classic manifestations of apoptosis, including cell shrinkage, membrane blebbing and DNA fragmentation. Chang & Yang (2000) Microbiol. Mol. Biol. Rev., 64, 821-846.

Pro-apoptotic proteins, such as Bax or Bak, also play a key role in the apoptotic pathway by releasing caspase-activating molecules, such as mitochondrial cytochrome c, thereby promoting cell death through apoptosis. Martinou & Green (2001) Nat. Rev. Mol. Cell. Biol., 2, 63-67; Zou et al. (1997) Cell, 90, 405-413. Anti-apoptotic proteins, such as Bcl-2, promote cell survival by antagonizing the activity of the pro-apoptotic proteins, Bax and Bak. Tsujimoto (1998) Genes Cells, 3, 697-707; Kroemer (1997) Nature Med., 3, 614-620. The ratio of Bax:Bcl-2 is thought to be one way in which cell fate is determined; an excess of Bax promotes apoptosis and an excess of Bcl-2 promotes cell survival. Salomons et al. (1997) Int. J. Cancer, 71, 959-965; Wallace-Brodeur & Lowe (1999) Cell Mol. Life. Sci., 55, 64-75.

Another key protein involved in apoptosis is that encoded by the tumor suppressor gene p53. This protein is a transcription factor that regulates cell growth and induces apoptosis in cells that are damaged and genetically unstable, presumably through up-regulation of Bax. Bold et al. (1997) Surgical Oncology, 6, 133-142; Ronen et al., 1996; Schuler & Green (2001) Biochem. Soc. Trans., 29, 684-688; Ryan et al. (2001) Curr. Opin. Cell Biol., 13, 332-337; Zornig et al. (2001) Biochem. Biophys. Acta, 1551, F1-F37.

The distinct morphological features that characterize cells undergoing apoptosis have given rise to a number of methods for assessing the onset and progress of apoptosis. One such feature of apoptotic cells that can be exploited for their detection is activation of a flippase, which results in externalization of phosphatidylserine, a phospholipid normally localized to the inner leaflet of the plasma membrane. Fadok et al. (1992) J. Immunol., 149, 4029-4035. Apoptotic cells bearing externalized phosphatidylserine can be detected by staining with a phosphatidylserine-binding protein, Annexin V, conjugated to a fluorescent dye. The characteristic DNA fragmentation that occurs during the apoptotic process can be detected by labeling the exposed 3'-OH ends of the DNA fragments with fluorescein-labeled deoxynucleotides. Fluorescent dyes that bind nucleic acids, such as Hoescht 33258, can be used to detect chromatin condensation and nuclear fragmentation in apoptotic cells. The degree of apoptosis in a cell population can also be inferred from the extent of caspase proteolytic activity present in cellular extracts.

As a genetically defined process, apoptosis, like any other developmental program, can be disrupted by mutation. Alterations in the apoptotic pathways are believed to play a key role in a number of disease processes, including cancer. Wyllie et al. (1980) Int. Rev. Cytol., 68, 251-306; Thompson (1995) Science, 267, 1456-1462; Sen & D'Incalci (1992) FEBS Letters, 307, 122-127; McDonnell et al. (1995) Seminars in Cancer and Biology, 6, 53-60. Investigations into cancer development and progression have traditionally been focused on cellular proliferation. However, the important role that apoptosis plays in tumorigenesis has recently become apparent. In fact, much of what is now known about apoptosis has been learned using tumor models, since the control of apoptosis is invariably altered in some way in tumor cells. Bold et al. (1997) Surgical Oncology, 6, 133-142.

Apoptosis can be triggered during tumor development by a variety of signals. Extracellular signals include growth or survival factor depletion, hypoxia and ionizing radiation. Internal signals that can trigger apoptosis include DNA damage, shortening telomeres, and oncogenic mutations that produce inappropriate proliferative signals. Lowe & Lin (2000) Carcinogenesis, 21, 485-495. Ionizing radiation and nearly all cytotoxic chemotherapy agents used to treat malignancies are thought to act by triggering endogenous apoptotic mechanisms to induce cell death. Rowan & Fisher (1997) Leukemia, 11, 457-465; Kerr et al. (1994) Cancer, 73, 2013-2026; Martin & Schwartz (1997) Oncology Research, 9, 1-5.

Evidence would suggest that early in the progression of cancer, tumor cells are sensitive to agents (such as ionizing radiation or chemotherapeutic drugs) that induce apoptosis. However, as the tumor progresses, the cells develop resistance to apoptotic stimuli. Naik et al. (1996) Genes and Development, 10, 2105-2116. This may explain why early cancers respond better to treatment than more advanced lesions. The ability of late-stage cancers to develop resistance to chemotherapy and radiation therapy appears to be linked to alterations in the apoptotic pathway that limit the ability of tumor cells to respond to apoptotic stimuli. Reed et al. (1996) *Journal of Cellular Biology*, 60, 23-32; Meyn et al. (1996) *Cancer Metastasis Reviews*, 15, 119-131; Hannun (1997) *Blood*, 89, 1845-1853; Reed (1995) *Toxicology Letters*, 82-83, 155-158; Hickman (1996) *European Journal of Cancer*, 32A, 921-926. Resistance to chemotherapy has been correlated to overexpression of the anti-apoptotic gene bcl-2 and deletion or mutation of the pro-apoptotic bax gene in chronic lymphocytic leukemia and colon cancer, respectively.

The ability of tumor cells to successfully establish disseminated metastases also appears to involve alterations in the apoptotic pathway. Bold et al. (1997) *Surgical Oncology*, 6, 133-142. For example, mutations in the tumor suppressor gene p53 are thought to occur in 70% of tumors. Evan et al. (1995) *Curr. Opin. Cell Biol.*, 7, 825-834. Mutations that inactivate p53 limit the ability of cells to induce apoptosis in response to DNA damage, leaving the cell vulnerable to further mutations. Ko & Prives (1996) *Genes and Development*, 10, 1054-1072.

Therefore, apoptosis is intimately involved in the development and progression of neoplastic transformation and metastases, and a better understanding of the apoptotic pathways involved may lead to new potential targets for the treatment of cancer by the modulation of apoptotic pathways through gene therapy approaches. Bold et al. (1997) *Surgical Oncology*, 6, 133-142.

Deoxyhypusine synthase (DHS) and hypusine-containing eucaryotic translation initiation Factor-5A (eIF-5A) are known to play important roles in many cellular processes including cell growth and differentiation. Hypusine, a unique amino acid, is found in all examined eucaryotes and archaebacteria, but not in eubacteria, and eIF-5A is the only known hypusine-containing protein. Park (1988) *J. Biol. Chem.*, 263, 7447-7449; Schuimann & Klink (1989) *System. Appl. Microbiol.*, 11, 103-107; Bartig et al. (1990) *System. Appl. Microbiol.*, 13, 112-116; Gordon et al. (1987a) *J. Biol. Chem.*, 262, 16585-16589. Active eEF-5A is formed in two post-translational steps: the first step is the formation of a deoxyhypusine residue by the transfer of the 4-aminobutyl moiety of spermidine to the α-amino group of a specific lysine of the precursor eIF-5A catalyzed by deoxyhypusine synthase; the second step involves the hydroxylation of this 4-aminobutyl moiety by deoxyhypusine hydroxylase to form hypusine.

The amino acid sequence of eIF-5A is well conserved between species, and there is strict conservation of the amino acid sequence surrounding the hypusine residue in eIF-5A, which suggests that this modification may be important for survival. Park et al. (1993) *Biofactors*, 4, 95-104. This assumption is further supported by the observation that inactivation of both isoforms of eIF-5A found to date in yeast, or inactivation of the DHS gene, which catalyzes the first step in their activation, blocks cell division. Schnier et al. (1991) *Mol. Cell. Biol.*, 11, 3105-3114; Sasaki et al. (1996) *FEBS Lett.*, 384, 151-154; Park et al. (1998) *J. Biol. Chem.*, 273, 1677-1683. However, depletion of eIF-5A protein in yeast resulted in only a small decrease in total protein synthesis suggesting that eEF-5A may be required for the translation of specific subsets of mRNA's rather than for protein global synthesis. Kang et al. (1993), "Effect of initiation factor eIF-5A depletion on cell proliferation and protein synthesis," in Tuite, M. (ed.), *Protein Synthesis and Targeting in Yeast*, NATO Series H. The recent finding that ligands that bind eIF-5A share highly conserved motifs also supports the importance of eIF-5A. Xu & Chen (2001) *J. Biol. Chem.*, 276, 2555-2561. In addition, the hypusine residue of modified eIF-5A was found to be essential for sequence-specific binding to RNA, and binding did not provide protection from ribonucleases.

The first cDNA for eIF-5A was cloned from human in 1989 by Smit-McBride et al., and since then cDNAs or genes for eIF-5A have been cloned from various eukaryotes including yeast, rat, chick embryo, alfalfa, and tomato. Smit-McBride et al. (1989a) *J. Biol. Chem.*, 264, 1578-1583; Schnier et al. (1991) (yeast); Sano, A. (1995) in Imahori, M. et al. (eds), *Polyamines, Basic and Clinical Aspects*, VNU Science Press, The Netherlands, 81-88 (rat); Rinaudo & Park (1992) *FASEB J*, 6, A453 (chick embryo); Pay et al. (1991) *Plant Mol. Biol.*, 17, 927-929 (alfalfa); Wang et al. (2001) *J. Biol. Chem.*, 276, 17541-17549 (tomato).

In addition, intracellular depletion of eIF-5A resulted in a significant accumulation of specific mRNAs in the nucleus, indicating that eIF-5A may be responsible for shuttling specific classes of mRNAs from the nucleus to the cytoplasm. Liu & Tartakoff (1997) Supplement to *Molecular Biology of the Cell*, 8, 426a. Abstract No. 2476, 37th American Society for Cell Biology Annual Meeting. The accumulation of eIF-5A at nuclear pore-associated intranuclear filaments and its interaction with a general nuclear export receptor further suggest that eIF-5A is a nucleocytoplasmic shuttle protein, rather than a component of polysomes. Rosorius et al. (1999) *J. Cell Science*, 112, 2369-2380.

Expression of eIF-5A mRNA has been explored in various human tissues and mammalian cell lines. For example, changes in eIF-5A expression have been observed in human fibroblast cells after addition of serum following serum deprivation. Pang & Chen (1994) *J. Cell Physiol.*, 160, 531-538. Age-related decreases in deoxyhypusine synthase activity and abundance of precursor eIF-5A have also been observed in senescing fibroblast cells, although the possibility that this reflects averaging of differential changes in isoforms was not determined. Chen & Chen (1997b) *J. Cell Physiol.*, 170, 248-254.

Studies have shown that eIF-5A may be the cellular target of viral proteins such as the human immunodeficiency virus type 1 Rev protein and human T cell leukemia virus type 1 Rex protein. Ruhl et al. (1993) *J. Cell Biol.*, 123, 1309-1320; Katahira et al. (1995) *J. Virol.*, 69, 3125-3133. Preliminary studies indicate that eIF-5A may target RNA by interacting with other RNA-binding proteins such as Rev, suggesting that these viral proteins may recruit eIF-5A for viral RNA processing. Liu et al. (1997) *Biol. Signals*, 6, 166-174.

Deoxyhypusine synthase and eIF-5A are known to play important roles in key cellular processes including cell growth and senescence. For example, antisense reduction of deoxyhypusine synthase expression in plants results in delayed senescence of leaves and fruits, indicating that there is a senescence-inducing isoform of eIF-5A in plants. See WO 01/02592; PCT/US01/44505; U.S. application Ser. No. 09/909,796. Inactivation of the genes for deoxyhypusine synthase or eIF-5A in yeast results in inhibition of cell division. Schnier et al. (1991) *Mol. Cell. Biol.*, 11, 3105-3114; Sasaki et al. (1996) *FEBS Lett.*, 384, 151-154; Park et al. (1998) *J. Biol. Chem.*, 273, 1677-1683.

Spermidine analogs have been successfully used to inhibit deoxyhypusine synthase in vitro, as well as to inhibit the formation of hypusine in vivo, which is accompanied by an inhibition of protein synthesis and cell growth. Jakus et al. (1993) *J. Biol. Chem.*, 268, 13151-13159; Park et al. (1994) *J. Biol. Chem.*, 269, 27827-27832. Polyamines themselves, in particular putrescine and spermidine, also appear to play important roles in cellular proliferation and differentiation. Tabor & Tabor (1984) *Annu. Rev. Biochem.*, 53, 749-790; Pegg (1988) *Cancer Res.*, 48, 759-774. For example, yeast mutants in which the polyamine biosynthesis pathway has been blocked are unable to grow unless provided with exogenous polyamines. Cohn et al. (1980) *J. Bacteriol.*, 134, 208-213.

Polyamines have also been shown to protect cells from the induction of apoptosis. For example, apoptosis of thymocytes has been blocked by exposure to spermidine and spermine, the mechanism of which appears to be the prevention of endonuclease activation. Desiderio et al. (1995) *Cell Growth Differ.*, 6, 505-513; Brune et al. (1991) *Exp. Cell Res.*, 195, 323-329. In addition, exogenous polyamines have been shown to repress B cell receptor-mediated apoptosis as well as apoptosis in the unicellular parasite, *Trypanosoma cruzi*. Nitta et al. (2001) *Exptl. Cell Res.*, 265, 174-183; Piacenza et al. (2001) *Proc. Natl. Acad. Sci.*, USA, 98, 7301-7306. Low concentrations of spermine and spermidine have also been observed to reduce the number of nerve cells lost during normal development of newborn rats, as well as protect the brain from neuronal damage during cerebral ischaemia. Gilad et al. (1985) *Brain Res.*, 348, 363-366; Gilad & Gilad (1991) *Exp. Neurol.*, 111, 349-355. Polyamines also inhibit senescence, a form of programmed cell death, of plant tissues. Spermidine and putrescine have been shown to delay post-harvest senescence of carnation flowers and detached radish leaves. Wang & Baker (1980) *HortScience*, 15, 805-806 (carnation flowers); Altman (1982) *Physiol. Plant.*, 54, 189-193 (detached radish leaves).

In other studies, however, induction of apoptosis has been observed in response to exogenous polyamines. For example, human breast cancer cell lines responded to a polyamine analogue by inducing apoptosis, and excess putrescine has been shown to induce apoptosis in DH23A cells. McCloskey et al. (1995) *Cancer Res.*, 55, 3233-3236; Tome et al. (1997) *Biochem. J*, 328, 847-854.

The results from these experiments with polyamines collectively suggest that existence of specific isoforms of eIF-5A play a role in induction of apoptosis. Specifically, the data are consistent with the view that there is an apoptosis-specific isoform of eIF-5A, which is activated by DHS. The fact that this DHS reaction requires spermidine is consistent with the finding that polyamines have been shown to elicit activation of caspase, a key executor of apoptosis-related proteolysis. Stefanelli et al. (2000) *Biochem. J.*, 347, 875-880; Stefanelli et al. (1999) *FEBS Lett.*, 451, 95-98. In a similar vein, inhibitors of polyamine synthesis can delay apoptosis. Das et al. (1997) *Oncol. Res.*, 9, 565-572; Monti et al. (1998) *Life Sci.*, 72, 799-806; Ray et al. (2000) *Am. J. Physiol.*, 278, C480-C489; Packham & Cleveland (1994) *Mol. Cell. Biol.*, 14, 5741-5747.

The finding that exogenous polyamines both inhibit and promote apoptosis can be explained by the fact that, depending upon the levels applied, they can either inhibit the DHS reaction leading to activation of eIF-5A and hence impede apoptosis, or induce apoptosis by reason of being toxic. The finding that low concentrations of exogenous polyamines block apoptosis in plant and animal systems is consistent with the fact that low concentrations of polyamines and their analogues act as competitive inhibitors of the DHS reaction. Indeed, even exogenous spermidine, which is a substrate for the DHS reaction, will impede the reaction through substrate inhibition. Jakus et al. (1993) *J. Biol. Chem.*, 268, 13153-13159.

However, all polyamines, and their analogues, are toxic at high concentrations and are able to induce apoptosis. This occurs despite their ability to inhibit activation of the putative apoptosis-specific isoform of eIF-5A for two reasons. First, activated eIF-5A has a long half-life. Torrelio et al. (1987) *Biochem. Biophys. Res. Commun.*, 145, 1335-1341; Dou & Chen (1990) *Biochim. Biophys. Acta.*, 1036, 128-137. Accordingly, depletion of activated apoptosis-specific eIF-5A arising from inhibition of deoxyhypusine synthase activity may not occur in time to block apoptosis caused by the toxic effects of spermidine. Second, polyamines are competitive inhibitors of the deoxyhypusine reaction and hence not likely to completely block the reaction even at concentrations that are toxic.

The present invention relates to cloning of an eIF-5A cDNA that is up regulated immediately before the induction of apoptosis. This apoptosis-specific eEF-5A is likely to be a suitable target for intervention in apoptosis-causing disease states since it appears to act at the level of post-transcriptional regulation of downstream effectors and transcription factors involved in the apoptotic pathway. Specifically, the apoptosis-specific eIF-5A appears to selectively facilitate the translocation of mRNAs encoding downstream effectors and transcription factors of apoptosis from the nucleus to the cytoplasm, where they are subsequently translated. The ultimate decision to initiate apoptosis appears to stem from a complex interaction between internal and external pro- and anti-apoptotic signals. Lowe & Lin (2000) *Carcinogenesis*, 21, 485-495. Through its ability to facilitate the translation of downstream apoptosis effectors and transcription factors, the apoptosis-related eIF-5A appears to tip the balance between these signals in favor of apoptosis.

As described previously, it is well established that anticancer agents induce apoptosis and that alterations in the apoptotic pathways can attenuate drug-induced cell death. Schmitt & Lowe (1999) *J. Pathol.*, 187, 127-137. For example, many anticancer drugs upregulate p53, and tumor cells that have lost p53 develop resistance to these drugs. However, nearly all chemotherapy agents can induce apoptosis independently of p53 if the dose is sufficient, indicating that even in drug-resistant tumors, the pathways to apoptosis are not completely blocked. Wallace-Brodeur & Lowe (1999) *Cell Mol. Life. Sci.*, 55, 64-75. This suggests that induction of apoptosis eIF-5A, even though it may not correct the mutated gene, may be able to circumvent the p53-dependent pathway and induce apoptosis by promoting alternative pathways.

Induction of apoptosis-related eIF-5A has the potential to selectively target cancer cells while having little or no effect on normal neighboring cells. This arises because mitogenic oncogenes expressed in tumor cells provide an apoptotic signal in the form of specific species of mRNA that are not present in normal cells. Lowe et al. (1993) *Cell*, 74, 954-967; Lowe & Lin (2000) *Carcinogenesis*, 21, 485-495. For example, restoration of wild-type p53 in p53-mutant tumor cells can directly induce apoptosis as well as increase drug sensitivity in tumor cell lines and xenographs. (Spitz et al., 1996; Badie et al. 1998).

The selectivity of apoptosis-eIF-5A arises from the fact that it selectively facilitates translation of mRNAs for downstream apoptosis effectors and transcription factors by mediating their translocation from the nucleus into the cytoplasm. Thus, for apoptosis eIF-5A to have an effect, mRNAs for these effectors and transcription factors have to be transcribed. Inasmuch as these mRNAs would be transcribed in cancer cells, but not in neighboring normal cells, it is to be expected that apoptosis eIF-5A would promote apoptosis in cancer cells but have minimal, if any, effect on normal cells. Thus, restoration of apoptotic potential in tumor cells with apoptosis-related eIF-5A may decrease the toxicity and side effects experienced by cancer patients due to selective targeting of tumor cells. Induction of apoptotic eIF-5A also has the potential to potentiate the response of tumor cells to anti-cancer drugs and thereby improve the effectiveness of these agents against drug-resistant tumors. This in turn could result in lower doses of anti-cancer drugs for efficacy and reduced toxicity to the patient.

Alternations in the apoptotic pathways are also believed to play a role in degeneration of retinal ganglion cells causing blindness due to glaucoma. Glaucoma describes a group of eye conditions in which increased intra-ocular pressure (IOP) leads to damage of the optic nerve and progressive blindness. Although glaucoma is currently managed by drugs or surgery to control IOP to reduce damage to the optic nerve or the use of neuro-protectors, there remains a need to protect retinal ganglion cells from degeneration by apoptosis in the glaucomatous eye.

SUMMARY OF INVENTION

The present invention provides isolated and/or purified rat apoptosis-specific eIF-5A and DHS nucleic acids and polypeptides and antisense oligonucleotides and expression vectors of apoptosis-specific eIF-5A and DHS. The present invention also provides isolated and/or purified apoptosis-specific eIF-5A (also referred to herein as human eIF-5A1 or apoptosis-specific eIF5 μl). The present invention also provides isolated and/or purified human eIF-5A2 (also referred to herein as proliferating eIF-5A or eIF5b). The present invention also provides methods of modulating apoptosis using apoptosis-specific eIF-5A and DHS.

Further, the invention provides methods of suppressing expression of apoptosis-specific eIF5A1 by the use of antisense oligonucleotides targeted at apoptosis-specific eIF5A1. Supressing xpression of apoptosis-specific eIF5A1 by the use of antisense oligonucleotides targeted at apoptosis-specific eIF5A1 provides methods of preventing retinal ganglion cell death in a glaucomatous eye.

BRIEF DESCRIPTION OF THE DRAWINGS

FIG. 1 depicts the nucleotide sequence (SEQ ID NO:11) and derived amino acid sequence (SEQ ID NO:12) of the 3' end of rat apoptosis-specific eIF-5A.

FIG. 2 depicts the nucleotide sequence (SEQ ID NO:15) and derived amino acid sequence (SEQ ID NO:16) of the 5' end of rat apoptosis-specific eIF-5A cDNA.

FIG. 3 depicts the nucleotide sequence (SEQ ID NO:1) and derived amino acid sequence (SEQ ID NO:2) of rat corpus luteum apoptosis-specific eIF-5A full-length cDNA.

FIG. 4 depicts the nucleotide sequence (SEQ ID NO:6) and derived amino acid sequence (SEQ ID NO:7) of the 3' end of rat apoptosis-specific DHS cDNA.

FIG. 5 is an alignment of the full-length coding sequence of rat corpus luteum apoptosis-specific eIF-5A cDNA (SEQ ID NO:5) with the coding sequence of human eIF-5A (Accession number BC000751 or NM_001970, SEQ ID NO:3).

FIG. 6 is an alignment of the full-length coding sequence of rat corpus luteum apoptosis-specific eIF-5A cDNA (SEQ ID NO:5) with the coding sequence of human eIF-5A (Accession number NM-020390, SEQ ID NO:36).

FIG. 7 is an alignment of the full-length coding sequence of rat corpus luteum apoptosis-specific eIF-5A cDNA (SEQ ID NO:5) with the nucleotide sequence of mouse eIF-5A (Accession number BC003889. SEQ ID NO:37).

FIG. 8 is an alignment of the derived full-length amino acid sequence of rat corpus luteum apoptosis-specific eIF-5A (SEQ ID NO:2) with the derived amino acid sequence of human eIF-5A (Accession number BC000751 or NM_001970, SEQ ID NO:38).

FIG. 9 is an alignment of the derived full-length amino acid sequence of rat corpus luteum apoptosis-specific eIF-5A (SEQ ID NO:2) with the derived amino acid sequence of human eIF-5A (Accession number NM_020390 SEQ ID NO:39).

FIG. 10 is an alignment of the derived full-length amino acid sequence of rat corpus luteum apoptosis-specific eIF-5A (SEQ ID NO:2) with the derived amino acid sequence of mouse eIF-5A (Accession number BC003889, SEQ ID NO:40).

FIG. 11 is an alignment of the partial-length nucleotide sequence of rat corpus luteum apoptosis-specific DHS cDNA (nucleotides 1-453 of SEQ ID NO:6) with the nucleotide sequence of human DHS (Accession number BC000333, SEQ ID NO:8).

FIG. 22 is a Northern blot (FIG. 22A) and ethidium bromide stained gel (FIG. 22B) of total RNA isolated from COS-7 cells after induction of apoptosis by withdrawal of serum probed with the $^{32}$P-dCTP-labeled 3'-untranslated region of rat corpus luteum apoptosis-specific DHS cDNA.

FIG. 27 illustrates detection of apoptosis as reflected by increased nuclear fragmentation when COS-7 cells were transiently transfected with pHM6 containing full-length rat apoptosis-specific eIF-5A in the sense orientation.

FIG. 33A is the Coomassie-blue-stained protein blot; FIG. 33B is the corresponding Western blot.

FIG. 38 is an alignment of human eIF5A2 isolated from RKO cells with the sequence of human eIF5A2 (Genbank accession number XM_113401).

FIGS. 50A-F report patient data where the levels of Apoptosis Factor eIF-5a (also denoted as eIF-5a1 or on the chart as IF5a1) are correlated with levels of IL-1β and IL-18.

FIG. 50A is a chart of data obtained from coronary artery bypass graft (CABG) patients. FIG. 50B is a chart of data obtained from valve replacement patients. FIG. 50C is a graph depicting the correlation of apoptosis factor eIF-5a (Factor 5a1) to IL-18 in CABG patients. FIG. 50D is a graph depicting the correlation of proliferating eIF-5a (Factor a2) to IL-18 in CABG patients. FIG. 50E is a graph depicting the correlation of apoptosis factor eIF-5a (Factor 5a1) to L-18 in valve replacement patients. FIG. 50F is a graph depicting the correlation of proliferating eIF-5a (Factor a2) to IL-18 in valve replacement patients.

FIG. 51 is a chart of the patient's data from which patients data used in FIGS. 50A-F was obtained.

FIG. 58 shows the binding position of three antisense oligonucleotides targeted against human eIF5A1 (SEQ ID NO: 44) (SEQ ID NOs. 41, 42, and 43 are disclosed respectively in order of appearance).

FIG. 59 shows the (A) coding sequence alignment and (B) amino acid alignment of human eIF5A1 (apoptosis-specific eIF5A) against human eIF5A2 (proliferating eIF5A) (FIG. 59A discloses SEQ ID NOs. 45 and 46: FIG. 59B discloses SEQ ID NOs. 47 and 48).

DETAILED DESCRIPTION OF THE INVENTION

Figure 12:
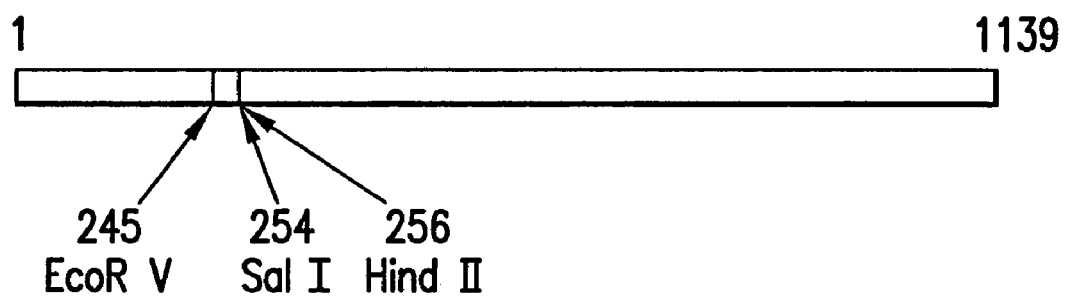
FIG. 12 is a restriction map of rat corpus luteum apoptosis-specific eIF-5A cDNA.
Figure 13:
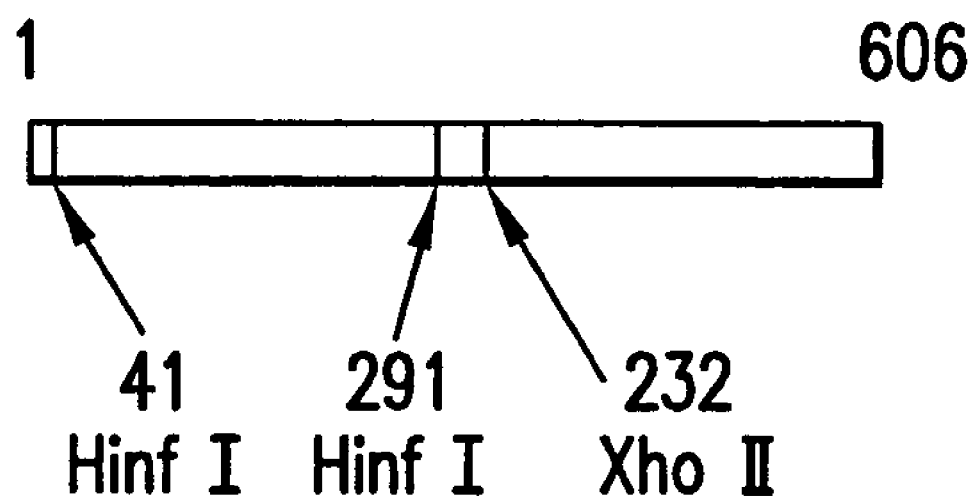
FIG. 13 is a restriction map of the partial-length rat apoptosis-specific DHS cDNA.

The present invention is based, in part, on the discovery and characterization of a full-length cDNA encoding an eIF-5A isolated from rat corpus luteum, which is involved in apoptosis (apoptosis-specific). Therefore, in one embodiment, the present invention provides an isolated nucleic acid comprising a nucleotide sequence encoding a rat apoptosis-specific eIF-5A polypeptide. Also provided by the present invention is a purified polypeptide comprising an amino acid sequence of a rat apoptosis-specific eIF-5A polypeptide. Rat apoptosis-specific eIF-5A polypeptide means any polypeptide specific to rats that is differentially expressed in apoptosing cells and that results from formation of a deoxyhypusine residue by the transfer of the 4-aminobutyl moiety of spermidine to the α-amino group of a specific conserved lysine of a precursor eIF-5A catalyzed by deoxyhypusine synthase and hydroxylation of this 4-aminobutyl moiety by deoxyhypusine hydroxylase to form hypusine, thereby activating eIF-5A.

In addition, the nucleic acid and polypeptide rat apoptosis-specific eIF-5A sequences of the present invention can be used to isolate apoptosis-specific nucleic acids and polypeptides from other cells, tissues, organs, or animals using guidance provided herein and techniques well known to those skilled in the art. The present invention also provides nucleic acid molecules that are suitable as primers or hybridization probes for the detection of nucleic acids encoding a rat apoptosis-specific eIF-5A polypeptide of the invention.

The nucleic acids of the present invention can be DNA, RNA, DNA/RNA duplexes, protein-nucleic acid (PNA), or derivatives thereof. As used herein, a nucleic acid or polypeptide is said to be "isolated" or "purified" when it is substantially free of cellular material or free of chemical precursors or other chemicals. It should be appreciated that the term isolated or purified does not refer to a library-type preparation containing a myriad of other sequence fragments. The nucleic acid or polypeptide of the present invention can be purified to homogeneity or other degrees of purity. The level of purification will be based on the intended use. The critical feature is that the preparation allows for the desired function of the nucleic acid or polypeptide, even if in the presence of considerable amounts of other components.

The isolated polypeptide can be purified from cells that naturally express it, purified from cells that have been altered to express it (recombinant), or synthesized using known protein synthesis methods. For example recombinant production of proteins involves cloning a nucleic acid molecule encoding either the apoptosis inducing eIF-5A or DHS into an expression vector. The expression vector is introduced into a host cell and the protein is expressed in the host cell. The protein can then be isolated from the cells by any appropriate purification scheme using standard protein purification techniques.

Preferably, the isolated nucleic acid encoding a rat apoptosis-specific eIF-5A polypeptide of the present invention has a nucleotide sequence of SEQ ID NO: 1 and the purified polypeptide of the present invention has an amino acid sequence of SEQ ID NO:2.

The present inventive rat apoptosis-specific eIF-5A nucleic acids and polypeptides also encompass sequences that have substantial sequence identity or homology to SEQ ID NO: 1 and SEQ ID NO:2, respectively, as well as functional derivatives and variants thereof.

As used herein, the term "substantial sequence identity" or "substantial homology" is used to indicate that a sequence exhibits substantial structural or functional equivalence with another sequence. Any structural or functional differences between sequences having substantial sequence identity or substantial homology will be de minimus; that is, they will not affect the ability of the sequence to function as indicated in the desired application. Differences may be due to inherent variations in codon usage among different species, for example. Structural differences are considered de minimus if there is a significant amount of sequence overlap or similarity between two or more different sequences or if the different sequences exhibit similar physical characteristics even if the sequences differ in length or structure. Such characteristics include, for example, the ability to hybridize under defined conditions, or in the case of proteins, immunological crossreactivity, similar enzymatic activity, etc. The skilled practitioner can readily determine each of these characteristics by art known methods.

Additionally, two nucleotide sequences are "substantially complementary" if the sequences have at least about 70 percent or greater, more preferably 80 percent or greater, even more preferably about 90 percent or greater, and most preferably about 95 percent or greater sequence similarity between them. Two amino acid sequences are substantially homologous if they have at least 50%, preferably at least 70%, more preferably at least 80%, even more preferably at least 90%, and most preferably at least 95% similarity between the active, or functionally relevant, portions of the polypeptides.

To determine the percent identity of two sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program. BLAST protein searches can be performed with the XBLAST program to obtain amino acid sequences homologous to the proteins of the invention. To obtain gapped alignments for comparison purposes, Gapped BLAST can be utilized as described in Altschul et al. (1997) *Nucleic Acids Res.* 25(17):3389-3402. When utilizing BLAST and gapped BLAST programs, the default parameters of the respective programs (e.g., XBLAST and NBLAST) can be used.

The term "functional derivative" of a nucleic acid is used herein to mean a homolog or analog of the gene or nucleotide sequence. A functional derivative may retain at least a portion of the function of the given gene, which permits its utility in accordance with the invention. "Functional derivatives" of the apoptosis-specific eIF-5A polypeptide as described herein are fragments, variants, analogs, or chemical derivatives of apoptosis-specific eIF-5A that retain at least a portion of the apoptosis-specific eIF-5A activity or immunological cross reactivity with an antibody specific for apoptosis-specific eIF-5A. A fragment of the apoptosis-specific eIF-5A polypeptide refers to any subset of the molecule.

Functional variants can also contain substitutions of similar amino acids that result in no change or an insignificant change in function. Amino acids that are essential for function can be identified by methods known in the art, such as site-directed mutagenesis or alanine-scanning mutagenesis (Cunningham et al. (1989) Science 244:1081-1085). The latter procedure introduces single alanine mutations at every residue in the molecule. The resulting mutant molecules are then tested for biological activity such as kinase activity or in assays such as an in vitro proliferative activity. Sites that are critical for binding partner/substrate binding can also be determined by structural analysis such as crystallization, nuclear magnetic resonance or photoaffinity labeling (Smith et al. (1992) J. Mol. Biol. 224:899-904; de Vos et al. (1992) Science 255:306-312).

A "variant" refers to a molecule substantially similar to either the entire gene or a fragment thereof, such as a nucleotide substitution variant having one or more substituted nucleotides, but which maintains the ability to hybridize with the particular gene or to encode mRNA transcript which hybridizes with the native DNA. A "homolog" refers to a fragment or variant sequence from a different animal genus or species. An "analog" refers to a non-natural molecule substantially similar to or functioning in relation to the entire molecule, a variant or a fragment thereof.

Variant peptides include naturally occurring variants as well as those manufactured by methods well known in the art. Such variants can readily be identified/made using molecular techniques and the sequence information disclosed herein. Further, such variants can readily be distinguished from other proteins based on sequence and/or structural homology to the eIF-5A or DHS proteins of the present invention. The degree of homology/identity present will be based primarily on whether the protein is a functional variant or non-functional variant, the amount of divergence present in the paralog family and the evolutionary distance between the orthologs.

Non-naturally occurring variants of the eIF-5A or DHS proteins of the present invention can readily be generated using recombinant techniques. Such variants include, but are not limited to deletions, additions and substitutions in the amino acid sequence of the proteins. For example, one class of substitutions are conserved amino acid substitution. Such substitutions are those that substitute a given amino acid in a protein by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., Science 247:1306-1310 (1990).

Alternatively, but also preferably, the nucleic acid encoding a rat apoptosis-specific eIF-5A polypeptide of the present invention hybridizes under highly stringent conditions with a nucleotide sequence that is complementary to that of SEQ ID NO:1. The term "hybridization" as used herein is generally used to mean hybridization of nucleic acids at appropriate conditions of stringency as would be readily evident to those skilled in the art depending upon the nature of the probe sequence and target sequences. Conditions of hybridization and washing are well known in the art, and the adjustment of conditions depending upon the desired stringency by varying incubation time, temperature and/or ionic strength of the solution are readily accomplished. See, e.g. Sambrook, J. et al., Molecular Cloning: A Laboratory Manual, 2$^{nd}$ edition, Cold Spring Harbour Press, Cold Spring Harbor, N.Y., 1989.

The choice of conditions is dictated by the length of the sequences being hybridized, in particular, the length of the probe sequence, the relative G-C content of the nucleic acids and the amount of mismatches to be permitted. Low stringency conditions are preferred when partial hybridization between strands that have lesser degrees of complementarity is desired. When perfect or near perfect complementarity is desired, high stringency conditions are preferred. For typical high stringency conditions, the hybridization solution contains 6×S.S.C., 0.01 M EDTA, 1×Denhardt's solution and 0.5% SDS. Hybridization is carried out at about 68° C. for about 3 to 4 hours for fragments of cloned DNA and for about 12 to 16 hours for total eucaryotic DNA. For lower stringencies, the temperature of hybridization is reduced to about 42° C. below the melting temperature ($T_m$) of the duplex. The $T_m$ is known to be a function of the G-C content and duplex length as well as the ionic strength of the solution.

As used herein, the phrase "hybridizes to a corresponding portion" of a DNA or RNA molecule means that the molecule that hybridizes, e.g., oligonucleotide, polynucleotide, or any nucleotide sequence (in sense or antisense orientation) recognizes and hybridizes to a sequence in another nucleic acid molecule that is of approximately the same size and has enough sequence similarity thereto to effect hybridization under appropriate conditions. For example, a 100 nucleotide long sense molecule will recognize and hybridize to an approximately 100 nucleotide portion of a nucleotide sequence, so long as there is about 70% or more sequence similarity between the two sequences. It is to be understood that the size of the "corresponding portion" will allow for some mismatches in hybridization such that the "corresponding portion" may be smaller or larger than the molecule which hybridizes to it, for example 20-30% larger or smaller, preferably no more than about 12-15% larger or smaller.

In addition, functional variants of polypeptides can also contain substitution of similar amino acids that result in no change or an insignificant change in function. Amino acids that are essential for function can be identified by methods known in the art, such as site-directed mutagenesis or alanine-scanning mutagenesis (Cunningham et al., Science 244:1081-1085 (1989)). The latter procedure introduces single alanine mutations at every residue in the molecule. The resulting mutant molecules are then tested for biological activity or in assays.

For example, an analog of apoptosis-specific eIF-5A refers to a non-natural protein or peptidomimetic substantially similar to either the entire protein or a fragment thereof. Chemical derivatives of apoptosis-specific eIF-5A contain additional chemical moieties not normally a part of the peptide or peptide fragment. Modifications can be introduced into peptide or fragment thereof by reacting targeted amino acid residues of the peptide with an organic derivatizing agent that is capable of reacting with selected side chains or terminal residues.

The initial discovery and characterization of a full-length cDNA encoding an apoptosis-specific eIF-5A isolated from rat corpus luteum led to the discovery and characterization of a partial-length cDNA clone encoding a DHS, which is also isolated from rat corpus luteum and involved in apoptosis. Accordingly, in an additional embodiment, the present invention provides an isolated nucleic acid comprising a nucleotide sequence encoding a rat apoptosis-specific DHS polypeptide. Also provided is a purified polypeptide comprising an amino acid sequence of a rat apoptosis-specific DHS polypeptide. Rat apoptosis-specific DHS polypeptide means any suitable polypeptide specific to rats that is differentially expressed in apoptosing cells and that catalyzes formation of a deoxyhypusine residue by the transfer of the 4-aminobutyl moiety of spermidine to the α-amino group of a specific conserved lysine of inactive eIF-5A to form deoxyhypusine, thereby activating eIF-5A.

Preferably, the isolated nucleic acid encoding a rat apoptosis-specific DHS polypeptide of the present invention has a nucleotide sequence of SEQ ID NO:6 and the purified polypeptide of the present invention has an amino acid sequence of SEQ ID NO:7. The present inventive rat apoptosis-specific DHS nucleic acids and polypeptides also encompass sequences that have substantial sequence identity or homology to SEQ ID NO:6 and SEQ ID NO:7, respectively, as well as functional derivatives and variants thereof, which have been described previously. Alternatively, and also preferably, the isolated nucleic acid of the present invention has a nucleotide sequence that hybridizes under highly stringent conditions with the complement of SEQ ID NO:6, which also has been described previously.

As is the case with the nucleic acids and polypeptides of the rat apoptosis-specific eIF-5A sequences described herein, the nucleic acids and polypeptides of the rat apoptosis-specific DHS sequences of the present invention can be used to isolate apoptosis-specific DHS nucleic acids and polypeptides from other animals, including humans. Isolation of such DHS sequences from animals and human can be achieved using art known methods and guidance provided herein, based on sequence similarities of at least 80% across species. The present invention also provides nucleic acid molecules that are suitable as primers or hybridization probes for the detection of nucleic acids encoding a rat apoptosis-specific DHS polypeptide of the invention.

Apoptosis-specific eIF-5A and DHS are suitable targets for regulation of apoptosis, including apoptosis underlying disease processes, since it likely acts in the post-transcriptional regulation of downstream effectors and transcription factors involved in the apoptotic pathway. Thus, the present invention also provides methods of modulating apoptosis in a cell by administering to the cell an agent that modulates apoptosis-specific eIF-5A and/or DHS function. It should be appreciated by one of skill in the art that the agent can be one that modulates only apoptosis-specific eIF-5A function, only apoptosis-specific DHS function alone, or both apoptosis-specific eIF-5A and DHS function.

Apoptosis can be modulated by any suitable alteration in the normal level of apoptosis-specific eIF-5A and/or DHS function in the cell. As intended herein, modification or alteration can be complete or partial and can include a change in transcriptional or translational control or other change altering apoptosis-specific eIF-5A and/or DHS function in the cell. Apoptosis-specific eIF-5A or DHS function means any activity relating to formation of a deoxyhypusine residue by the transfer of the 4-aminobutyl moiety of spermidine to the α-amino group of a specific conserved lysine of a precursor eIF-5A, which is catalyzed by DHS, and hydroxylation of this 4-aminobutyl moiety by deoxyhypusine hydroxylase to form hypusine, thereby activating eIF-5A.

In one embodiment of the present invention, the agent can inhibit apoptosis-specific eIF-5A and/or DHS function, thereby inhibiting apoptosis. Inhibiting apoptosis means any decrease, in intensity and/or number, and/or delay in onset of any or all of the well-defined morphological features characteristic of apoptosis, such as, for example, cell shrinkage, chromatin condensation, nuclear fragmentation, and membrane blebbing.

One agent that can inhibit apoptosis-specific eIF-5A and/or DHS function is an antisense oligonucleotide. Preferably, the antisense oligonucleotide has a nucleotide sequence encoding a portion of an apoptosis-specific eIF-5A polypeptide and/or an apoptosis-specific DHS polypeptide. Many suitable nucleic acid sequences encoding an apoptosis-specific eIF-5A polypeptide and/or DHS polypeptide are known in the art. For example, SEQ ID NOS:1, 3, 4, 5, 11, 15, 19, 20, and 21 (apoptosis-specific eIF-5A nucleic acid sequences), SEQ ID NOS:6 and 8 (apoptosis-specific DHS nucleic acid sequences), SEQ ID NOS:12 and 16 eIF-5A (apoptosis-specific polypeptide sequences), and SEQ ID NO:7 (apoptosis-specific DHS polypeptide sequences), or portions thereof, provide suitable sequences. Others suitable sequences can be found using the known sequences as probes according to the methods described herein.

Accordingly, the present invention also provides antisense oligonucleotides encoding a portion of an apoptosis-specific eIF-5A polypeptide and/or an apoptosis-specific DHS polypeptide, or a complement thereof. The antisense oligonucleotides of the present invention can be in the form of RNA or DNA, e.g., cDNA, genomic DNA, or synthetic RNA or DNA. The DNA can be double-stranded or single stranded, and if single stranded can be the coding strand or non-coding strand. The specific hybridization of an oligomeric compound with its target nucleic acid, resulting in interference with the normal function of the nucleic acid, is generally referred to as "antisense." The functions of DNA to be interfered with include replication and transcription. The functions of RNA to be interfered with include all functions such as, for example, translocation of the RNA to the site of protein translation, translation of protein from the RNA, splicing of the RNA to yield one or more mRNA species, and catalytic activity which can be engaged in or facilitated by the RNA. The overall effect of such antisense oligonucleotide is inhibiting of expression of apoptosis-specific eIF-5A and/or DHS and/or the amount of activated apoptosis-specific eIF-5A produced.

Figure 18:
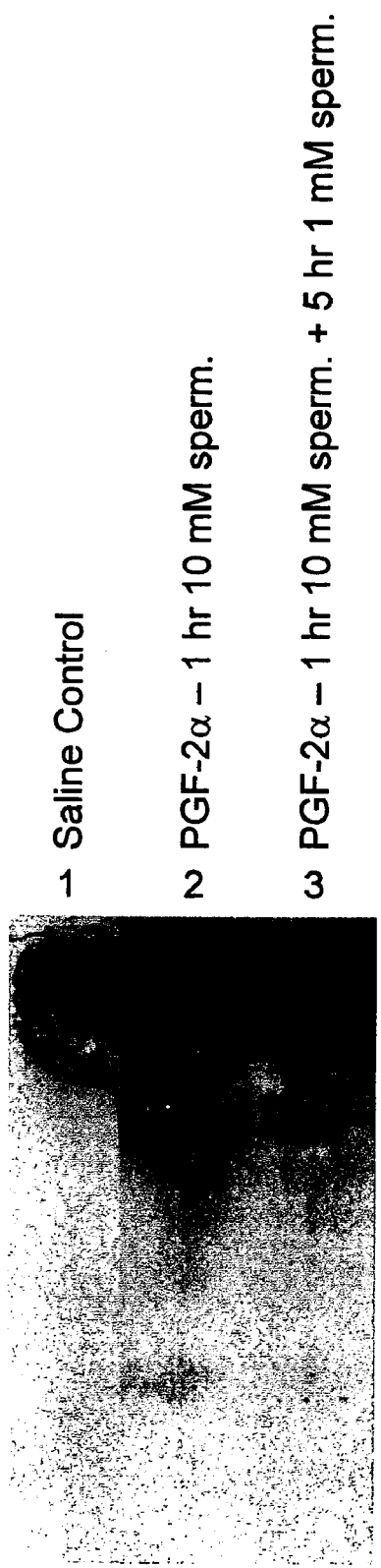
FIG. 18 depicts a DNA laddering experiment in which the degree of apoptosis in dispersed cells of superovulated rat corpora lutea was examined in rats treated with spermidine prior to exposure to prostaglandin F-2α (PGF-2α).
Figure 19:
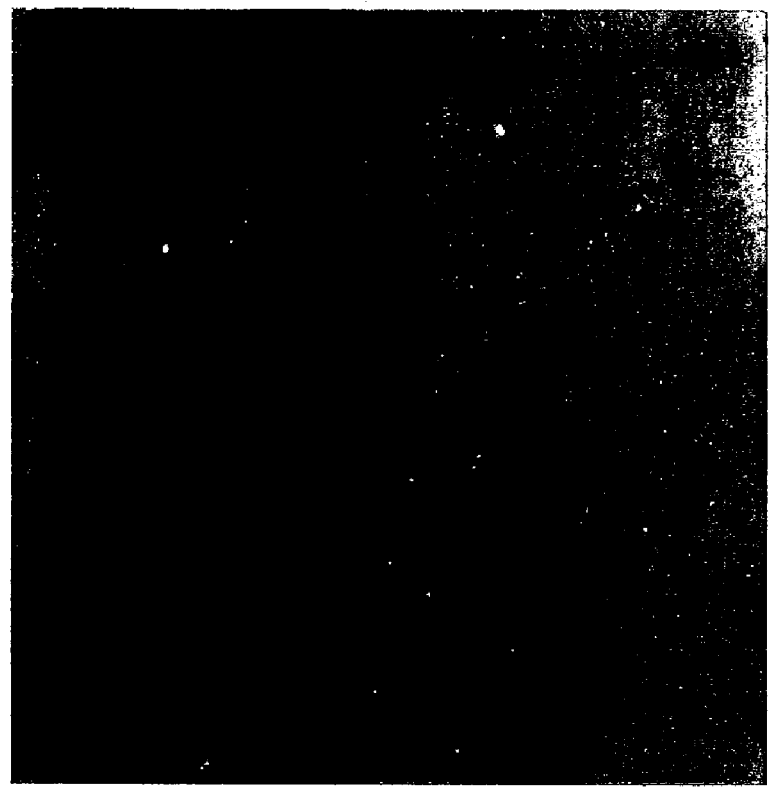
FIG. 19 depicts a DNA laddering experiment in which the degree of apoptosis in superovulated rat corpus lutea was examined in rats treated with spermidine and/or PGF-2α.

Alternatively, the activation of apoptosis-specific eIF-5A by apoptosis-specific DHS can be inhibited by administering chemical agents that inhibit the DHS enzymatic reaction. For example, the onset of DNA laddering reflecting apoptosis is delayed in rat corpus luteum when the animals are treated with spermidine, an inhibitor of the DHS reaction after induction of apoptosis by injection of PGF-2α (FIGS. 18-19). Jakus et al., (1993) *J. Biol. Chem.* 268: 13151-13159.

Apoptosis also can be inhibited or substantially decreased by adding agents that degrade apoptosis-specific eIF-5A DNA, RNA, or protein, or that degrade apoptosis-specific DHS DNA, RNA, or protein, thereby preventing the activation of apoptosis-specific eIF-5A by apoptosis-specific DHS. In another embodiment of the invention, inhibition of expression of endogenous mammalian apoptosis-specific DHS, apoptosis-specific eIF-5A, or both, are affected through the use of ribozymes. Examples of suitable drugs include those that inhibit the activation of apoptosis-specific eIF-5A by apoptosis-specific DHS, those that inhibit the activation of apoptosis-specific eIF-5A by deoxyhypusine hydroxylase, those that inhibit transcription and/or translation of apoptosis-specific DHS, those that inhibit transcription and/or translation of apoptosis-specific deoxyhypusine hydroxylase, and those that inhibit transcription or translation of apoptosis-specific eIF-5A. Examples of drugs that inhibit the activation of eIF-5A by apoptosis-specific DHS are spermidine, 1,3-Diamino-propane, 1,4-Diamino-butane (putrescine), 1,7-Diamino-heptane, or 1,8-Diamino-octane.

It is also possible to inhibit apoptosis-specific eIF-5A by inactivating the gene coding for apoptosis-specific eIF-5A in a cell. Such inactivation can occur by deleting the gene in the cell or by introducing a deletion or mutation into the gene and thereby inactivating the gene. The gene can also be inactivated by inserting into the gene another DNA fragment such that expression of the endogenous apoptosis-specific eIF-5A protein does not occur. Likewise, it is possible to inhibit activation of apoptosis-specific eIF-5A by inactivating the gene coding for apoptosis-specific DHS in a cell. Methods for introducing mutations, such as deletions and insertions, into genes in eukaryotic cells are known in the art, e.g., U.S. Pat. No. 5,464,764. Oligonucleotides and expression vectors useful for mutation of genes in cells can be made according to methods known in the art and guidance provided herein; for example, methods useful for making and expressing antisense oligonucleotides can be used to make oligonucleotides and expression vectors useful for mutating genes in cells.

It is also possible to inhibit expression of apoptosis-specific eIF-5A by suppressing expression of the gene coding for apoptosis-specific eIF-5A in a cell. Such inactivation can be accomplished via co-suppression, e.g., by introducing nucleotide sequence(s) coding for apoptosis-specific eIF-5A into a cell such that co-suppression occurs. Likewise, it is possible to inhibit activation of apoptosis-specific eIF-5A by suppressing the expression of the gene coding for apoptosis-specific DHS in a cell via co-suppression. Oligonucleotides and expression vectors useful for co-suppression can be made according to methods known in the art and guidance provided herein; for example, methods useful for making and expressing antisense oligonucleotides can be used to make oligonucleotides and expression vectors useful for co-suppression. Methods for co-suppression are known in the art, e.g., U.S. Pat. No. 5,686,649.

One result of the inhibition (through, e.g., antisense, mutation, or co-suppression) is a reduction in the amount of endogenous translatable apoptosis-specific eIF-5A or DHS-encoding mRNA. Consequently, the amount of apoptosis-specific DHS protein produced is reduced, thereby reducing the amount of activated eIF-5A, which in turn reduces translation of apoptosis-specific proteins. Apoptosis is thus inhibited or delayed, since de novo protein synthesis is required for the onset of apoptosis.

In another embodiment of the present invention, the agent can induce apoptosis-specific eIF-5A or DHS function, thereby inducing apoptosis. Inducing apoptosis means any increase, in intensity or number, or acceleration in onset of any or all of the well-defined morphological features characteristic of apoptosis, such as, for example, cell shrinkage, chromatin condensation, nuclear fragmentation, and membrane blebbing.

Any suitable agent that induces apoptosis-specific eIF-5A and/or DHS function can be used. It is appreciated by one of skill in the art that both the inactive and active forms of apoptosis-specific eIF-5A can be administered. If the inactive form, or hypusine-unmodified form, is administered, native apoptosis-specific DHS will activate the eIF-5A. Many suitable nucleic acid sequences encoding an apoptosis-specific eIF-5A polypeptide and/or DHS polypeptide are known in the art. For example, SEQ ID NOS:1, 3, 4, 5, 11, 15, 19, 20, and 21 (apoptosis-specific eIF-5A nucleic acid sequences), SEQ ID NOS:6 and 8 (apoptosis-specific DHS nucleic acid sequences), SEQ ID NOS:12 and 16 eIF-5A (apoptosis-specific polypeptide sequences), and SEQ ID NO:7 (apoptosis-specific DHS polypeptide sequences), or portions thereof, provide suitable sequences. Others suitable sequences can be found using the known sequences as probes according to the methods described herein.

For example, naked nucleic acids (naked DNA vectors such as oligonucleotides or plasmids), or polypeptides, including recombinantly produced polypeptides, can be administered to a cell. Recombinantly produced polypeptides means that the DNA sequences encoding the eIF-5A or the DHS proteins are placed into a suitable expression vector, which is described in detail below. The host is transfected with the expression vector and thereafter produces the desired polypeptides. The polypeptides are then isolated from the host cell. Recombinant apoptosis-inducing eIF-5A protein can be made, for example, in Chinese Hamster Ovary (CHO) cells and activated using recombinant DHS by those skilled in the art. Wang et al. (2001) *J. Biol. Chem.*, 276, 17541-17549; Eriksson et al., (2001) *Semin. Hematol.*, 38, 24-31. The polypeptides can also be synthetic, which are synthesized using known protein synthesis methods.

Polypeptide uptake can be facilitated using ligands, for example, a ligand derived from anthrax that mediates uptake into a broad range of cells. Liu et al. (2001) *J. Biol. Chem.*, 276, 46326-46332. Recombinant protein can also be administered to target cells, tissues, and organs of mammals using liposomes. Liposomes occluding the protein are administered intravenously. Targeting can be achieved by incorporating ligands to specific cell receptors into the liposomes. See, e.g., Kaneda, Adv Drug Delivery Rev 43: 197-205 (2000).

One preferred agent that can induce apoptosis-specific eIF-5A or DHS function is an expression vector. Accordingly, the present invention provides expression vectors having a promoter operably linked to a nucleic acid encoding an apoptosis-specific eIF-5A polypeptide and/or DHS polypeptide. The expression vectors of the present invention can be in the form of RNA or DNA, e.g., cDNA, genomic DNA, or synthetic RNA or DNA. The DNA can be double-stranded or single stranded, and if single stranded can be the coding strand or non-coding strand. Any appropriate expression vector (see, e.g., Pouwels et al., Cloning Vectors: A Laboratory Manual (Elsevior, N.Y.: 1985)) can be used. Preferably, the expression vector has a promoter sequence operably linked to a nucleotide sequence encoding an apoptosis-specific (related) eIF-5A polypeptide and/or apoptosis-specific (related) DHS polypeptide.

Within the expression vector, the desired nucleic acid and the promoter are operably linked such that the promoter is able to drive the expression of the nucleic acid. Any suitable promoter can be used provided that the nucleic acid is expressed. Examples of such suitable promoters include various viral promoters, eucaryotic promoters, and constitutively active promoters. As long as this operable linkage is maintained, the expression vector can include more than one nucleic acid (e.g., nucleic acids encoding both apoptosis-specific eIF-5A and/or DHS). The expression vector can optionally include other elements, such as polyadenylation sequences, ribosome entry sites, transcriptional regulatory elements (e.g., enhancers, silencers, etc.), other sequences for enhancing the stability of the vector or transcript or the translation or processing of the desired transcript within the cells (e.g., secretion signals, leaders, etc.), or any other suitable element.

Expression vector can be derived from viruses such as adenovirus, adeno-associated virus, herpesvirus, retrovirus or lentivirus. The expression vector of the present invention can be transfected into host cells, which include, but are not limited to, bacterial species, mammalian or insect host cell systems including baculovirus systems (see, e.g., Luckow et al., Bio/Technology, 6, 47 (1988)), and established cell lines such 293, COS-7, C127, 3T3, CHO, HeLa, BHK, etc.

Adenoviral vectors are preferred because, unlike plasmids and other viral vectors (e.g., herpes simplex virus), adenoviral vectors achieve gene transfer in both dividing and nondividing cells, with high levels of protein expression in cardiovascular relevant sites such as myocardium, vascular endothelium, and skeletal muscle. Furthermore, the gene transferred by an adenoviral vector functions in an epichromosomal position and thus carries little risk of inappropriately inserting the transferred gene into a critical site of the host genome. The adenoviral vector also desirably is deficient in at least one gene function required for viral replication. Preferably, the adenoviral vector is deficient in at least one essential gene function of the E1, E2, and/or E4 regions of the adenoviral genome. More preferably, the vector additionally is deficient in at least part of the E3 region of the adenoviral genome (e.g., an XbaI deletion of the E3 region).

Recombinant adenovirus can be delivered to cultured cells by simply adding the virus to the culture media. Infection of host animals/humans can be achieved by directly injecting the viral particles into the bloodstream or into the desired tissue. The half-life of the virus in serum can be extended by complexing the virus with liposomes (e.g. Lipofectin, Life Technologies) or polyethylene glycol. The adenovirus vector normally enters the cell through an interaction between the knob domain of the viral fiber protein and the coxsackievirus and adenovirus receptor, CAR. The viral vector can be directed to specific cells, or to cells which do not express the CAR, by genetically engineering the virus to express a ligand specific to a certain cell receptor.

In an alternate embodiment, apoptosis can be initiated or enhanced by chemically upregulating the transcription of endogenous apoptosis-specific eIF-5A, or apoptosis-specific DHS, or both, with chemicals, or by chemically enhancing the activation of apoptosis-specific eIF-5A. In one such embodiment, PGF-2α is administered to the cancer cells or tumor of the animal/human to upregulate the transcription of DHS and eIF-5A.

Apoptosis-specific eIF-5A is a suitable target for regulation of apoptosis, including apoptosis underlying disease processes, since it likely acts in the post-transcriptional regulation of downstream effectors and transcription factors involved in the apoptotic pathway. The present inventive methods of modulating apoptosis-specific eIF-5A and apoptosis-specific DHS, either alone or in combination, can be accomplished in cells of animals resulting in induction or enhancement of apoptosis and giving rise to novel methods and compositions for the treatment and prevention of diseases caused by, causing, or otherwise having an etiology associated with an inability of cells to undergo apoptosis.

Many important human diseases are caused by abnormalities in the control of apoptosis. These abnormalities can result in either a pathological increase in cell number (e.g. cancer) or a damaging loss of cells (e.g. degenerative diseases). As non-limiting examples, the methods and compositions of the present invention can be used to prevent or treat the following apoptosis-associated diseases and disorders: neurological/neurodegenerative disorders (e.g., Alzheimer's, Parkinson's, Huntington's, Amyotrophic Lateral Sclerosis (Lou Gehrig's Disease), autoimmune disorders (e.g., rheumatoid arthritis, systemic lupus erythematosus (SLE), multiple sclerosis), Duchenne Muscular Dystrophy (DMD), motor neuron disorders, ischemia, heart ischemia, chronic heart failure, stroke, infantile spinal muscular atrophy, cardiac arrest, renal failure, atopic dermatitis, sepsis and septic shock, AIDS, hepatitis, glaucoma, diabetes (type 1 and type 2), asthma, retinitis pigmentosa, osteoporosis, xenograft rejection, and burn injury.

One such disease caused by abnormalities in the control of apoptosis is glaucoma. Apoptosis is a critical factor leading to blindness in glaucoma patients. Glaucoma is a group of eye conditions arising from damage to the optice nerve that results in progressive blindness. Apoptosis has been shown to be a direct cause of this optice nerve damage.

Early work in the field of glaucoma research has indicated that elevated IOP leads to interference in axonal transport at the level of the lamina cribosa (a perforated, collagenous connective tissue) that is followed by the death of retinal ganglion cells. Quigley and Anderson (1976) *Invest. Opthalmol. Vis. Sci.*, 15, 606-16; Minckler, Bunt, and Klock, (1978) *Invest. Opthalmol. Vis. Sci.*, 17, 33-50; Anderson and Hendrickson, (1974) *Invest. Opthalmol. Vis. Sci.*, 13, 771-83; Quigley et al., (1980) *Invest. Opthalmol. Vis. Sci.*, 19, 505-17. Studies of animal models of glaucoma and postmortem human tissues indicate that the death of retinal ganglion cells in glaucoma occurs by apoptosis. Garcia-Valenzuela e. al., (1995) *Exp. Eye Res.*, 61, 33-44; Quigley et al., (1995) *Invest. Opthalmol. Vis. Sci.*, 36, 774-786; Monard, (1998) In: Haefliger I O, Flammer J (eds) *Nitric Oxide and Endothelin in the Pathogenesis of Glaucoma*, New York, N.Y., Lippincott-Raven, 213-220. The interruption of axonal transport as a result of increased IOP may contribute to retinal ganglion cell death by deprivation of trophic factors. Quigley, (1995) *Aust N Z J Opthalmol*, 23(2), 85-91. Optic nerve head astrocytes in glaucomatous eyes have also been found to produce increased levels of some neurotoxic substances. For example, increased production of tumor necrosis factor-α (TNF-α) (Yan et al., (2000) *Arch. Opthalmol.*, 118, 666-673), and nitric oxide synthase (Neufeld et al., (1997) *Arch. Opthalmol.*, 115, 497-503), the enzyme which gives rise to nitric oxide, has been found in the optic nerve head of glaucomatous eyes. Furthermore, increased expression of the inducible form of nitric oxide synthase (iNOS) and TNF-α by activated retinal glial cells have been observed in rat models of hereditary retinal diseases. Cotinet et al., (1997) *Glia*, 20, 59-69; de Kozak et al., (1997) *Ocul. Immunol. Inflamm.*, 5, 85-94; Goureau et al., (1999) *J. Neurochem*, 72, 2506-2515. In the glaucomatous optic nerve head, excessive nitric oxide has been linked to the degeneration of axons of retinal ganglion cells. Arthur and Neufeld, (1999) *Surv Opthalmol*, 43 (Suppl 1), S129-S135. Finally, increased production of TNF-α by retinal glial cells in response to simulated ischemia or elevated hydrostatic pressure has been shown to induce apoptosis in cocultured retinal ganglion cells. Tezel and Wax, (2000) *J. Neurosci.*, 20(23), 8693-8700.

Protecting retinal ganglion cells from degeneration by apoptosis is under study as a potential new treatment for blindness due to glaucoma. Antisense oligonucleotides have been used by several groups to target key proteins in the apoptotic process in order to protect retinal ganglion cells from apoptotic cell death. Antisense oligonucleotides are short, synthetic strands of DNA (or DNA analogs) that are antisense (or complimentary) to a specific DNA or RNA target. Antisense oligonucleotides are designed to block expression of the protein encoded by the DNA or RNA target by binding to the target and halting expression at the level of transcription, translation, or splicing. One of the hurdles to using antisense oligonucleotides as a drug is the rapid degradation of oligonucleotides in blood and in cells by nucleases. This problem has been addressed by using modified backbones that resist degradation (Blake et al., (1985) *Biochemistry*, 24, 6139-6145) such as replacement of the phosphodiester bonds in the oligonucleotides with phosphorothioate linkages to retard nuclease degradation. Matzura and Eckstein, (1968) *Eur. J. Biochem.*, 3, 448-452.

Antisense oligonucleotides have been used successfully in animal models of eye disease. In a model of transient global retinal ischemia, expression of caspase 2 was increased during ischemia, primarily in the inner nuclear and ganglion cell layers of the retina. Suppression of caspase using an antisense oligonucleotide led to significant histopathologic and functional improvement as determined by electroretinogram. Singh et al., (2001) *J. Neurochem.*, 77(2), 466-75. Another study demonstrated that, upon transection of the optic nerve, retinal ganglion cells upregulate the pro-apoptotic protein Bax and undergo apoptosis. Repeated injections of a Bax antisense oligonucleotide into the temporal superior retina of rats inhibited the local expression of Bax and increased the number of surviving retinal ganglion cells following transaction of the optic nerve. Isenmann et al., (1999) *Cell Death Differ.*, 6(7). 673-82.

Delivery of antisense oligonucleotides to retinal ganglion cells has been improved by encapsulating the oligonucleotides in liposomes, which were then coated with the envelope of inactivated hemagglutinating virus of Japan (HVJ; Sendai virus) by fusion (HVJ liposomes). Intravitreal injection into mice of FITC-labeled antisense oligonucleotides encapsulated in HVJ liposomes resulted in high fluorescence within 44% of the cells in the ganglion layer which lasted three days while fluorescence with naked FITC-labeled antisense oligonucleotide disappeared after one day. Hangai et al., (1998) *Arch Opthalmol*, 116(7), 976.

A method of preventing or modulating apoptosis of the present invention is directed to modulating apoptosis in the cells of the eye, such as but not limited to, astrocytes, retinal ganglion, retinal glial cells and lamina cribosa. Death of retintal ganglion cells in glaucoma occurs by apoptosis. Thus, providing a method of inhibiting apoptosis in rentinal ganglion cells or by protecting retinal ganglion cells from degeneration by apoptosis provides a novel treatment for prevention of blindness due to glaucoma.

The present invention provides a method for preventing retinal ganglion cell death in a glaucomatous eye, by suppressing expression of apoptosis-specific eIF5A1. Inhibiting the expression of apoptosis-specific eIF5A1 reduces apoptosis. Apoptosis-specific eIF5A1 is a powerful gene that appears to regulate the entire apoptic process. Thus, controlling apoptosis in the optice nerve head indicates that blocking expression of apoptosis-specific eIF5A1 provides a treatment for glaucoma.

Suppression of expression of apoptosis-specific eIF5A1 is accomplished by administering antisense oligonucleotides targeted against human apoptosis-specific eIF5A1 to cells of the eye such as, but not limited to lamina crobosa, astrocytes, retinal ganglion, or retinal glial cells. Antisense oligonucleotides are as defined above, i.e. have a nucleotide sequence encoding at least a portion of an apoptosis-specific eIF5A1 polypeptide. Antisense oligonucleotides targeted against human apoptosis-specific eIF5A1 have a nucleotide sequence encoding at least a portion of human apoptosis-specific eIF5A1 polypeptide. Preferred antisense oligonucleotides comprise SEQ ID NO:26 or 27 or oligonucleotides that bind to a sequence complementary to SEQ ID NO:26 or 27 under high stringency conditions.

Another embodiment of the invention provides a method of suppressing expression of apoptosis-specific eIF5A1 in lamina cribosa cells, astrocyte cells, retinal ganglion cells or retinal glial cells. Antisense oligonucleotides, such as but not limited to, SEQ ID NO:26 and 27, targeted against human apoptosis-specific eIF5A1 are administered to lamina cribosa cells, astrocyte cells, retinal ganglion cells or retinal glial cells. The cells may be human.

The inventors of the present invention have shown that apoptosis eIF-5a levels correlate with elevated levels of two cytokines (Interleukin 1-beta "IL-1β" and interleukin 18 "L-18") in ischemic heart tissue, thus further proving that apoptosis eIF-5a is involved in cell death and present in ischemic heart tissue. This apoptosis eIF-factor 5a/interleukin correlation has not been seen in non-ischemic heart tissue. See FIGS. 50A-F and 51. Using PCR measurements, levels of apoptosis eIF-5a, proliferating eIF-5a, IL-1, and IL-18 were measured and compared in various ischemic heart tissue (from coronary bypass graft and valve (mitral and atrial valve) replacement patients).

The correlation of apoptosis eIF-5a to these potent interleukins further suggests that the inflammation and apoptosis pathways in ischemia may be controlled via controlling apoptosis eIF-5a. Thus, inhibiting the expression of apoptosis eIF-5a through one of the present inventions, such as the use of antisense molecules, for example, the actions of these interleukins may also be inhibited (by virtue of their down regulation) and thereby prevent or delay cell death as well as inhibit or prevent problems associated with the accumulation of IL-1β and/or IL-18 (i.e. cell death and tissue damage). IL-1 has been associated with a variety of inflammatory diseases such as Chron's disease, arthritis, and multiple sclerosis. IL-18 has been associated with premature programmed cell death. Thus, by down regulating apoptosis eIF-5a with one of the present inventions, the expression of IL-1β or IL-18 may be downregulated, and thus, the damaging effects of these inflammatory cytokines may also be down regulated.

The present inventive methods can be used for therapeutic treatments to an animal having a cancerous cell or suffering from a tumor in an amount sufficient to kill the cancerous cell or inhibit the progression of the tumor, respectively. An amount adequate to accomplish this is defined as a therapeutically effective dose. Amounts effective for this use will depend upon the severity of the disease and the general state of the animal's own immune system.

Inhibition of tumor growth means prevention or reduction of the progression of the tumor, e.g, the growth, invasiveness, metastases and/or recurrence of the tumor. The present inventive methods can be used to treat any suitable tumor, including, for example, tumors of the breast, heart, lung, small intestine, colon, spleen, kidney, bladder, head and neck, ovary, prostate, brain, pancreas, skin, bone, bone marrow, blood, thymus, uterus, testicles, cervix or liver. Animals, preferably mammals, and more preferably humans can be treated using the compositions and methods of the present invention. The present inventive methods can thus be carried out in vitro, ex vivo, or in vivo.

Dosing schedules will also vary with the disease state and status of the animal, and will typically range from a single bolus dosage or continuous infusion to multiple administrations per day (e.g., every 4-6 hours), or as indicated by the treatment and the animal's condition. It should be noted, however, that the present invention is not limited to any particular dose.

In the present invention, any suitable method or route can be used for administration, for example, oral, intravenous, intraperitoneal, subcutaneous, or intramuscular administration. The dose of antagonist administered depends on numerous factors, including, for example, the type of molecule administered, the type and severity tumor being treated and the route of administration. It should be emphasized, however, that the present invention is not limited to any particular method or route of administration.

In one alternative embodiment, the present inventive methods can be used in combination with one or more traditional therapies. For example, a suitable antineoplastic agent can be used, such as a chemotherapeutic agent or radiation. In an additional alternative embodiment, the present inventive methods can be used in combination with one or more suitable adjuvants, such as, for example, cytokines (IL-10 and IL-13, for example) or other immune stimulators.

In another alternative embodiment, diagnosis of an apoptosis-related or associated disorder (such as ischemia of the heart tissue) can be made by measuring the expression levels of apoptosis-specific eIF-5A and proliferating eIF-5A (eIF-5b). The proliferating eIF-5A (eIF-5b) and the apoptosis-specific eIF-5A differ in that they are transcribed from different locations by different promoters; although the two are structurally homologous, with differences in the carboxy terminus. The method of diagnosis of the present invention involves comparing the amount of proliferating eIF-5A present in a given cell with the amount of apoptosis-specific eIF-5A present in the same cell. The levels of gene expression are measured for both proliferating eIF-5A and apoptosis-specific eIF-5A and compared to each other. During normal functioning, a cell will have either the same amount or greater amount of proliferating eIF-5A (also referred to herein as eIF-5A2) than apoptosis-specific eIF-5A (also referred to herein as eIF-5A1). However, in cells undergoing death or stress such as ischemia, the apoptosis-specific eIF-5A is expressed at a greater level than the proliferating eIF-5A. Thus, detecting the increased levels of expression of apoptosis-specific eIF-5A, provides for method of identifying or diagnosing an apoptosis-related or associated disorder (such as ischemia).

Figure 46:
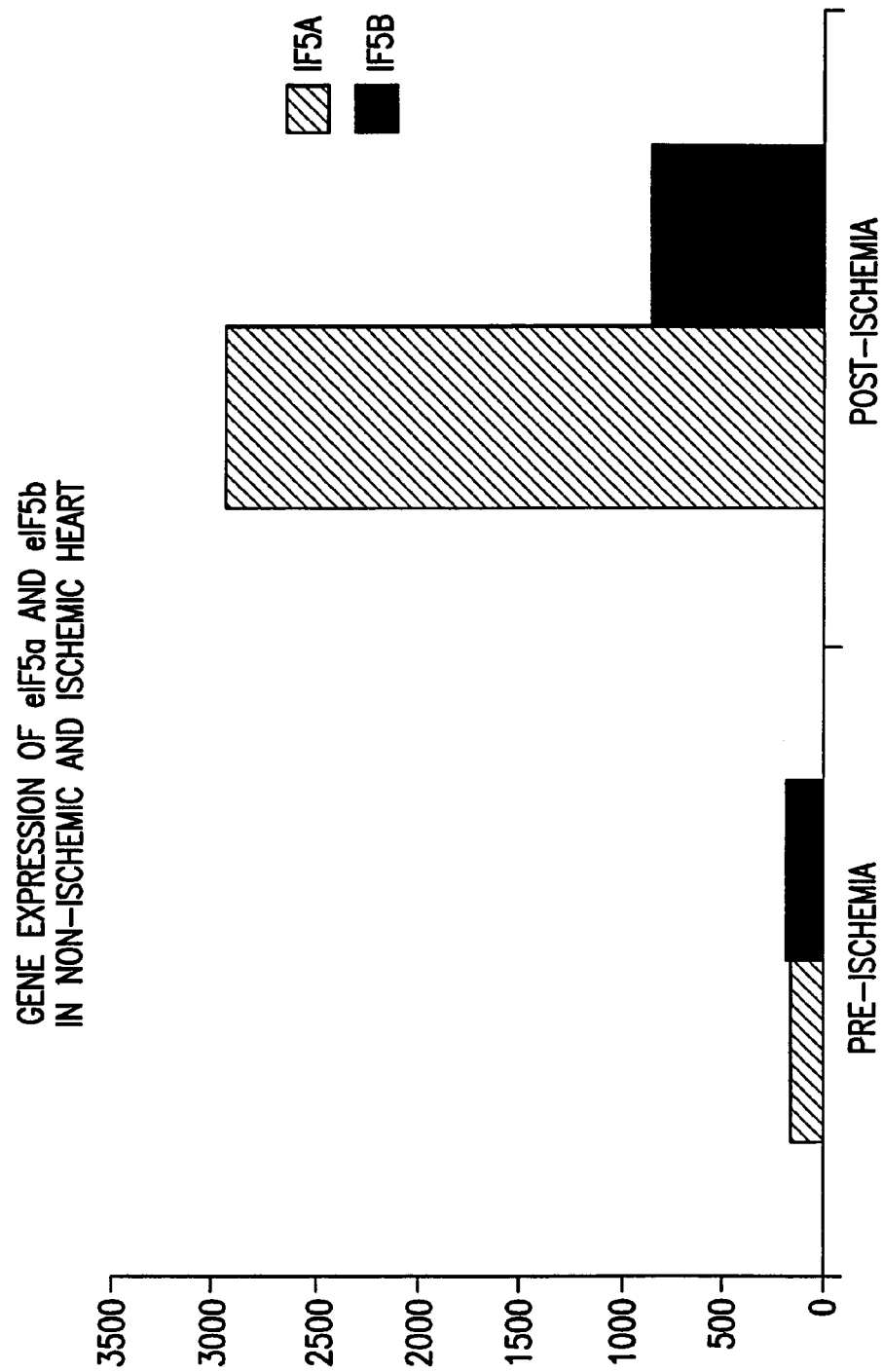
FIG. 46 is a bar graph showing the gene expression levels measured by real-time PCR of apoptosis-specific eIF-5A (eIf5a) versus proliferation eIF-5A (eIF5b) in pre-ischemia heart tissue and post ischemia heart tissue. The Y-axis is pg/ng of 18s (picograms of message RNA over nanograms of ribosomal RNA 18S).

FIG. 46 shows the results of an experiment where levels of apoptosis-specific eIF-5a (eIF5a) and proliferating eIF-5A (eIF5b) were measured before and after ischemia in heart tissue was induced. See also example 6. Before ischemia, the expression levels of apoptosis-specific eIF-5a (eIF5a) and proliferating eIF-5A (eIF5b) were roughly similar and were at low levels. After ischemia was induced, the level of apoptosis-specific eIF-5a (eIF5a) increases much more than the level of proliferating eIF-5A (eIF5b).

Knowing that the levels of expression of apoptosis-specific eIF-5a (eIF5a) and proliferating eIF-5A (eIF5b) are at relative low levels and are in relative balance with respect to each other in normal tissues, monitoring and detecting an increase in the gene expression level of apoptosis-specific eIF-5a (eIF5a) provides a method of diagnosing various diseases or conditions that place the cells or tissue in stress, such as ischemia.

Further, by being able to detect these conditions by measuring the levels of gene expression, there is provided methods of treating such conditions. For example, if ischemia is detected in the heart by either methods known in the art or by detecting an increase in levels of apoptosis-specific eIF-5a (eIF5a) gene expression, agents that would inhibit or decrease the levels of gene expression may be provided and thus decrease the incidence of cell death.

The agents that inhibit or decrease levels of gene expression of apoptosis-specific eIF-5a (eIF5a) are discussed herein above, including the use of antisense oligonucleotides to the apoptosis-specific eIF-5a (eIF5a). A preferred antisense oligonucleotide comprises an oligonucleotide complementary to the coding strand of a nucleotide sequence encoding an apoptosis-specific eIF-5a, such as but not limited to, the nucleotide sequences listed as SEQ ID NO: 3 or 4.

In some cancer cells, the normal regulatory mechanisms go awry and the amount of apoptosis-specific eIF-5A relative to the amount of proliferating eEF-5A is altered (the levels of apoptosis-specific eIF-5A increase such that they are greater than the proliferating eIF-5A). This potentially allows for diagnosis of a cell as cancerous prior to any phenotypic changes in the cell.

In addition, in ischemic heart tissue, the amount of apoptosis-specific eIF-5A relative to the amount of proliferating eIF-5A is altered so that the levels of apoptosis-specific eIF-5A are increased relative to the amount of proliferating eIF-5A.

In yet another embodiment, the ratio of proliferating eIF-5A to apoptosis-specific eIF-5A can be used in drug screening. Such a method also involves comparing the amount of proliferating eIF-5A present in a given cell with the amount of apoptosis-specific eIF-5A present in the same cell. The normal ratio of proliferating eIF-5A to apoptosis-specific eIF-5A would be compared to the ratio of proliferating eIF-5A to apoptosis-specific eIF-5A after contacting the cell with the drug candidate. Alterations in the ratio of proliferating eIF-5A to apoptosis-specific eIF-5A after contact allows for identification of those candidates that have apoptosis-modulating activity. Candidates having apoptosis-modulating activity can be useful in treating diseases associated with apoptosis, either through inhibition or induction of apoptosis. In addition, alterations in the ratio of proliferating eIF-5A to apoptosis-specific eIF-5A can be used to modulate apoptosis, which may also be useful to treat any of the conditions described herein as relating to abnormal apoptosis.

Using this method a large number of potential candidates, i.e., a library can be effectively screened to identify members of the library that modulate apoptosis. Any candidate or library of candidates can be screened using this method. For example, biological response modifiers that have shown promise as apoptosis modulators, including monoclonal antibodies that alter signal transduction pathways, cytokines such as TRAIL (Apo2 ligand), ligands for retinoid/steroid family nuclear receptors, and small-molecule compounds that bind and inhibit protein kinases, can be screened for definite apoptosis-modulating activity using the present methods.

One suitable candidate is a protein kinase C-alpha antisense oligonucleotide, ISIS 3521 (ISIS Pharmaceuticals, Inc., Carlsbad, Calif.), which has anti-tumor activity. Other specific candidates include caspases (Idun Pharmaceuticals, San Diego, Calif.), which are known to play a crucial role in the triggering and execution of apoptosis in a variety of cell types leading to cancer and neurodegenerative diseases; GENASENS™ (Genta, Inc., Berkeley Heights, N.J.), which is an antisense drug that blocks the production of Bcl-2; INGN 241 (Introgen Therapeutics, Inc., Houston, Tex.), which is a gene therapy targeting P53; rituximab (IDEC Corporation, Osaka, Japan), which is an anti-CD20 monoclonal antibody; and general apoptosis driven therapies for cardiovascular disease and cancer (AEgera Therapeutics Inc., Quebec, Canada).

It is understood that the nucleic acids and polypeptides of the present invention, where used in an animal for the purpose of prophylaxis or treatment, will be administered in the form of a composition additionally comprising a pharmaceutically acceptable carrier. Suitable pharmaceutically acceptable carriers include, for example, one or more of water, saline, phosphate buffered saline, dextrose, glycerol, ethanol and the like, as well as combinations thereof. Pharmaceutically acceptable carriers can further comprise minor amounts of auxiliary substances such as wetting or emulsifying agents, preservatives or buffers, which enhance the shelf life or effectiveness of the binding proteins. The compositions of the injection can, as is well known in the art, be formulated so as to provide quick, sustained or delayed release of the active ingredient after administration to the mammal.

The compositions of this invention can be in a variety of forms. These include, for example, solid, semi-solid and liquid dosage forms, such as tablets, pills, powders, liquid solutions, dispersions or suspensions, liposomes, suppositories, injectable and infusible solutions. The preferred form depends on the intended mode of administration and therapeutic application.

Such compositions can be prepared in a manner well known in the pharmaceutical art. In making the composition the active ingredient will usually be mixed with a carrier, or diluted by a carrier, and/or enclosed within a carrier which can, for example, be in the form of a capsule, sachet, paper or other container. When the carrier serves as a diluent, it can be a solid, semi-solid, or liquid material, which acts as a vehicle, excipient or medium for the active ingredient. Thus, the composition can be in the form of tablets, lozenges, sachets, cachets, elixirs, suspensions, aerosols (as a solid or in a liquid medium), ointments containing for example up to 10% by weight of the active compound, soft and hard gelatin capsules, suppositories, injection solutions, suspensions, sterile packaged powders and as a topical patch.

Having now generally described the invention, the same will be more readily understood through reference to the following examples, which are provided by way of illustration. The Examples are set forth to aid in understanding the invention but are not intended to, and should not be construed to, limit its scope in any way. The examples do not include detailed descriptions of conventional methods. Such methods are well known to those of ordinary skill in the art and are described in numerous publications. Detailed descriptions of conventional methods, such as those employed in the construction of vectors and plasmids, the insertion of nucleic acids encoding polypeptides into such vectors and plasmids, the introduction of plasmids into host cells, and the expression and determination thereof of genes and gene products can be obtained from numerous publication, including Sambrook, J. et al., (1989) Molecular Cloning: A Laboratory Manual, $2^{nd}$ ed., Cold Spring Harbor Laboratory Press. All references mentioned herein are incorporated in their entirety.

EXAMPLES

Example 1

The present example demonstrates isolation and characterization of a full-length cDNA encoding a rat eIF-5A nucleic acid exhibiting apoptosis-specific expression.

Superovulation and Induction of Apoptosis in Rat Corpus Luteum

Immature (21-30 day old) female rats were superovulated by subcutaneous injection with 50 IU of PMSG (Pregant Mare Serum Gonadotropin) and 60 to 65 hours later with 50 IU of HCG (Human Chorionic Gonadotropin). Seven days after the treatment with HCG, corpus luteum apoptosis was induced by subcutaneous injection with 500 mg of PGF-2α. Rats were sacrificed at various times (e.g., 1, 8, and 24 hours) after PGF-2α treatment, and the corpora lutea were removed and placed in liquid nitrogen. Control corpus luteum tissue was obtained by sacrificing rats immediately before PGF-2α treatment.

Dispersion of Rat Ovarian Corpus Luteum Cells

Six to nine days after superovulation, rats were treated by multisite subcutaneous injection with 500 mg PGF-2α. Fifteen to thirty minutes later, the ovaries were removed from the superovulated rats, placed in EBSS (Gibco) on ice, blotted dry and weighed. Connective tissue was trimmed away, and the ovaries were minced finely with a razor blade and washed twice with EBSS 2×. Collagenase solution was prepared by vortexing 6.5 mg of collagenase (Sigma, Catologue # C 5138) in 5 ml of EBSS. Minced tissue from 8 ovaries was added to 5 ml of collagenase in EBSS in a 50 ml Erlenmeyer flask and agitated gently by withdrawing several times into a Diamed pipette. The flask with minced tissue was then placed in a water bath at 37° C. for 20 minutes with gentle shaking (Position 45 on GFL incubator) under 95% air, 5% $CO_2$.

Following this incubation, the flask was placed on ice, and the suspension of cells was transferred with a plastic transfer pipet onto a Nitex filter fitted with Swiss Nitex Nylon Monofilament (75 m). The filtrate was collected into a 15 ml Falcon test tube. A second aliquot (2.5 ml) of collagenase solution (6.5 mg collagenase/5 ml EBSS) was added to the minced tissue remaining in the 50 ml Erlenmeyer flask, agitated gently using a pipette, incubated for 10 minutes and filtered as above. The two filtrates were combined and centrifuged in a clinical centrifuge (~200 g) for 5 minutes at room temperature. All but 2 ml of the supernatant were removed with a pipet and discarded, and the sedimented cells were resuspended in the remaining 2 ml of supernatant.

The cells were washed twice by adding 5 ml of MEM and centrifuging and resuspending as above. The washed cells were resuspended in 30 mls of MEM containing 10 mm glutamine in a 50 ml Erlenmeyer flask and incubated for 1 hour without shaking at 37° C. under 95% air, 5% $CO_2$. The cells were then sedimented by centrifugation as above and resuspended in MEM containing 10 mM glutamine.

The concentration of dispersed cells was determined using a hemocytometer, and viability was assessed using trypan blue dye. Aliquots of $2-5 \times 10^5$ cells were placed in 12×75 mm test tubes and incubated without shaking for 2-5 hours at 37° C. under 95% air, 5% $CO_2$. The progress of apoptosis during this period was monitored by assessing the degree of DNA laddering.

Visualization of Apoptosis in Rat Corpus Luteum by DNA Laddering

The degree of apoptosis was determined by DNA laddering. Genomic DNA was isolated from dispersed corpus luteal cells or from excised corpus luteum tissue using the QIAamp DNA Blood Kit (Qiagen) according to the manufacturer's instructions. Corpus luteum tissue was excised before the induction of apoptosis by treatment with PGF-2α, 1 and 24 hours after induction of apoptosis. The isolated DNA was end-labeled by incubating 500 ng of DNA with 0.2 µCi [α-$^{32}$P]dCTP, 1 mM Tris, 0.5 mM EDTA, 3 units of Klenow enzyme, and 0.2 µM each of dATP, dGTP, and dTTP at room temperature for 30 minutes. Unincorporated nucleotides were removed by passing the sample through a 1 ml Sepadex G-50 column according to Sambrook et al. The samples were then resolved by Tris-acetate-EDTA (1.8%) gel electrophoresis. The gel was dried for 30 minutes at room temperature under vacuum and exposed to x-ray film at −80° C. for 24 hours.

Figure 16:
FIG. 16 depicts a DNA laddering experiment in which the degree of apoptosis in superovulated rat corpus lutea was examined after injection with PGF-2α.

In one experiment, the degree of apoptosis in superovulated rat corpus lutea was examined either 0, 1, or 24 hours after injection with PGF-2α. In the 0 hour control, the ovaries were removed without PGF-2α injection. Laddering of low molecular weight DNA fragments reflecting nuclease activity associated with apoptosis is not evident in control corpus luteum tissue excised before treatment with PGF-2α, but is discernible within 1 hour after induction of apoptosis and is pronounced by 24 hours after induction of apoptosis, which is shown in FIG. 16. In this figure, the top panel is an autoradiograph of the Northern blot probed with the $^{32}$P-dCTP-labeled 3'-untranslated region of rat corpus luteum apoptosis-specific DHS cDNA. The lower panel is the ethidium bromide stained gel of total RNA. Each lane contains 10 μg RNA. The data indicate that there is down-regulation of eIF-5A transcript following serum withdrawal.

Figure 17:
FIG. 17 is an agarose gel of genomic DNA isolated from apoptosing rat corpus luteum showing DNA laddering after treatment of rats with PGF-2α.

In another experiment, the corresponding control animals were treated with saline instead of PGF-2α. Fifteen minutes after treatment with saline or PGF-2α, corpora lutea were removed from the animals. Genomic DNA was isolated from the corpora lutea at 3 hours and 6 hours after removal of the tissue from the animals. DNA laddering and increased end labeling of genomic DNA are evident 6 hours after removal of the tissue from the PGF-2α-treated animals, but not at 3 hours after removal of the tissue. See FIG. 17. DNA laddering reflecting apoptosis is also evident when corpora lutea are excised 15 minutes after treatment with PGF-2α and maintained for 6 hours under in vitro conditions in EBSS (Gibco). Nuclease activity associated with apoptosis is also evident from more extensive end labeling of genomic DNA.

In another experiment, superovulation was induced by subcutaneous injection with 500 μg of PGF-2α. Control rats were treated with an equivalent volume of saline solution. Fifteen to thirty minutes later, the ovaries were removed and minced with collagenase. The dispersed cells from rats treated with PGF-2α were incubated in 10 mm glutamine+10 mm spermidine for 1 hour and for a further 5 hours in 10 mm glutamine without spermidine (lane 2) or in 10 mm glutamine+10 mm spermidine for 1 hour and for a further 5 hours in 10 mm glutamine+1 mm spermidine (lane 3). Control cells from rats treated with saline were dispersed with collagenase and incubated for 1 hour and a further 5 hours in glutamine only (lane 1). Five hundred nanograms of DNA from each sample was labeled with [α-$^{32}$P]-dCTP using klenow enzyme, separated on a 1.8% agarose gel, and exposed to film for 24 hours. Results are shown in FIG. 18.

In yet another experiment, superovulated rats were injected subcutaneously with 1 mg/100 g body weight of spermidine, delivered in three equal doses of 0.333 mg/100 g body weight, 24, 12, and 2 hours prior to a subcutaneous injection with 500 μg PGF-2α. Control rats were divided into three sets: no injections, three injections of spermidine but no PGF-2α; and three injections with an equivalent volume of saline prior to PGF-2α treatment. Ovaries were removed front the rats either 1 hour and 35 minutes or 3 hours and 45 minutes after prostaglandin treatment and used for the isolation of DNA. Five hundred nanograms of DNA from each sample was labeled with [α-$^{32}$P]-dCTP using Klenow enzyme, separated on a 1.8% agarose gel, and exposed to film for 24 hours: lane 1, no injections (animals were sacrificed at the same time as for lanes 3-5); lane 2, three injections with spermidine (animals were sacrificed at the same time as for lanes 3-5); lane 3, three injections with saline followed by injection with PGF-2α (animals were sacrificed 1 h and 35 min after treatment with PGF-2a); lane 4, three injections with spermidine followed by injection with PGF-2α (animals were sacrificed 1 h and 35 min after treatment with PGF-2α); lane 5, three injections with spermidine followed by injection with PGF-2α (animals were sacrificed 1 h and 35 min after treatment with PGF-2α); lane 6, three injections with spermidine followed by injection with PGF-2α (animals were sacrificed 3 h and 45 min after treatment with PGF-2α); lane 7, three injections with spermidine followed by injection with PGF-2α (animals were sacrificed 3 h and 45 min after treatment with PGF-2α). Results are shown in FIG. 19.

RNA Isolation

Total RNA was isolated from corpus luteum tissue removed from rats at various times after PGF-2α induction of apoptosis. Briefly, the tissue (5 g) was ground in liquid nitrogen. The ground powder was mixed with 30 ml guanidinium buffer (4 M guanidinium isothiocyanate, 2.5 mM NaOAc pH 8.5, 0.8% β-mercaptoethanol). The mixture was filtered through four layers of Miracloth and centrifuged at 10,000 g at 4° C. for 30 minutes. The supernatant was then subjected to cesium chloride density gradient centrifugation at 11,200 g for 20 hours. The pelleted RNA was rinsed with 75% ethanol, resuspended in 600 ml DEPC-treated water and the RNA precipitated at −70° C. with 1.5 ml 95% ethanol and 60 ml of 3M NaOAc.

Genomic DNA Isolation and Laddering

Genomic DNA was isolated from extracted corpus luteum tissue or dispersed corpus luteal cells using the QIAamp DNA Blood Kit (Qiagen) according to the manufacturer's instructions. The DNA was end-labeled by incubating 500 ng of DNA with 0.2 μCi [α-$^{32}$P]dCTP, 1 mM Tris, 0.5 mM EDTA, 3 units of Klenow enzyme, and 0.2 μM each of dATP, dGTP, and dTTP, at room temperature for 30 minutes. Unincorporated nucleotides were removed by passing the sample through a 1-ml Sephadex G-50 column according to the method described by Maniatis et al. The samples were then resolved by Tris-acetate-EDTA (2%) gel electrophoresis. The gel was dried for 30 minutes at room temperature under vacuum and exposed to x-ray film at −80° C. for 24 hours.

Plasmid DNA Isolation, DNA Sequencing

The alkaline lysis method described by Sambrook et al., supra, was used to isolate plasmid DNA. The full-length positive cDNA clone was sequenced using the dideoxy sequencing method. Sanger et al., Proc. Natl. Acad. Sci. USA, 74:5463-5467. The open reading frame was compiled and analyzed using BLAST search (GenBank, Bethesda, Md.) and sequence alignment was achieved using a BCM Search Launcher: Multiple Sequence Alignments Pattern-Induced Multiple Alignment Method (see F. Corpet, Nuc. Acids Res., 16:10881-10890, (1987). Sequences and sequence alignments are shown in FIGS. 5-11.

Northern Blot Hybridization of Rat Corpus Luteum RNA

Twenty milligrams of total RNA isolated from rat corpus luteum at various stages of apoptosis were separated on 1% denatured formaldehyde agarose gels and immobilized on nylon membranes. The full-length rat apoptosis-specific eIF-5A cDNA (SEQ ID NO:1) labeled with $^{32}$P-dCTP using a random primer kit (Boehringer) was used to probe the membranes 7×10$^7$. Alternatively, full length rat apoptosis-specific DHS cDNA (SEQ ID NO:6) labeled with $^{32}$P-dCTP using a random primer kit (Boehringer) was used to probe the membranes (7×10⁷ cpm). The membranes were washed once with 1×SSC, 0.1% SDS at room temperature and three times with 0.2×SSC, 0.1% SDS at 65° C. The membranes were dried and exposed to X-ray film overnight at −70° C.

Figure 14:
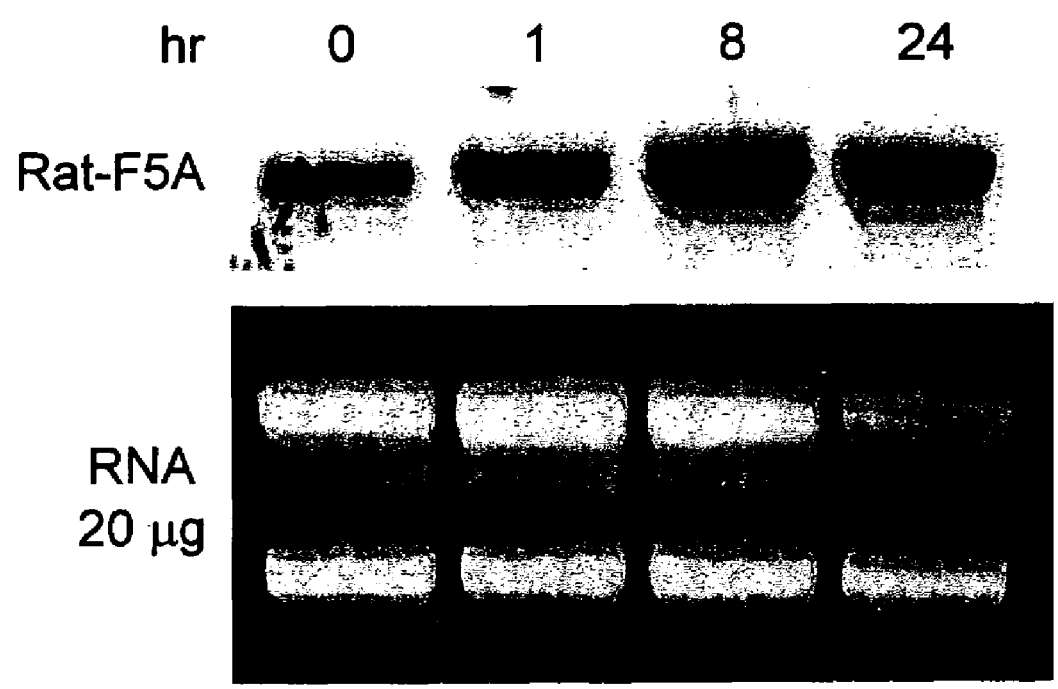
FIG. 14 is a Northern blot (FIG. 14A) and an ethidium bromide stained gel (FIG. 14B) of total RNA probed with the $^{32}$P-dCTP-labeled 3'-end of rat corpus luteum apoptosis-specific eIF-5A cDNA.
Figure 15:
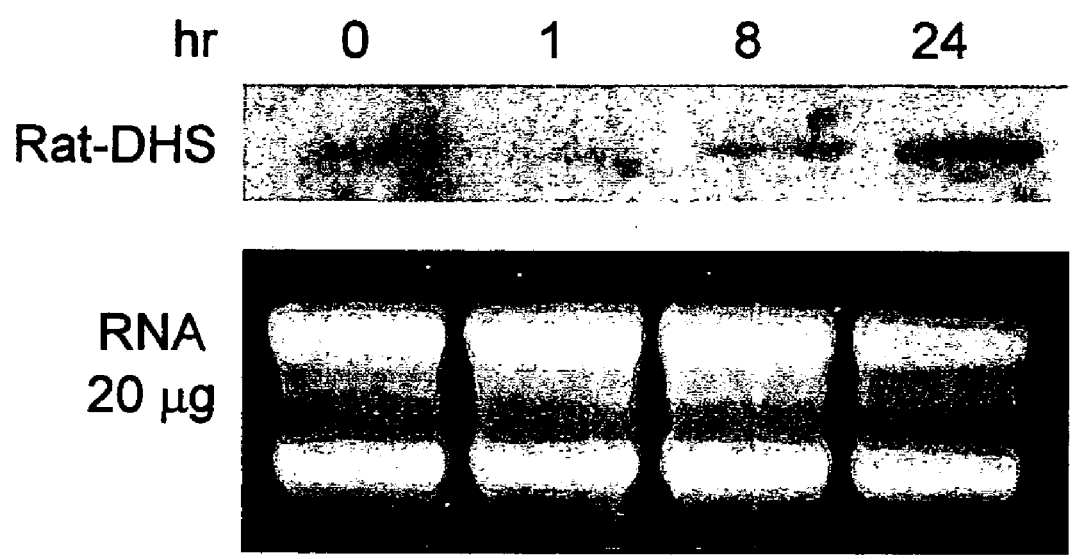
FIG. 15 is a Northern blot (FIG. 15A) and an ethidium bromide stained gel (FIG. 15B) of total RNA probed with the $^{32}$P-dCTP-labeled 3'-end of rat corpus luteum apoptosis-specific DHS cDNA.

As can be seen, eIF-5A and DHS are both upregulated in apoptosing corpus luteum tissue. Expression of apoptosis-specific eIF-5A is significantly enhanced after induction of apoptosis by treatment with PGF-2α—low at time zero, increased substantially within 1 hour of treatment, increased still more within 8 hours of treatment and increased slightly within 24 hours of treatment (FIG. 14). Expression of DHS was low at time zero, increased substantially within 1 hour of treatment, increased still more within 8 hours of treatment and increased again slightly within 24 hours of treatment (FIG. 15).

Generation of an Apoptosing Rat Corpus Luteum RT-PCR Product Using Primers Based on Yeast, Fungal and Human eIF-5A Sequences A partial-length apoptosis-specific eIF-5A sequence (SEQ ID NO:11) corresponding to the 3' end of the gene was generated from apoptosing rat corpus luteum RNA template by RT-PCR using a pair of oligonucleotide primers designed from yeast, fungal and human eIF-5A sequences. The upstream primer used to isolate the 3' end of the rat eIF-5A gene is a 20 nucleotide degenerate primer: 5' TCSAARACHGGNAAGCAYGG 3' (SEQ ID NO:9), wherein S is selected from C and G; R is selected from A and G; H is selected from A, T, and C; Y is selected from C and T; and N is any nucleic acid. The downstream primer used to isolate the 3' end of the rat eIF-5A gene contains 42 nucleotides: 5' GCGAAGCTTCCATGG CTCGAGTTTTTTTTTTTTTTTTTTTTTT 3' (SEQ ID NO:10). A reverse transcriptase polymerase chain reaction (RT-PCR) was carried out. Briefly, using 5 mg of the downstream primer, a first strand of cDNA was synthesized. The first strand was then used as a template in a RT-PCR using both the upstream and downstream primers.

Separation of the RT-PCR products on an agarose gel revealed the presence a 900 bp fragment, which was subcloned into pBluescript™ (Stratagene Cloning Systems, LaJolla, Calif.) using blunt end ligation and sequenced (SEQ ID NO:11). The cDNA sequence of the 3' end is SEQ ID NO:11 and the amino acid sequence of the 3' end is SEQ ID NO:12. See FIGS. 1-2.

A partial-length apoptosis-specific eIF-5A sequence (SEQ ID NO:15) corresponding to the 5' end of the gene and overlapping with the 3' end was generated from apoptosing rat corpus luteum RNA template by RT-PCR. The 5' primer is a 24-mer having the sequence, 5' CAGGTCTAGAGTTG-GAATCGAAGC 3' (SEQ ID NO:13), that was designed from human eIF-5A sequences. The 3' primer is a 30-mer having the sequence, 5' ATATCTCGAGCCTT GATTG-CAACAGCTGCC 3' (SEQ ID NO:14) that was designed according to the 3' end RT-PCR fragment. A reverse transcriptase-polymerase chain reaction (RT-PCR) was carried out. Briefly, using 5 mg of the downstream primer, a first strand of cDNA was synthesized. The first strand was then used as a template in a RT-PCR using both the upstream and downstream primers.

Separation of the RT-PCR products on an agarose gel revealed the presence a 500 bp fragment, which was subcloned into pBluescript™ (Stratagene Cloning Systems, LaJolla, Calif.) using XbaI and XhoI cloning sites present in the upstream and downstream primers, respectively, and sequenced (SEQ ID NO: 15). The cDNA sequence of the 5' end is SEQ ID NO:15, and the amino acid sequence of the 5' end is SEQ ID NO:16. See FIG. 2.

The sequences of the 3' and 5' ends of the rat apoptosis-specific eIF-5A (SEQ ID NO:11 and SEQ ID NO: 15, respectively) overlapped and gave rise to the full-length cDNA sequence (SEQ ID NO:1). This full-length sequence was aligned and compared with sequences in the GeneBank data base. See FIGS. 1-3. The cDNA clone encodes a 154 amino acid polypeptide (SEQ ID NO:2) having a calculated molecular mass of 16.8 KDa. The nucleotide sequence, SEQ ID NO:1, for the full length cDNA of the rat apoptosis-specific corpus luteum eIF-5A gene obtained by RT-PCR is depicted in FIG. 3 and the corresponding derived amino acid sequence is SEQ ID NO:2. The derived full-length amino acid sequence of eIF-5A was aligned with human and mouse eIF-5a sequences. See FIGS. 8-10.

Generation of an Apoptosing Rat Corpus Luteum RT-PCR Product Using Primers Based on a Human DHS Sequence A partial-length apoptosis-specific DHS sequence (SEQ ID NO:6) corresponding to the 3' end of the gene was generated from apoptosing rat corpus luteum RNA template by RT-PCR using a pair of oligonucleotide primers designed from a human DHS sequence. The 5' primer is a 20-mer having the sequence, 5' GTCTGTGTATTATTGGGCCC 3' (SEQ ID NO. 17); the 3' primer is a 42-mer having the sequence, 5' GCGAAGCTTCCATGGC TCGAGTTTTTTTTTTTTTTTTTTTTTT 3' (SEQ ID NO:18). A reverse transcriptase polymerase chain reaction (RT-PCR) was carried out. Briefly, using 5 mg of the downstream primer, a first strand of cDNA was synthesized. The first strand was then used as a template in a RT-PCR using both the upstream and downstream primers.

Separation of the RT-PCR products on an agarose gel revealed the presence a 606 bp fragment, which was subcloned into pBluescript™ (Stratagene Cloning Systems, LaJolla, Calif.) using blunt end ligation and sequenced (SEQ ID NO:6). The nucleotide sequence (SEQ ID NO:6) for the partial length cDNA of the rat apoptosis-specific corpus luteum DHS gene obtained by RT-PCR is depicted in FIG. 4 and the corresponding derived amino acid sequence is SEQ ID NO:7.

Isolation of Genomic DNA and Southern Analysis

Genomic DNA for southern blotting was isolated from excised rat ovaries. Approximately 100 mg of ovary tissue was divided into small pieces and placed into a 15 ml tube. The tissue was washed twice with 1 ml of PBS by gently shaking the tissue suspension and then removing the PBS using a pipette. The tissue was resuspended in 2.06 ml of DNA-buffer (0.2 M Tris-HCl pH 8.0 and 0.1 mM EDTA) and 240 µl of 10% SDS and 100 µl of proteinase K (Boehringer Manheim; 10 mg/ml) was added. The tissue was placed in a shaking water bath at 45° C. overnight. The following day another 100 µl of proteinase K (10 mg/ml) was added and the tissue suspension was incubated in a water-bath at 45° C. for an additional 4 hours. After the incubation the tissue suspension was extracted once with an equal volume of phenol:chloroform:iso-amyl alcohol (25:24:1) and once with an equal volume of chloroform:iso-amyl alcohol (24:1). Following the extractions ¹⁄₁₀th volume of 3M sodium acetate (pH 5.2) and 2 volumes of ethanol were added. A glass pipette sealed and formed into a hook using a Bunsen burner was used to pull the DNA threads out of solution and to transfer the DNA into a clean microcentrifuge tube. The DNA was washed once in 70% ethanol and air-dried for 10 minutes. The DNA pellet was dissolved in 500 µl of 10 mM Tris-HCl (pH 8.0), 10 µl of RNase A (10 mg/ml) was added, and the DNA was incubated for 1 hour at 37° C. The DNA was extracted once with phenol:chloroform:iso-amyl alcohol (25:24:1) and the DNA was precipitated by adding 1/10th volume of 3 M sodium acetate (pH 5.2) and 2 volumes of ethanol. The DNA was pelleted by centrifugation for 10 minutes at 13,000×g at 4° C. The DNA pellet was washed once in 70% ethanol and dissolved in 200 µl 10 mM Tris-HCl (pH 8.0) by rotating the DNA at 4° C. overnight.

For Southern blot analysis, genomic DNA isolated from rat ovaries was digested with various restriction enzymes that either do not cut in the endogenous gene or cut only once. To achieve this, 10 µg genomic DNA, 20 µl 10× reaction buffer and 100 U restriction enzyme were reacted for five to six hours in a total reaction volume of 200 µl. Digested DNA was loaded onto a 0.7% agarose gel and subjected to electrophoresis for 6 hours at 40 volts or overnight at 15 volts. After electrophoresis, the gel was depurinated for 10 minutes in 0.2 N HCl followed by two 15-minute washes in denaturing solution (0.5 M NaOH, 1.5 M NaCl) and two 15 minute washes in neutralizing buffer (1.5 M NaCl, 0.5 M Tris-HCl pH 7.4). The DNA was transferred to a nylon membrane, and the membrane was prehybridized in hybridization solution (40% formamide, 6×SSC, 5× Denhart's, solution (1× Denhart's solution is 0.02% Ficoll, 0.02% PVP, and 0.02% BSA), 0.5% SDS, and 1.5 mg of denatured salmon sperm DNA). A 700 bp PCR fragment of the 3' UTR of rat eIF-5A cDNA (650 bp of 3' UTR and 50 bp of coding) was labeled with [$\alpha$-$^{32}$P]-dCTP by random priming and added to the membrane at 1×106 cpm/ml.

Similarly, a 606 bp PCR fragment of the rat DHS cDNA (450 bp coding and 156 bp 3' UTR) was random prime labeled with [$\alpha$-$^{32}$P]-dCTP and added at 1×10 6 cpm/ml to a second identical membrane. The blots were hybridized overnight at 42° C. and then washed twice with 2×SSC and 0.1% SDS at 42° C. and twice with 1×SSC and 0.1% SDS at 42° C. The blots were then exposed to film for 3-10 days.

Figure 20:
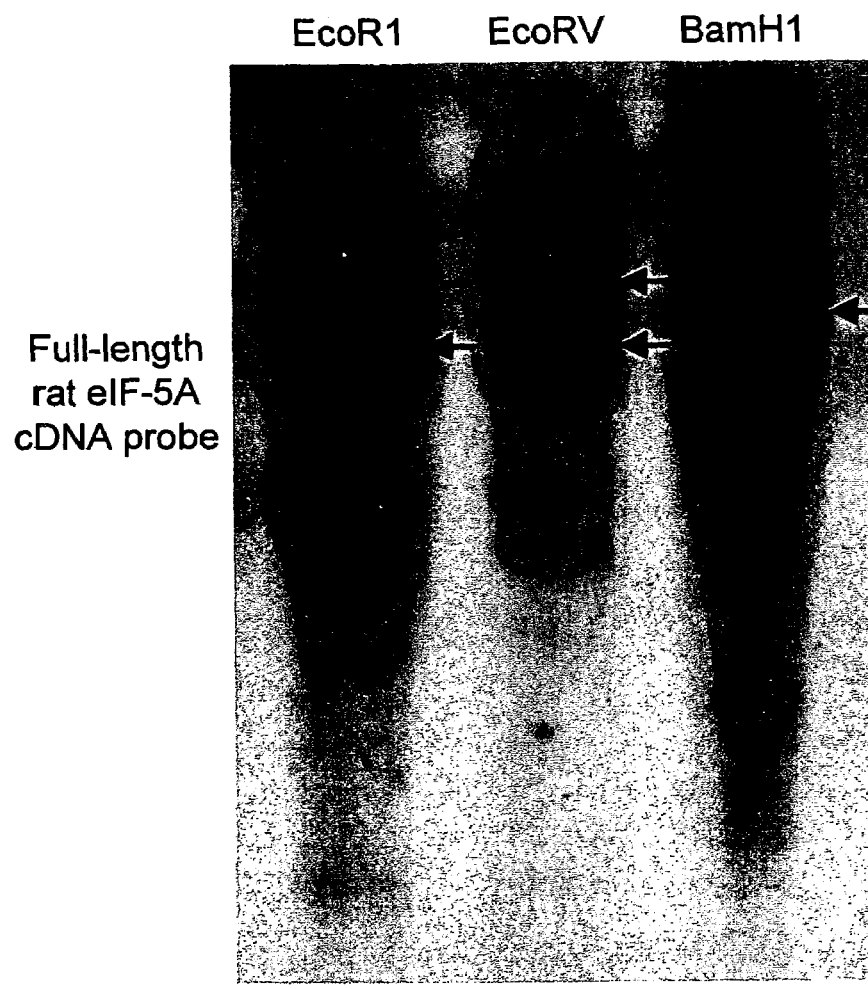
FIG. 20 is a Southern blot of rat genomic DNA probed with $^{32}$P-dCTP-labeled partial-length rat corpus luteum apoptosis-specific eIF-5A cDNA.

Rat corpus genomic DNA was cut with restriction enzymes as indicated on FIG. 20 and probed with $^{32}$P-dCTP-labeled full-length eIF-5A cDNA. Hybridization under high stringency conditions revealed hybridization of the full-length cDNA probe to several restriction fragments for each restriction enzyme digested DNA sample, indicating the presence of several isoforms of eIF-5A. Of particular note, when rat genomic DNA was digested with EcoRV, which has a restriction site within the open reading frame of apoptosis-specific eIF-5A, two restriction fragments of the apoptosis-specific isoform of eIF-5A were detectable in the Southern blot. The two fragments are indicated with double arrows in FIG. 20. The restriction fragment corresponding to the apoptosis-specific isoform of eIF-5A is indicated by a single arrow in the lanes labeled EcoR1 and BamH1, restriction enzymes for which there are no cut sites within the open reading frame. These results suggest that the apoptosis-specific eIF-5A is a single copy gene in rat. As shown in FIGS. 5 through 13, the eIF-5A gene is highly conserved across species, and so it would be expected that there is a significant amount of conservation between isoforms within any species.

Figure 21:
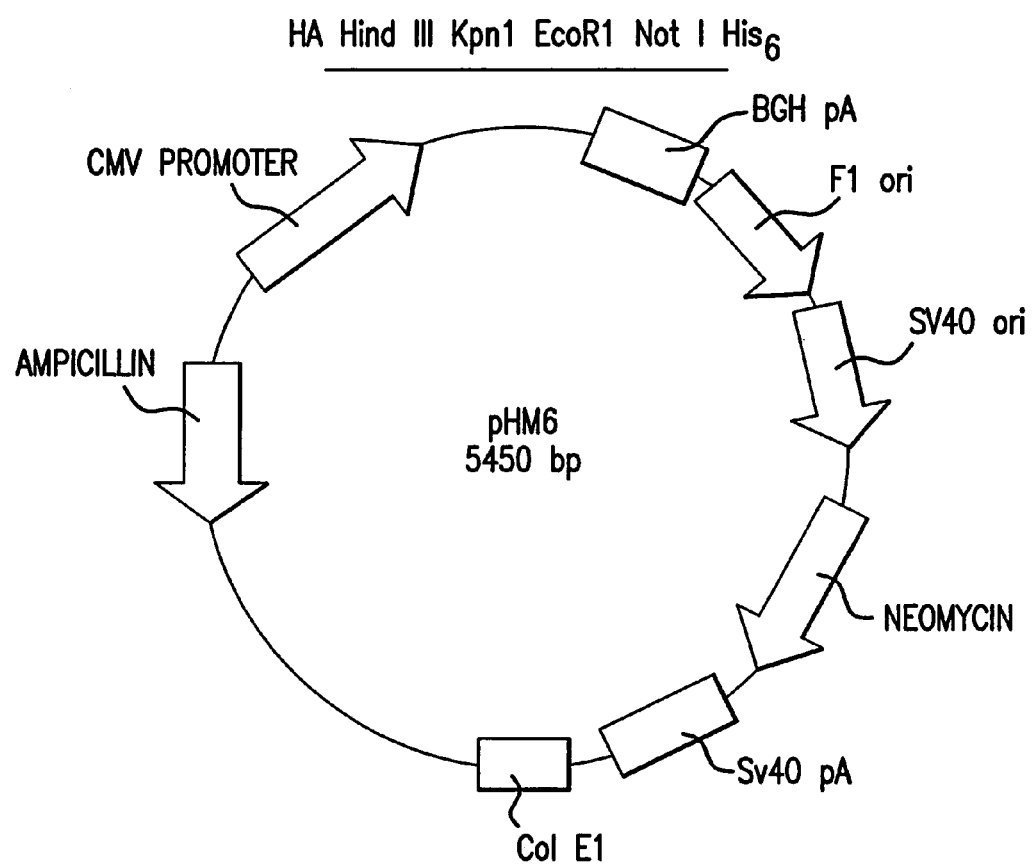
FIG. 21 depicts pHM6, a mammalian epitope tag expression vector (Roche Molecular Biochemicals).

FIG. 21 shows a Southern blot of rat genomic DNA probed with $^{32}$P-dCTP-labeled partial-length rat corpus luteum apoptosis-specific DHS cDNA. The genomic DNA was cut with EcoRV, a restriction enzyme that does not cut the partial-length cDNA used as a probe. Two restriction fragments are evident indicating that there are two copies of the gene or that the gene contains an intron with an EcoRV site.

Example 2

The present example demonstrates modulation of apoptosis with apoptosis-specific eIF-5A and DHS.

Culturing of COS-7 Cells and Isolation of RNA

COS-7, an African green monkey kidney fibroblast-like cell line transformed with a mutant of SV40 that codes for wild-type T antigen, was used for all transfection-based experiments. COS-7 cells were cultured in Dulbecco's Modified Eagle's medium (DMEM) with 0.584 grams per liter of L-glutamine, 4.5 g of glucose per liter, and 0.37% sodium bicarbonate. The culture media was supplemented with 10% fetal bovine serum (FBS) and 100 units of penicillin/streptomycin. The cells were grown at 37° C. in a humidified environment of 5% $CO_2$ and 95% air. The cells were subcultured every 3 to 4 days by detaching the adherent cells with a solution of 0.25% trypsin and 1 mM EDTA. The detached cells were dispensed at a split ratio of 1:10 in a new culture dish with fresh media.

COS-7 cells to be used for isolation of RNA were grown in 150-mm tissue culture treated dishes (Corning). The cells were harvested by detaching them with a solution of trypsin-EDTA. The detached cells were collected in a centrifuge tube, and the cells were pelleted by centrifugation at 3000 rpm for 5 minutes. The supernatant was removed, and the cell pellet was flash-frozen in liquid nitrogen. RNA was isolated from the frozen cells using the GenElute Mammalian Total RNA Miniprep kit (Sigma) according to the manufacturer's instructions.

Construction of Recombinant Plasmids and Transfection of COS-7 Cells

Recombinant plasmids carrying the full-length coding sequence of rat apoptosis eIF-5A in the sense orientation and the 3' untranslated region (UTR) of rat apoptosis eIF-5A in the antisense orientation were constructed using the mammalian epitope tag expression vector, pHM6 (Roche Molecular Biochemicals), which is illustrated in FIG. 21. The vector contains the following: CMV promoter—human cytomegalovirus immediate-early promoter/enhancer; HA—nonapeptide epitope tag from influenza hemagglutinin; BGH pA-Bovine growth hormone polyadenylation signal; f1 ori—f1 origin; SV40 ori —SV40 early promoter and origin; Neomycin—Neomycin resistance (G418) gene; SV40 pA —SV40 polyadenylation signal; Col E1—ColE1 origin; Ampicillin—Ampicillin resistance gene. The full-length coding sequence of rat apoptosis eIF-5A and the 3' UTR of rat apoptosis eIF-5A were amplified by PCR from the original rat eIF-5A RT-PCR fragment in pBluescript (SEQ ID NO: 1). To amplify the full-length eIF-5A the primers used were as follows: Forward 5' GCCAAGCT-TAATGGCAGATGATTT GG 3' (Hind3) (SEQ ID NO:22) and Reverse 5' CTGAATTCCAGT TATTTTGCCATGG 3' (EcoR1) (SEQ ID NO:23). To amplify the 3' UTR rat eIF-5A the primers used were as follows: forward 5' AATGAAT-TCCGCCATGACAGAGGAGGC 3' (EcoR1) (SEQ ID NO:24) and reverse 5' GCGAAGCTTCCATGGCTC-GAGTTTTTTTTTTTTTTTTTTTT 3' (Hind3) (SEQ ID NO:18).

The full-length rat eIF-5A PCR product isolated after agarose gel electrophoresis was 430 bp in length while the 3' UTR rat eIF-5A PCR product was 697 bp in length. Both PCR products were subcloned into the Hind 3 and EcoR1 sites of pHM6 to create pHM6-full-length eIF-5A and pHM6-antisense 3'UTReIF-5A. The full-length rat eIF-5A PCR product was subcloned in frame with the nonapeptide epitope tag from influenza hemagglutinin (HA) present upstream of the multiple cloning site to allow for detection of the recombinant protein using an anti-[HA]-peroxidase antibody. Expression is driven by the human cytomegalovirus immediate-early promoter/enhancer to ensure high level expression in mammalian cell lines. The plasmid also features a neomycin-resistance (G418) gene, which allows for selection of stable transfectants, and a SV40 early promoter and origin, which allows episomal replication in cells expressing SV40 large T antigen, such as COS-7.

COS-7 cells to be used in transfection experiments were cultured in either 24 well cell culture plates (Corning) for cells to be used for protein extraction, or 4 chamber culture slides (Falcon) for cells to be used for staining. The cells were grown in DMEM media supplemented with 10% FBS, but lacking penicillin/streptomycin, to 50 to 70% confluency. Transfection medium sufficient for one well of a 24-well plate or culture slide was prepared by diluting 0.32 µg of plasmid DNA in 42.5 µl of serum-free DMEM and incubating the mixture at room temperature for 15 minutes. 1.6 µl of the transfection reagent, LipofectAMINE (Gibco, BRL), was diluted in 42.5 µl of serum-free DMEM and incubated for 5 minutes at room temperature. After 5 minutes the LipofectAMINE mixture was added to the DNA mixture and incubated together at room temperature for 30 to 60 minutes. The cells to be transfected were washed once with serum-free DMEM before overlaying the transfection medium and the cells were placed back in the growth chamber for 4 hours.

After the incubation, 0.17 ml of DMEM+20% FBS was added to the cells. The cells were the cultured for a further 40 hours before either being induced to undergo apoptosis prior to staining or harvested for Western blot analysis. As a control, mock transfections were also performed in which the plasmid DNA was omitted from the transfection medium.

Protein Extraction and Western Blotting

Protein was isolated for Western blotting from transfected cells by washing the cells twice in PBS (8 g/L NaCl, 0.2 g/L KCl, 1.44 g/L $Na_2HPO_4$, and 0.24 g/L $KH_2PO_4$) and then adding 150 pt of hot SDS gel-loading buffer (50 mM Tris-HCl pH 6.8, 100 mM dithiothreitol, 2% SDS, 0.1% bromophenol blue, and 10% glycerol). The cell lysate was collected in a microcentriflige tube, heated at 95° C. for 10 minutes, and then centrifuged at 13,000×g for 10 minutes. The supernatant was transferred to a fresh microcentriftige tube and stored at −20° C. until ready for use.

For Western blotting, 2.5 or 5 µg of total protein was separated on a 12% SDS-polyacrylamide gel. The separated proteins were transferred to a polyvinylidene difluoride membrane. The membrane was then incubated for one hour in blocking solution (5% skim milk powder, 0.02% sodium azide in PBS) and washed three times for 15 minutes in PBS-T (PBS+0.05% Tween-20). The membrane was stored overnight in PBS-T at 4° C. After being warmed to room temperature the next day, the membrane was blocked for 30 seconds in 1 µg/ml polyvinyl alcohol. The membrane was rinsed 5 times in deionized water and then blocked for 30 minutes in a solution of 5% milk in PBS. The primary antibody was preincubated for 30 minutes in a solution of 5% milk in PBS prior to incubation with the membrane.

Several primary antibodies were used. An anti-[HA]-peroxidase antibody (Roche Molecular Biochemicals) was used at a dilution of 1:5000 to detect expression of the recombinant proteins. Since this antibody is conjugated to peroxidase, no secondary antibody was necessary, and the blot was washed and developed by chemiluminescence. The other primary antibodies that were used are monoclonal antibodies from Oncogene that recognize p53 (Ab-6), Bcl-2 (Ab-1), and c-Myc (Ab-2). The monoclonal antibody to p53 was used at a dilution of 0.1 µg/ml, and the monoclonal antibodies to Bcl-2 and c-Myc were both used at a dilution of 0.83 µg/ml. After incubation with primary antibody for 60 to 90 minutes, the membrane was washed 3 times for 15 minutes in PBS-T. Secondary antibody was then diluted in 1% milk in PBS and incubated with the membrane for 60 to 90 minutes. When p53 (Ab-6) was used as the primary antibody, the secondary antibody used was a goat anti-mouse IgG conjugated to alkaline phosphatase (Rockland) at a dilution of 1:1000. When Bcl-2 (Ab-1) and c-Myc (Ab-2) were used as the primary antibody, a rabbit anti-mouse IgG conjugated to peroxidase (Sigma) was used at a dilution of 1:5000. After incubation with the secondary antibody, the membrane was washed 3 times in PBS-T.

Two detection methods were used to develop the blots, a colorimetric method and a chemiluminescent method. The colorimetric method was used only when p53 (Ab-6) was used as the primary antibody in conjunction with the alkaline phosphatase-conjugated secondary antibody. Bound antibody was visualized by incubating the blot in the dark in a solution of 0.33 mg/mL nitro blue tetrazolium, 0.165 mg/mL 5-bromo-4-chloro-3-indolyl phosphate, 100 mM NaCl, 5 mM $MgCl_2$, and 100 mM Tris-HCl (pH 9.5). The color reaction was stopped by incubating the blot in 2 mM EDTA in PBS. A chemiluminescent detection method was used for all other primary antibodies, including anti-[HA]-peroxidase, Bcl-2 (Ab-1), and c-Myc (Ab-2). The ECL Plus Western blotting detection kit (Amersham Pharmacia Biotech) was used to detect peroxidase-conjugated bound antibodies. In brief, the membrane was lightly blotted dry and then incubated in the dark with a 40:1 mix of reagent A and reagent B for 5 minutes. The membrane was blotted dry, placed between sheets of acetate, and exposed to X-ray film for time periods varying from 10 seconds to 10 minutes.

Induction of Apoptosis in COS 7 Cells

Two methods were used to induce apoptosis in transfected COS-7 cells, serum deprivation and treatment with Actinomycin D, *streptomyces* sp (Calbiochem). For both treatments, the medium was removed 40 hours post-transfection. For serum starvation experiments, the media was replaced with serum- and antibiotic-free DMEM. Cells grown in antibiotic-free DMEM supplemented with 10% FBS were used as a control. For Actinomycin D induction of apoptosis, the media was replaced with antibiotic-free DMEM supplemented with 10% FBS and 1 µg/ml Actinomycin D dissolved in methanol. Control cells were grown in antibiotic-free DMEM supplemented with 10% FBS and an equivalent volume of methanol. For both methods, the percentage of apoptotic cells was determined 48 hours later by staining with either Hoescht or Annexin V-Cy3. Induction of apoptosis was also confirmed by Northern blot analyses, as shown in FIG. 22.

Hoescht Staining

The nuclear stain, Hoescht, was used to label the nuclei of transfected COS-7 cells in order to identify apoptotic cells based on morphological features such as nuclear fragmentation and condensation. A fixative, consisting of a 3:1 mixture of absolute methanol and glacial acetic acid, was prepared immediately before use. An equal volume of fixative was added to the media of COS-7 cells growing on a culture slide and incubated for 2 minutes. The media/fixative mixture was removed from the cells and discarded, and 1 ml of fixative was added to the cells. After 5 minutes the fixative was discarded, and 1 ml of fresh fixative was added to the cells and incubated for 5 minutes. The fixative was discarded, and the cells were air-dried for 4 minutes before adding 1 ml of Hoescht stain (0.5 µg/ml Hoescht 33258 in PBS). After a 10-minute incubation in the dark, the staining solution was discarded and the slide was washed 3 times for 1 minute with deionized water. After washing, 1 ml of McIlvaine's buffer (0.021 M citric acid, 0.058 M $Na_2HPO_4.7H_2O$; pH 5.6) was added to the cells, and they were incubated in the dark for 20 minutes. The buffer was discarded, the cells were air-dried for 5 minutes in the dark and the chambers separating the wells of the culture slide were removed. A few drops of Vectashield mounting media for fluorescence (Vector Laboratories) was added to the slide and overlaid with a coverslip. The stained cells were viewed under a fluorescence microscope using a UV filter. Cells with brightly stained or fragmented nuclei were scored as apoptotic.

Annexin V-Cy3 Staining

An Annexin V-$Cy_3$ apoptosis detection kit (Sigma) was used to fluorescently label externalized phosphatidylserine on apoptotic cells. The kit was used according to the manufacturer's protocol with the following modifications. In brief, transfected COS-7 cells growing on four chamber culture slides were washed twice with PBS and three times with 1× Binding Buffer. 150 µl of staining solution (1 µg/ml AnnCy3 in 1× Binding Buffer) was added, and the cells were incubated in the dark for 10 minutes. The staining solution was then removed, and the cells were washed 5 times with 1× Binding Buffer. The chamber walls were removed from the culture slide, and several drops of 1× Binding Buffer were placed on the cells and overlaid with a coverslip. The stained cells were analyzed by fluorescence microscopy using a green filter to visualize the red fluorescence of positively stained (apoptotic) cells. The total cell population was determined by counting the cell number under visible light.

Example 3

The present example demonstrates modulation of apoptosis with apoptosis-specific eIF-5A and DHS.

Figure 23:
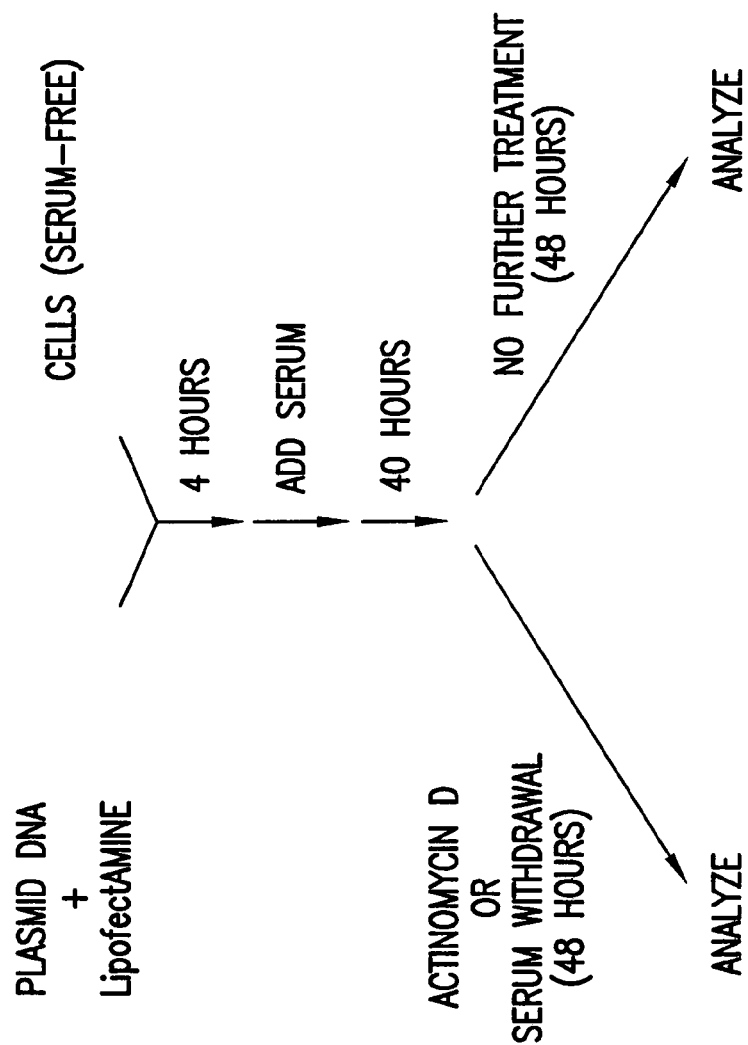
FIG. 23 is a flow chart illustrating the procedure for transient transfection of COS-7 cells.
Figure 24:
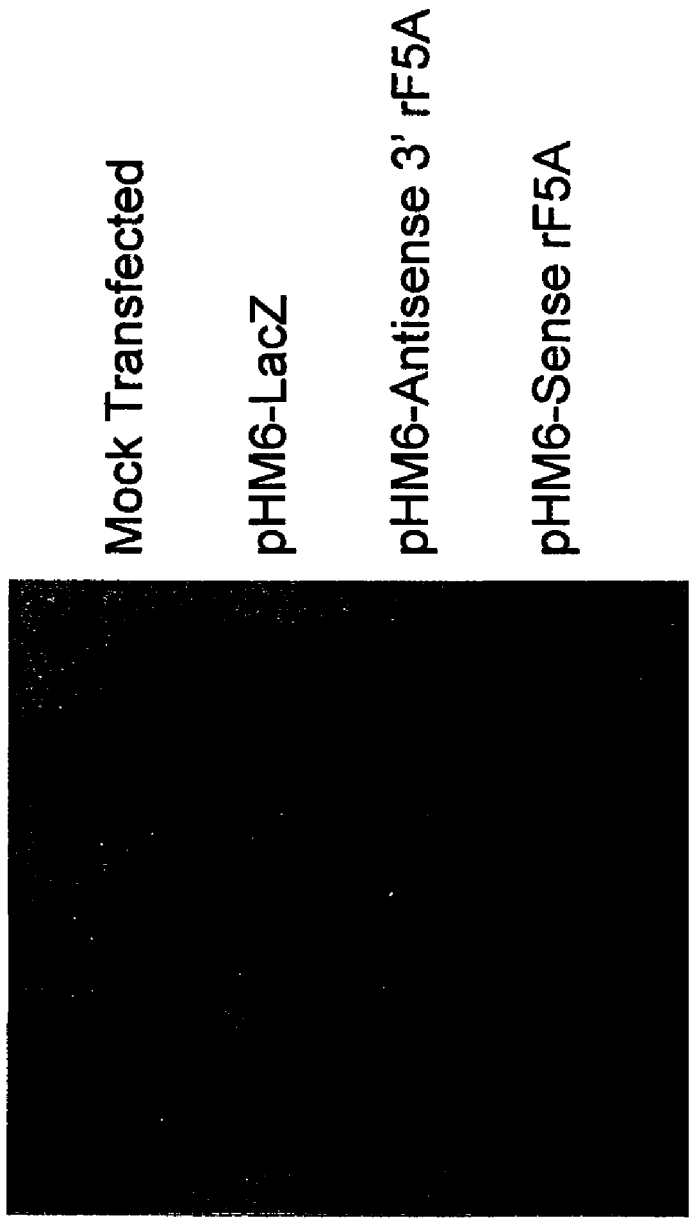
FIG. 24 is a Western blot of transient expression of foreign proteins in COS-7 cells following transfection with pHM6.

Using the general procedures and methods described in the previous examples, FIG. 23 is a flow chart illustrating the procedure for transient transfection of COS-7 cells, in which cells in serum-free medium were incubated in plasmid DNA in lipofectAMINE for 4 hours, serum was added, and the cells were incubated for a further 40 hours. The cells were then either incubated in regular medium containing serum for a further 48 hours before analysis (i.e. no further treatment), deprived of serum for 48 hours to induce apoptosis before analysis, or treated with actinomycin D for 48 hours to induce apoptosis before analysis.

FIG. 22 is a Western blot illustrating transient expression of foreign proteins in COS-7 cells following transfection with pHM6. Protein was isolated from COS-7 cells 48 hours after either mock transfection, or transfection with pHM6-LacZ, pHM6-Antisense 3' rF5A (pHM6-Antisense 3' UTR rat apoptosis eIF-5A), or pHM6-Sense rF5A (pHM6-Full length rat apoptosis eIF-5A). Five µg of protein from each sample was fractionated by SDS-PAGE, transferred to a PVDF membrane, and Western blotted with anti-[HA]-peroxidase. The bound antibody was detected by chemiluminescence and exposed to x-ray film for 30 seconds. Expression of LacZ (lane 2) and of sense rat apoptosis eIF-5A (lane 4) is clearly visible.

As described above, COS-7 cells were either mock transfected or transfected with pHM6-Sense rF5A (pHM6-Full length rat eIF-5A). Forty hours after transfection, the cells were induced to undergo apoptosis by withdrawal of serum for 48 hours. The caspase proteolytic activity in the transfected cell extract was measured using a fluorometric homogenous caspase assay kit (Roche Diagnostics). DNA fragmentation was also measured using the FragEL DNA Fragmentation Apoptosis Detection kit (Oncogene) which labels the exposed 3'-OH ends of DNA fragments with fluorescein-labeled deoxynucleotides.

Additional COS-7 cells were either mock transfected or transfected with pHM6-Sense rF5A (pHM6-Full length rat eIF-5A). Forty hours after transfection, the cells were either grown for an additional 48 hours in regular medium containing serum (no further treatment), induced to undergo apoptosis by withdrawal of serum for 48 hours or induced to undergo apoptosis by treatment with 0.5 µg/ml of Actinomycin D for 48 hours. The cells were either stained with Hoescht 33258, which depicts nuclear fragmentation accompanying apoptosis, or stained with Annexin V-$Cy_3$, which depicts phosphatidylserine exposure accompanying apoptosis. Stained cells were also viewed by fluorescence microscopy using a green filter and counted to determine the percentage of cells undergoing apoptosis. The total cell population was counted under visible light.

Figure 25:
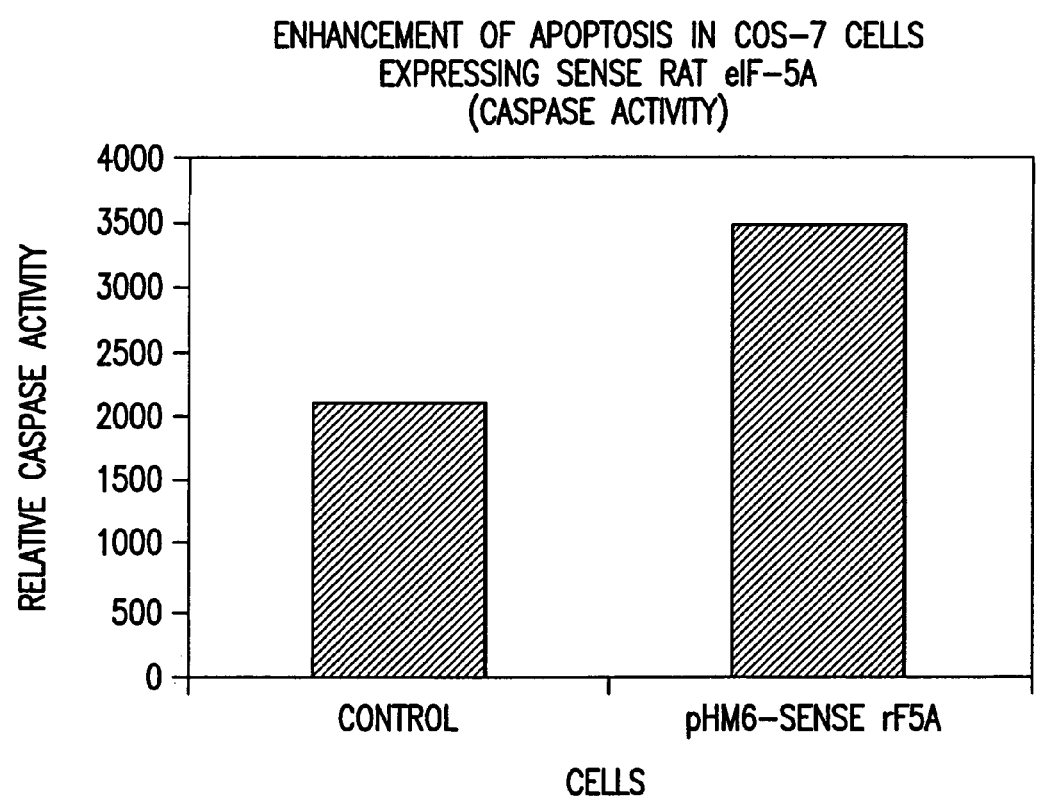
FIG. 25 illustrates enhanced apoptosis as reflected by increased caspase activity when COS-7 cells were transiently transfected with pHM6 containing full-length rat apoptosis-specific eIF-5A in the sense orientation.

FIG. 25 illustrates enhanced apoptosis as reflected by increased caspase activity when COS-7 cells were transiently transfected with pHM6 containing full-length rat apoptosis-induced eIF-5A in the sense orientation. Expression of rat apoptosis-induced eIF-5A resulted in a 60% increase in caspase activity.

Figure 26:
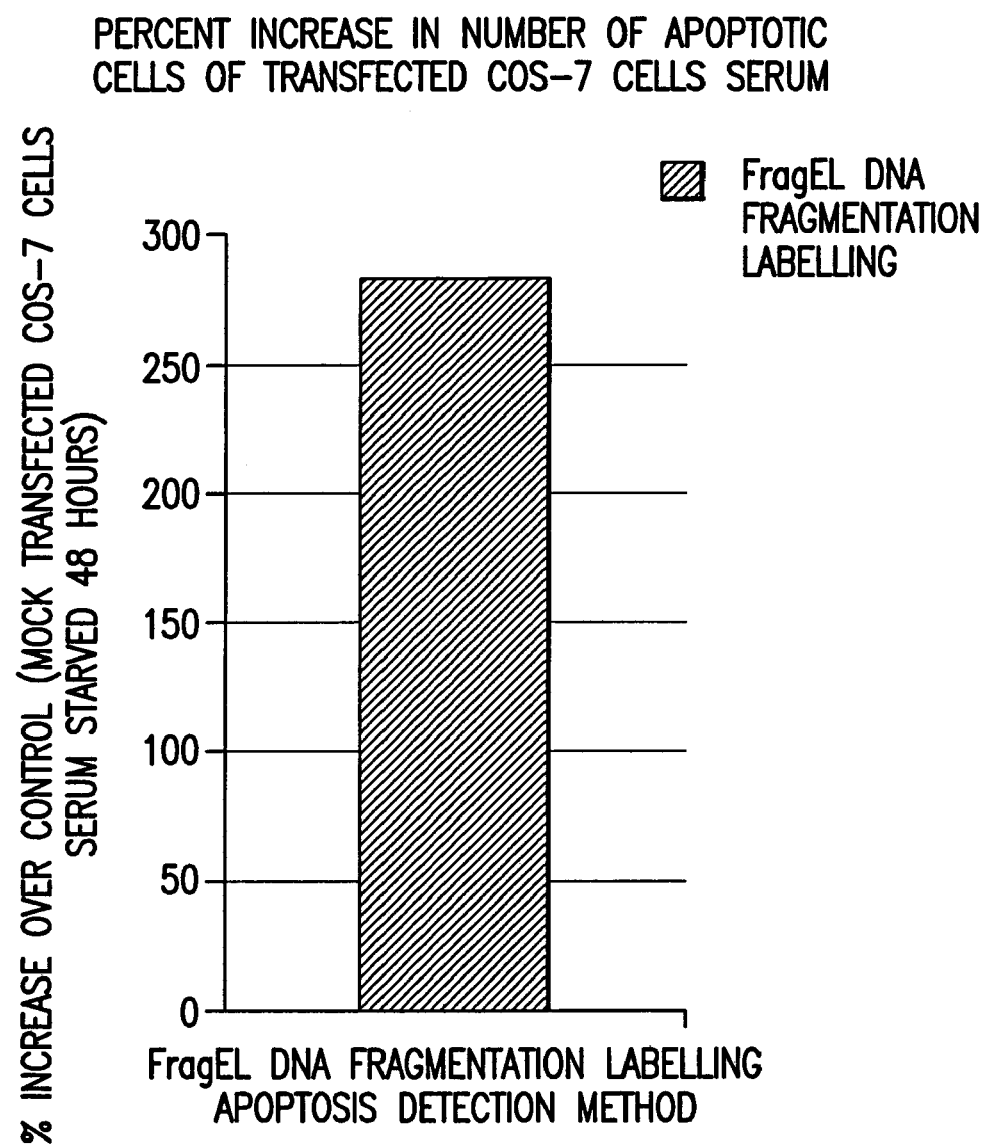
FIG. 26 illustrates enhanced apoptosis as reflected by increased DNA fragmentation when COS-7 cells were transiently transfected with pHM6 containing full-length rat apoptosis-specific eIF-5A in the sense orientation.
Figure 28:
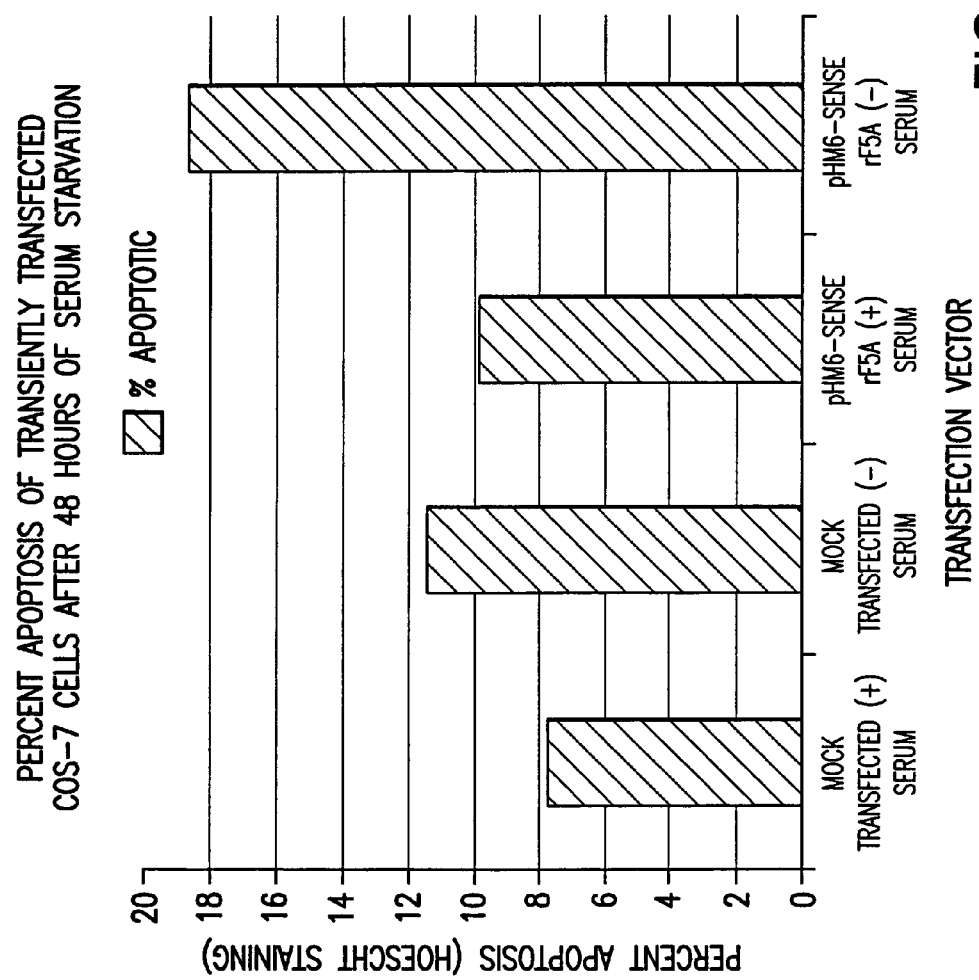
FIG. 28 illustrates enhanced apoptosis as reflected by increased nuclear fragmentation when COS-7 cells were transiently transfected with pHM6 containing full-length rat apoptosis-specific eIF-5A in the sense orientation.

FIG. 26 illustrates enhanced apoptosis as reflected by increased DNA fragmentation when COS-7 cells were transiently transfected with pHM6 containing full-length rat apoptosis-induced eIF-5A in the sense orientation. Expression of rat apoptosis-induced eIF-5A resulted in a 273% increase in DNA fragmentation. FIG. 27 illustrates detection of apoptosis as reflected by increased nuclear fragmentation when COS-7 cells were transiently transfected with pHM6 containing full-length rat apoptosis-induced eIF-5A in the sense orientation. There is a greater incidence of fragmented nuclei in cells expressing rat apoptosis-induced eIF-5A. FIG. 28 illustrates enhanced apoptosis as reflected by increased nuclear fragmentation when COS-7 cells were transiently transfected with pHM6 containing full-length rat apoptosis-induced eIF-5A in the sense orientation. Expression of rat apoptosis-induced eIF-5A resulted in a 27% and 63% increase in nuclear fragmentation over control in non-serum starved and serum starved samples, respectively.

Figure 29:
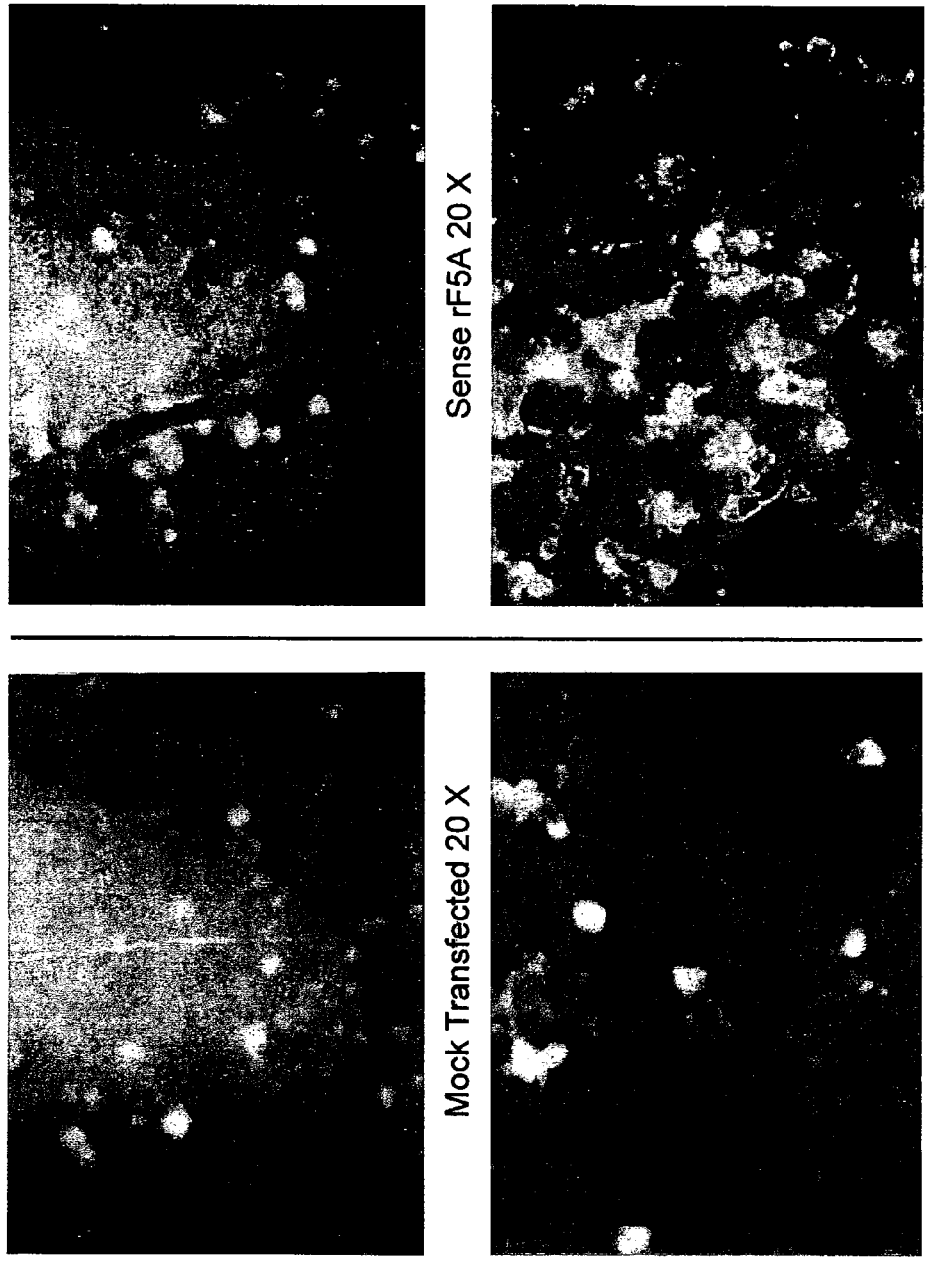
FIG. 29 illustrates detection of apoptosis as reflected by phosphatidylserine exposure when COS-7 cells were transiently transfected with pHM6 containing full-length rat apoptosis-specific eIF-5A in the sense orientation.
Figure 30:
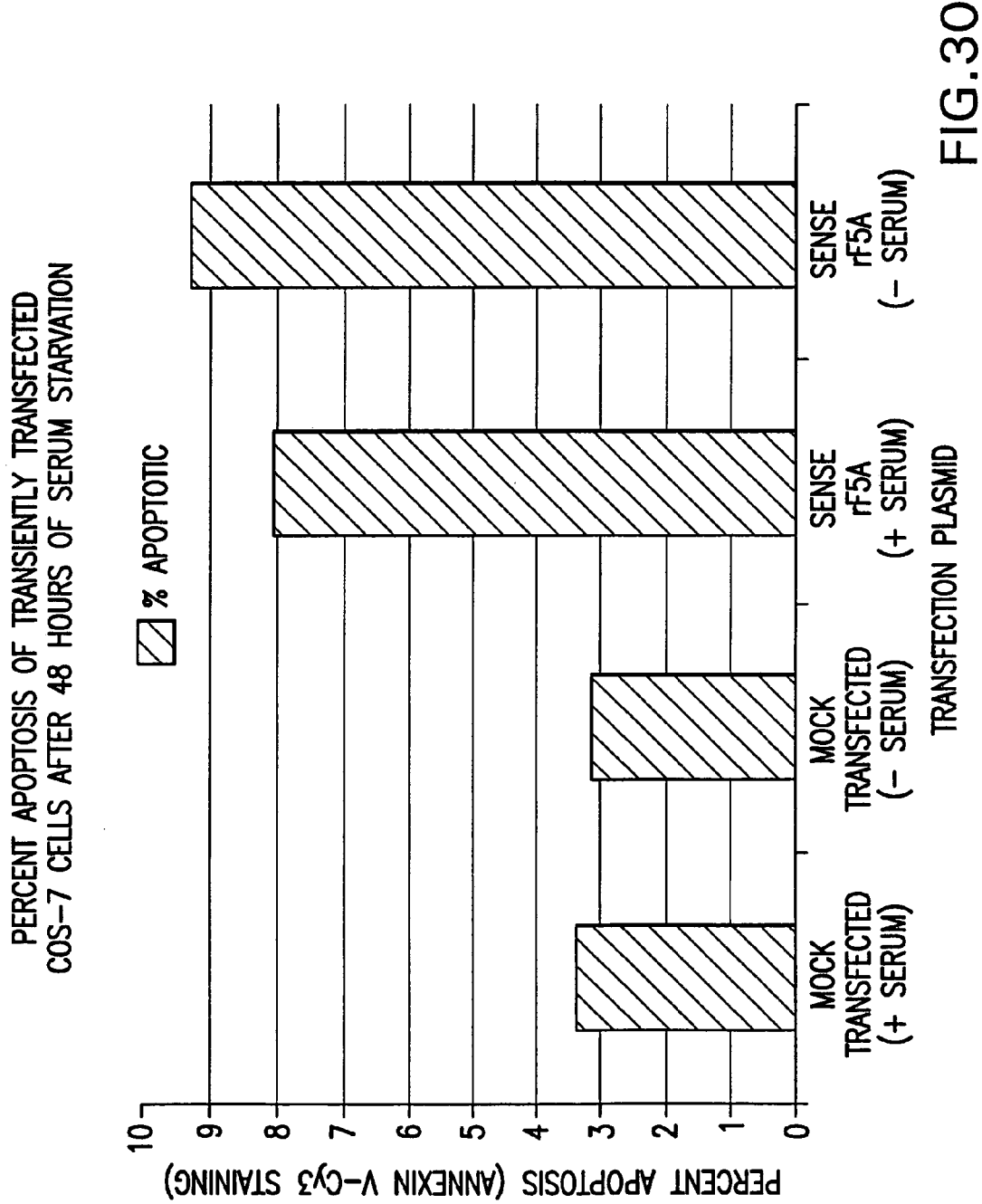
FIG. 30 illustrates enhanced apoptosis as reflected by increased phosphatidylserine exposure when COS-7 cells were transiently transfected with pHM6 containing full-length rat apoptosis-specific eIF-5A in the sense orientation.

FIG. 29 illustrates detection of apoptosis as reflected by phosphatidylserine exposure when COS-7 cells were transiently transfected with pHM6 containing full-length rat apoptosis-induced eIF-5A in the sense orientation. FIG. 30 illustrates enhanced apoptosis as reflected by increased phosphatidylserine exposure when COS-7 cells were transiently transfected with pHM6 containing full-length rat apoptosis-induced eIF-5A in the sense orientation. Expression of rat apoptosis-induced eIF-5A resulted in a 140% and 198% increase in phosphatidylserine exposure over control, in non-serum starved and serum starved samples, respectively.

Figure 31:
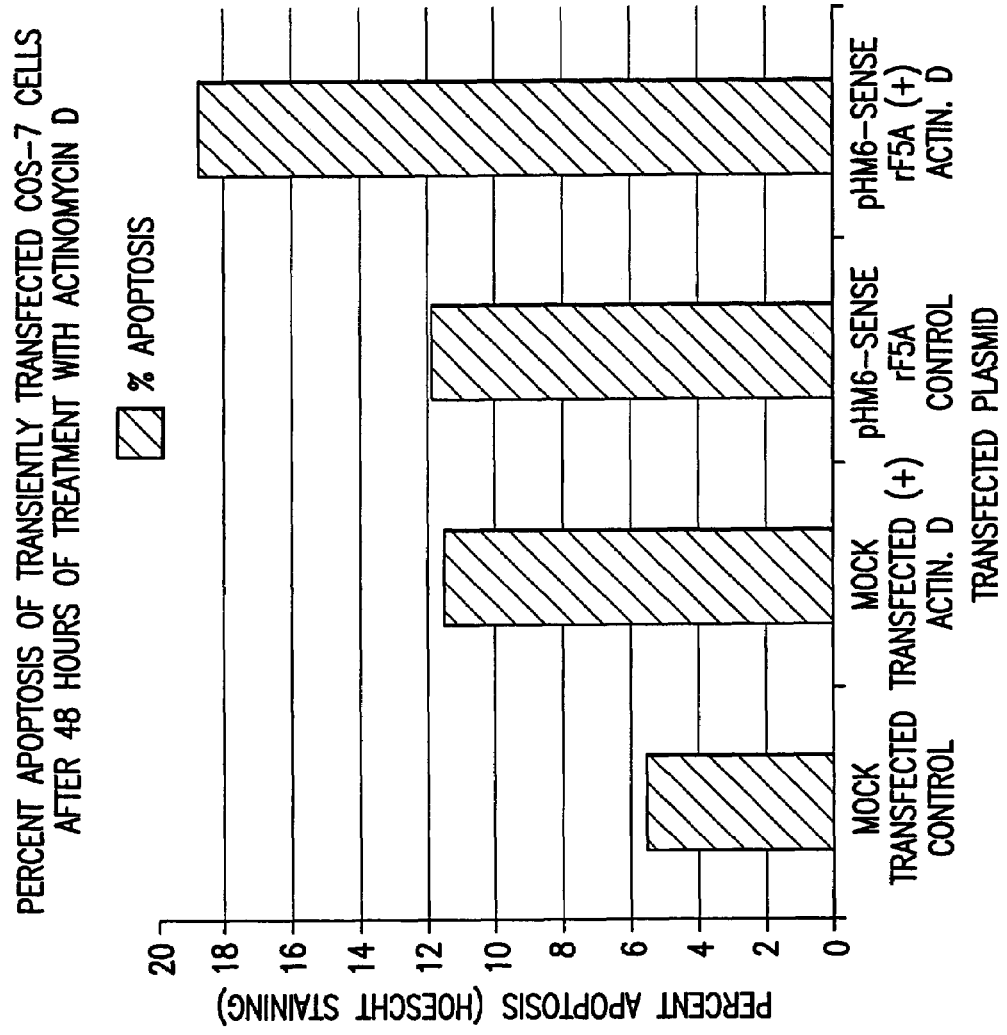
FIG. 31 illustrates enhanced apoptosis as reflected by increased nuclear fragmentation when COS-7 cells were transiently transfected with pHM6 containing full-length rat apoptosis-specific eIF-5A in the sense orientation.
Figure 32:
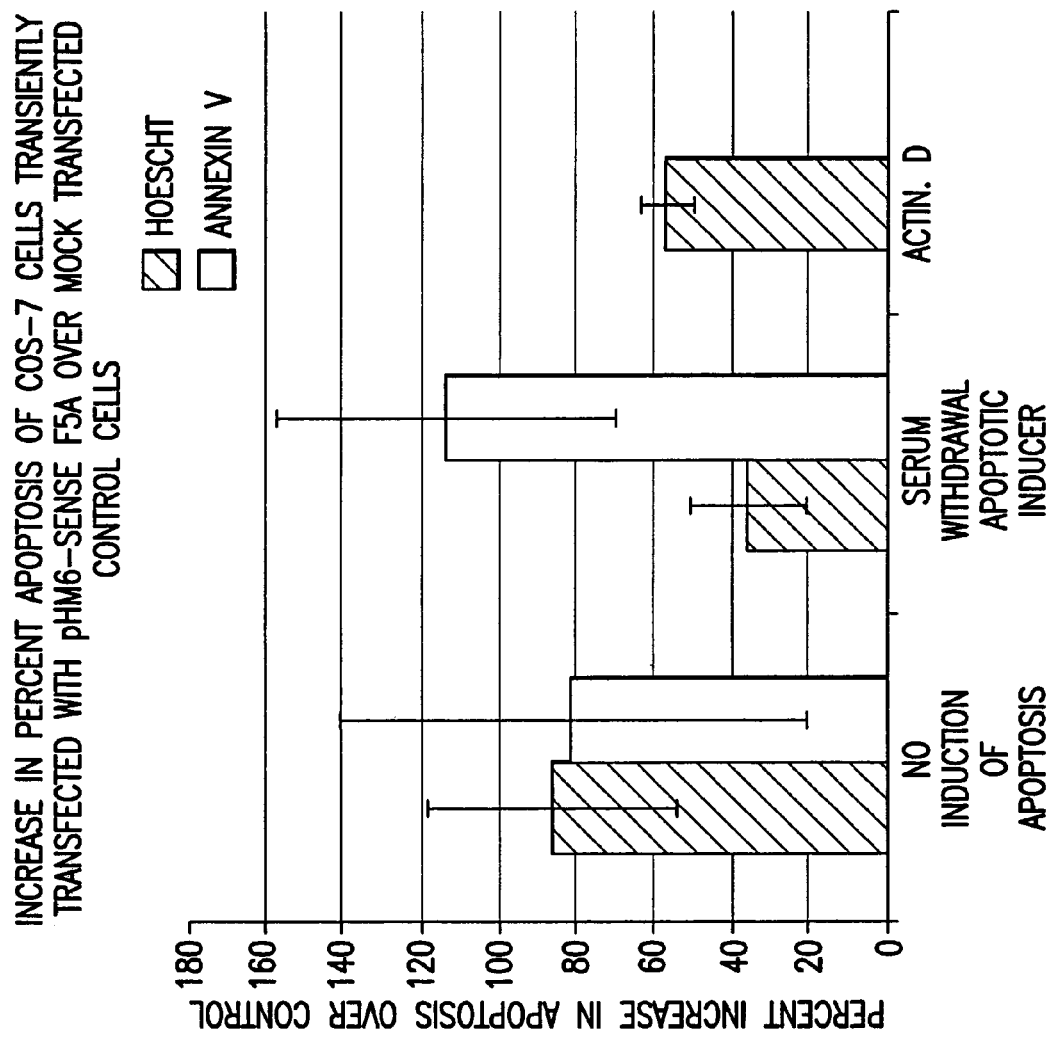
FIG. 32 illustrates enhanced apoptosis when COS-7 cells were transiently transfected with pHM6 containing full-length rat apoptosis-specific eIF-5A in the sense orientation.

FIG. 31 illustrates enhanced apoptosis as reflected by increased nuclear fragmentation when COS-7 cells were transiently transfected with pHM6 containing full-length rat apoptosis-induced eIF-5A in the sense orientation. Expression of rat apoptosis-induced eIF-5A resulted in a 115% and 62% increase in nuclear fragmentation over control in untreated and treated samples, respectively. FIG. 32 illustrates a comparison of enhanced apoptosis under conditions in which COS-7 cells transiently transfected with pHM6 containing full-length rat apoptosis-induced eIF-5A in the sense orientation were either given no further treatment or treatment to induce apoptosis.

Example 4

The present example demonstrates modulation of apoptotic activity following administration of apoptosis-specific eIF-5A and DHS.

Moreover, COS-7 cells were either mock transfected, transfected with pHM6-LacZ or transfected with pHM6-Sense rF5A (pHM6-Full length rat eIF-5A) and incubated for 40 hours. Five μg samples of protein extract from each sample were fractionated by SDS-PAGE, transferred to a PVDF membrane, and Western blotted with a monoclonal antibody that recognizes Bcl-2. Rabbit anti-mouse IgG conjugated to peroxidase was used as a secondary antibody, and bound antibody was detected by chemiluminescence and exposure to x-ray film. Results are shown in FIG. 32. Less Bcl-2 is detectable in cells transfected with pHM6-Sense rF5A than in those transfected with pHM6-LacZ; therefore, Bcl-2 is down-regulated.

Additional COS-7 cells were either mock transfected, transfected with pHM6-antisense 3' rF5A (pHM6-antisense 3' UTR of rat apoptosis-specific eIF-5A) or transfected with pHM6-Sense rF5A (pHM6-Full length rat apoptosis-specific eIF-5A). Forty hours after transfection, the cells were induced to undergo apoptosis by withdrawal of serum for 48 hours. Five μg samples of protein extract from each sample were fractionated by SDS-PAGE, transferred to a PVDF membrane, and Western blotted with a monoclonal antibody that recognizes Bcl-2. Rabbit anti-mouse IgG conjugated to peroxidase was used as a secondary antibody, and bound antibody was detected by chemiluminescence and exposure to x-ray film.

Also additionally, COS-7 cells were either mock transfected, transfected with pHM6-LacZ or transfected with pHM6-Sense rF5A (pHM6-Full length rat eIF-5A) and incubated for 40 hours. Five μg samples of protein extract from each sample were fractionated by SDS-PAGE, transferred to a PVDF membrane, and Western blotted with a monoclonal antibody that recognizes p53. Goat anti-mouse IgG conjugated to alkaline phosphatase was used as a secondary antibody, and bound antibody was detected a colorimetrically.

Finally, COS-7 cells were either mock transfected, transfected with pHM6-LacZ or transfected with pHM6-Sense rF5A (pHM6-Full length rat eIF-5A) and incubated for 40 hours. Five μg samples of protein extract from each sample were fractionated by SDS-PAGE, transferred to a PVDF membrane, and probed with a monoclonal antibody that recognizes p53. Corresponding protein blots were probed with anti-[HA]-peroxidase to determine the level of rat apoptosis-specific eIF-5A expression. Goat anti-mouse IgG conjugated to alkaline phosphatase was used as a secondary antibody, and bound antibody was detected by chemiluminescence.

Figure 33:
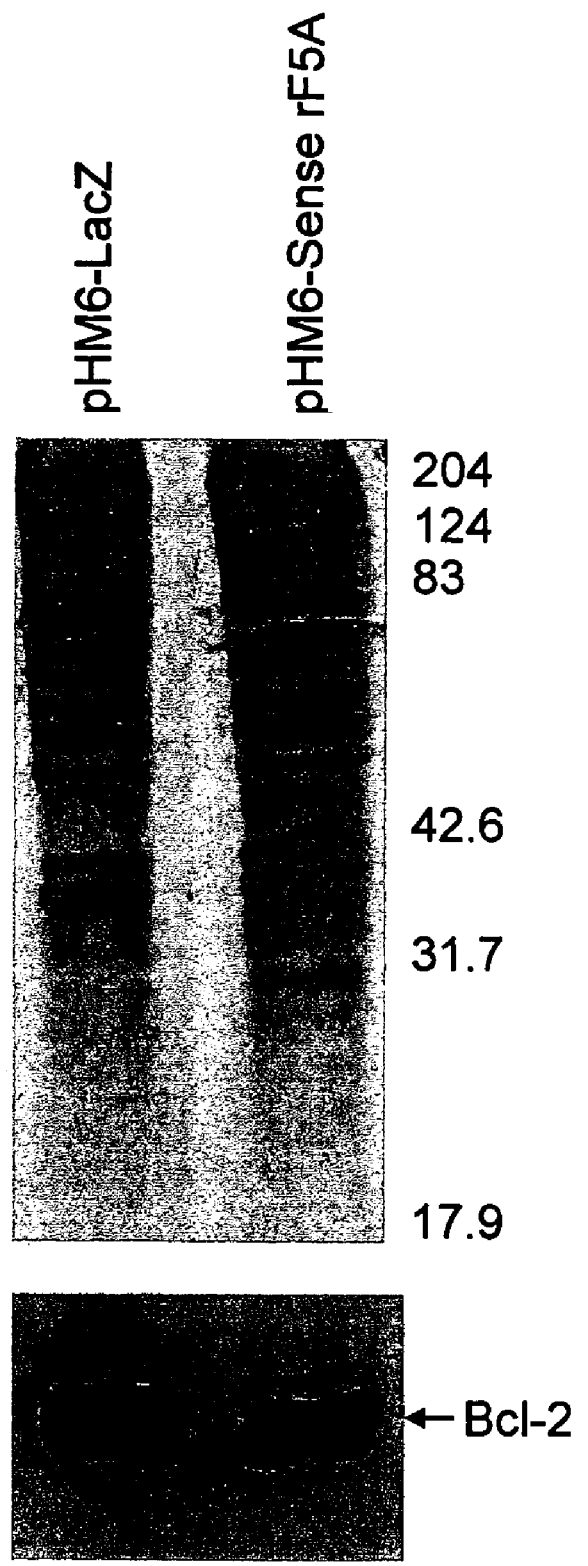
FIG. 33 illustrates down-regulation of Bcl-2 when COS-7 cells were transiently transfected with pHM6 containing full-length rat apoptosis-specific eIF-5A in the sense orientation.

FIG. 33 illustrates downregulation of Bcl-2 when COS-7 cells were transiently transfected with pHM6 containing full-length rat apoptosis-induced eIF-5A in the sense orientation. The upper panel illustrates the Coomassie-blue-stained protein blot; the lower panel illustrates the corresponding Western blot. Less Bcl-2 is detectable in cells transfected with pHM6-Sense rF5A than in those transfected with pHM6-LacZ.

Figure 34:
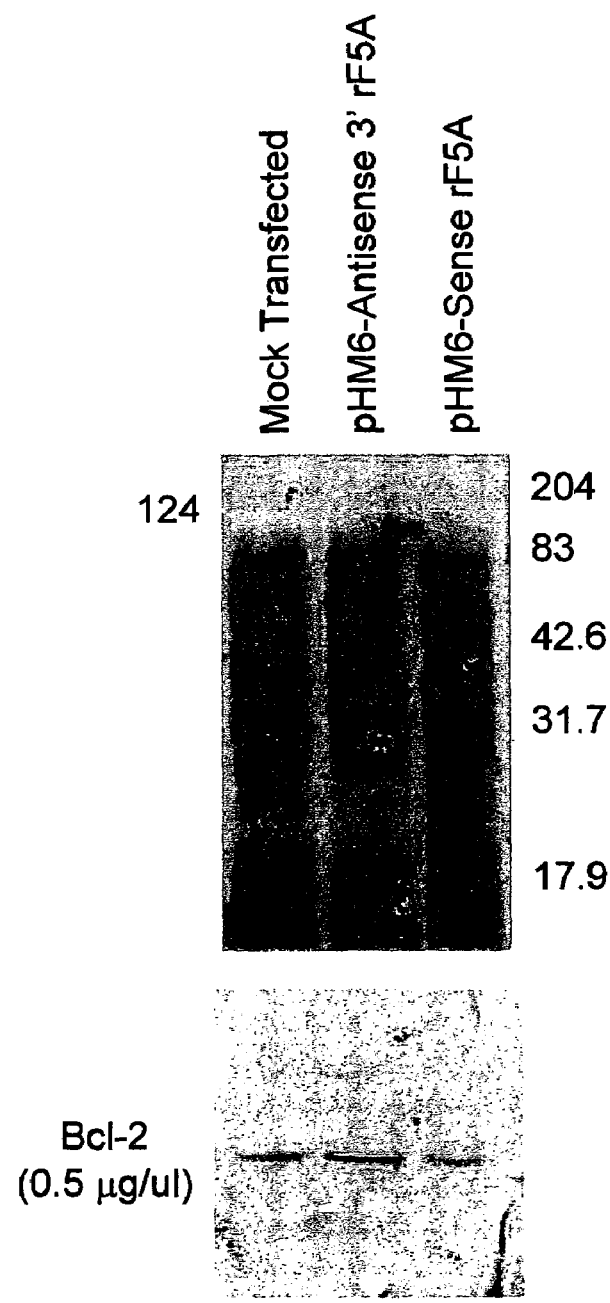
FIG. 34 is a Coomassie-blue-stained protein blot and the corresponding Western blot of COS-7 cells transiently transfected with pHM6 containing full-length rat apoptosis-specific eIF-5A in the antisense orientation using Bcl-2 as a probe.

FIG. 34 illustrates upregulation of Bcl-2 when COS-7 cells were transiently transfected with pHM6 containing full-length rat apoptosis-induced eIF-5A in the antisense orientation. The upper panel illustrates the Coomassie-blue-stained protein blot; the lower panel illustrates the corresponding Western blot. More Bcl-2 is detectable in cells transfected with pHM6-antisense 3' rF5A than in those mock transfected or transfected with pHM6-Sense rF5A.

Figure 35:
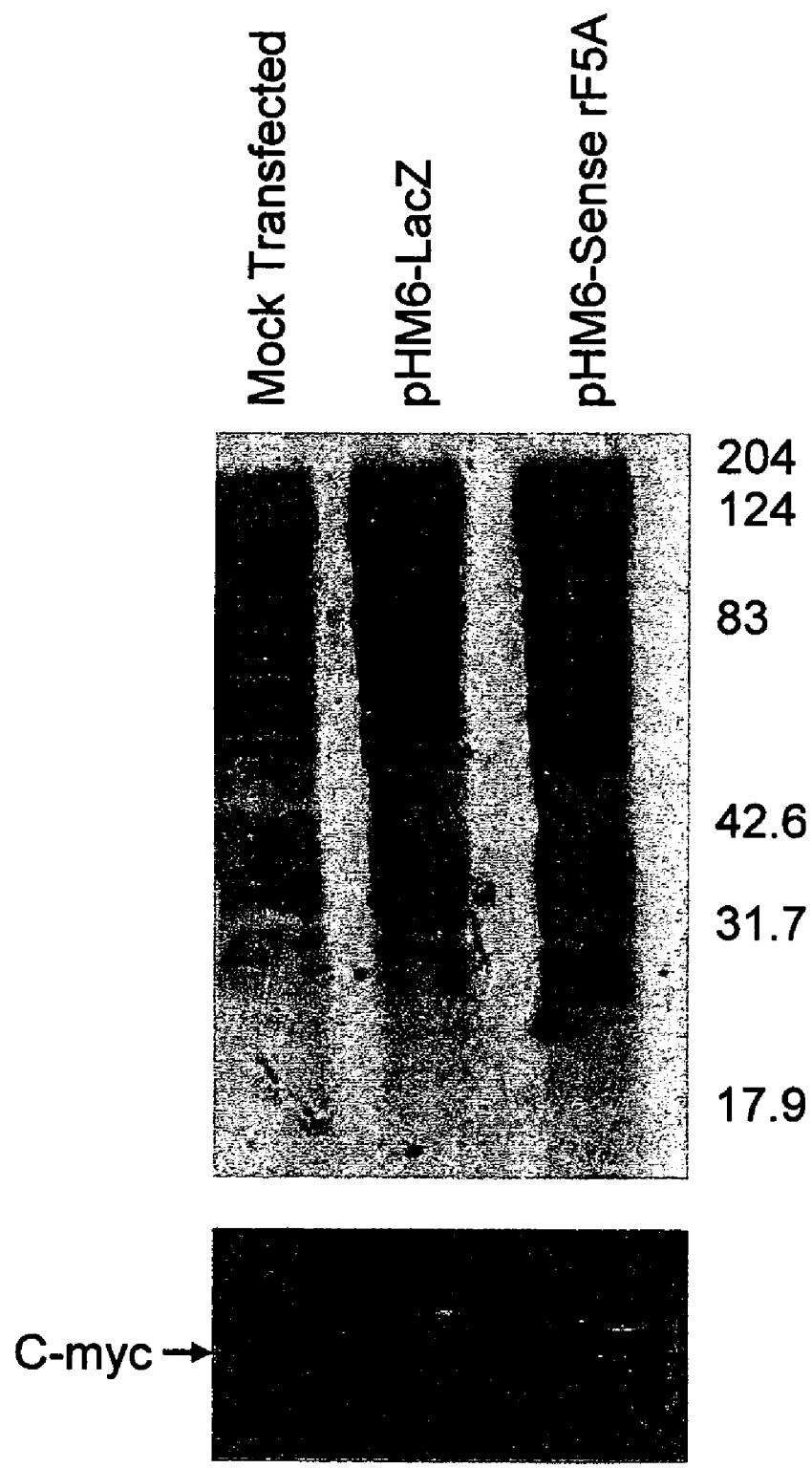
FIG. 35 is a Coomassie-blue-stained protein blot and the corresponding Western blot of COS-7 cells transiently transfected with pHM6 containing full-length rat apoptosis-specific eIF-5A in the sense orientation using c-Myc as a probe.

FIG. 35 illustrates upregulation of c-Myc when COS-7 cells were transiently transfected with pHM6 containing full-length rat apoptosis-induced eEF-5A in the sense orientation. The upper panel illustrates the Coomassie-blue-stained protein blot; the lower panel illustrates the corresponding Western blot. More c-Myc is detectable in cells transfected with pHM6-Sense rF5A than in those transfected with pHM6-LacZ or the mock control.

Figure 36:
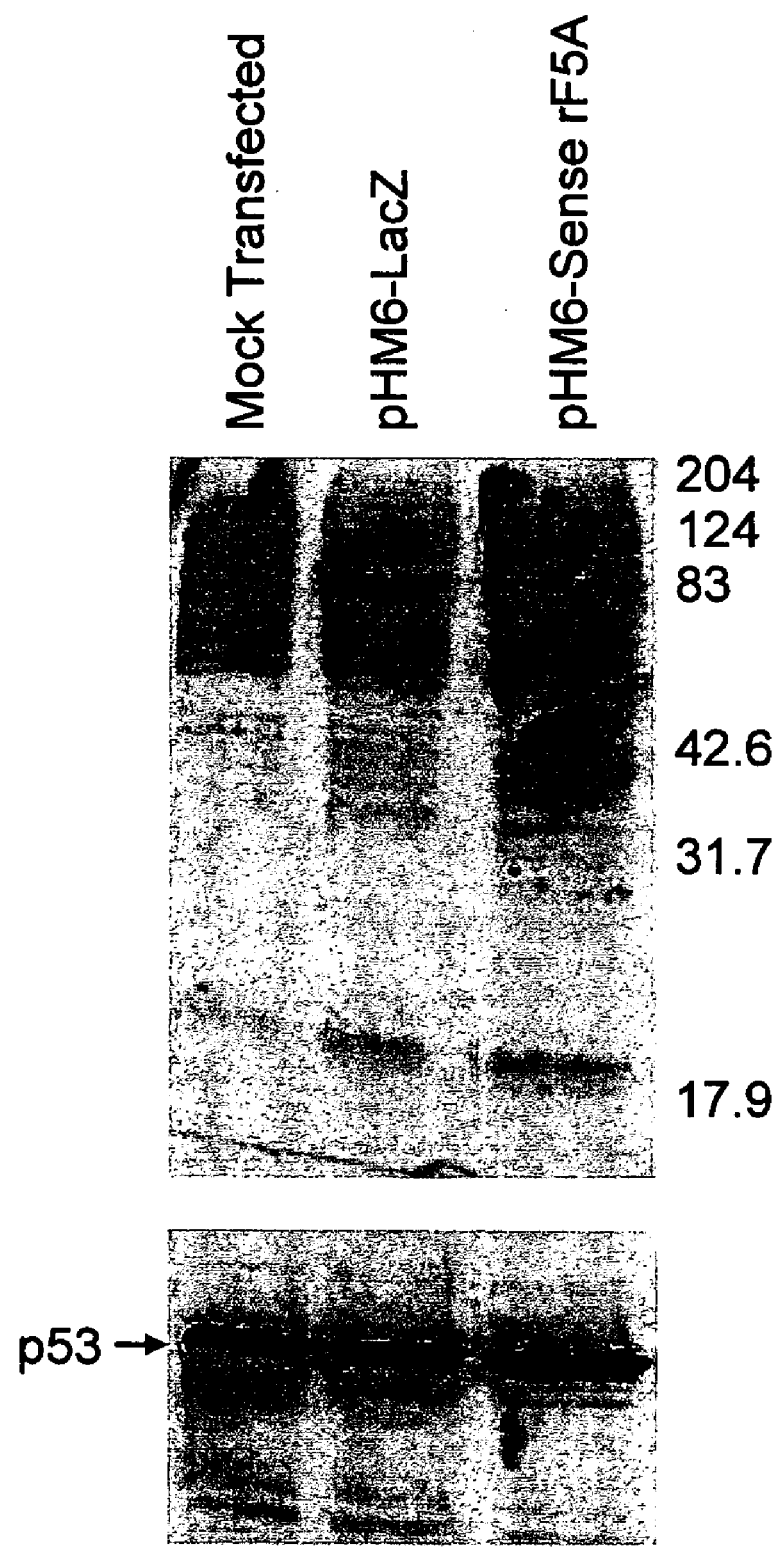
FIG. 36 is a Coomassie-blue-stained protein blot and the corresponding Western blot of COS-7 cells transiently transfected with pHM6 containing full-length rat apoptosis-specific eIF-5A in the sense orientation when p53 is used as a probe.

FIG. 36 illustrates upregulation of p53 when COS-7 cells were transiently transfected with pHM6 containing full-length rat apoptosis-induced eIF-5A in the sense orientation. The upper panel illustrates the Coomassie-blue-stained protein blot; the lower panel illustrates the corresponding Western blot. More p53 is detectable in cells transfected with pHM6-Sense rF5A than in those transfected with pHM6-LacZ or the mock control.

Figure 37B:
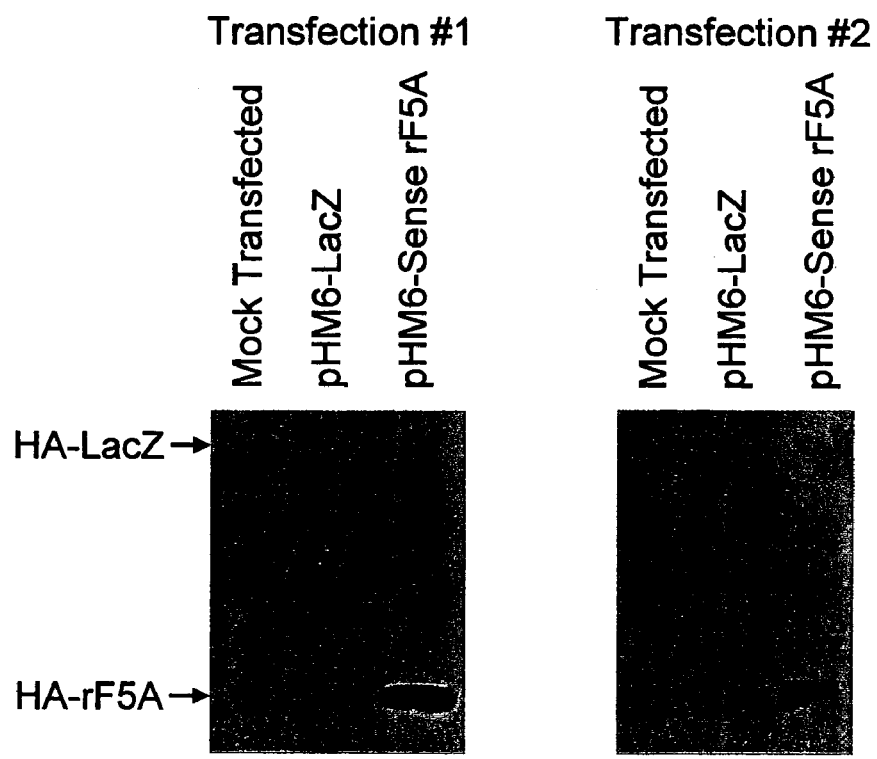
FIG. 37 is a Coomassie-blue-stained protein blot and the corresponding Western blot of expression of pHM6-full-length rat apoptosis-specific eIF-5A in COS-7 cells using an anti-[HA]-peroxidase probe and a Coomassie-blue-stained protein blot and the corresponding Western blot of expression of pHM6-full-length rat apoptosis-specific eIF-5A in COS-7 cells when a p53 probe is used.
Figure 37C:
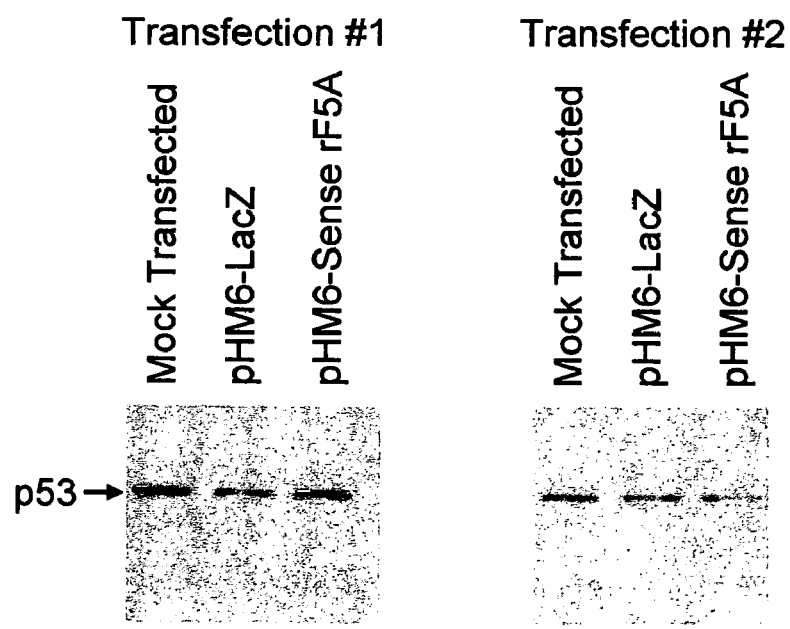

FIG. 37 illustrates the dependence of p53 upregulation upon the expression of pHM6-full length rat apoptosis-induced eIF-5A in COS-7 cells. In the Western blot probed with anti-[HA]-peroxidase, the upper panel illustrates the Coomassie-blue-stained protein blot and the lower panel illustrates the corresponding Western blot. More rat apoptosis-induced eIF-5A is detectable in the first transfection than in the second transfection. In the Western blot probed with anti-p53, the upper panel in A illustrates a corresponding Coomassie-blue-stained protein blot and the lower panel illustrates the Western blot with p53. For the first transfection, more p53 is detectable in cells transfected with pHM6-Sense rF5A than in those transfected with pHM6-LacZ or the mock control. For the second transfection in which there was less expression of rat apoptosis-induced eIF-5A, there was no detectable difference in levels of p53 between cells transfected with pHM6-Sense rF5A, pHM6-LacZ or the mock control.

Example 5

The present example demonstrates that apoptosis-specific eIF-5A can induce apoptosis in cells with active p53 (RKO cells) and in cells without active p53 (RKO-E6 cells), indicating that apoptosis-specific eIF-5A can initiate apoptosis through pathway(s) other than the p53 pathway. This also supports our contention that it is acting upstream and likely able to kill a wide range of different types of cancers.

The present example also indicates that the active site of eIF-5A1 is the carboxy terminus of the protein (i.e. see experiments with truncated eIF-5A1), which most likely contains the RNA binding domain.

Further, the present example also demonstrates that human eIF-5A2 is most likely a proliferating eIF-5A as it is unable to induce apoptosis. Thus, it is believed that of the two eIF-5A genes in the human data bank, apoptosis-specific eIF-5A1 is the apoptosis gene, and eIF-5A2 is the proliferation gene.

Culture of RKO and RKO-E6 Cells RKO (American Type Culture Collection CRL-2577), a human colon carcinoma cell line expressing wild-type p53, and RKO-E6 (American Type Culture Collection CRL-2578), a cell line derived from RKO that contains a stably integrated human papilloma virus E6 oncogene that causes a decrease in normal p53 level and function, were used for transfection-based experiments. RKO and RKO-E6 cells were cultured in Minimum Essential Medium Eagle (MEM) with non-essential amino acids, Earle's salts, and L-glutamine. The culture media was supplemented with 10% fetal bovine serum (FBS) and 100 units of penicillin/streptomycin. The cells were grown at 37° C. in a humidified environment of 5% $CO_2$ and 95% air. The cells were subcultured every 3 to 4 days by detaching the adherent cells with a solution of 0.25% trypsin and 1 mM EDTA. The detached cells were dispensed at a split ratio of 1:10 to 1:12 into a new culture dish with fresh media.

Cloning of human eIF5A2

Human eIF5A2 was isolated by RT-PCR from RNA isolated from RKO cells using primers designed against the sequence of human eIF5A2 available from GenBank (ACCESSION XM_113401). FIG. 38 provides an alignment of human eIF-5A isolated from RKO cells with the sequence of human eIF-5A2. RNA was isolated from RKO cells using the GenElute Mammalian Total RNA Miniprep Kit (Sigma). The forward primer used to amplify eIF5A2 had the sequence 5' AAACTACCATCTCCCCTGCC 3' (SEQ ID NO:28) and the reverse primer had the sequence 5' TGCCCTACACAGGCTGAAAG 3' (SEQ ID NO:29). The resulting 936 bp PCR product was subcloned into the pGEM-T Easy Vector (Promega) and sequenced.

The pGEM-T Easy-eIF5A2 construct was then used as template to generate a eIF5A2 PCR fragment to be subcloned in frame into the mammalian expression vector pHM6 (Roche). The forward primer used to amplify human eIF5A2 was 5' ATCAAGCTTGCCCACCATGGCAGACG 3' (SEQ ID NO:30) and the reverse primer was 5' AACGAATTCCATGCCTGATGTTTCCG 3' (SEQ ID NO:31). The resulting 505 bp PCR product was digested with Hind 3 and EcoR 1 and subcloned into the Hind 3 and EcoR1 sites of pHM6.

Construction of pHM6-Truncated eI5A1

In order to determine if the carboxy-terminal region of eIF5A$^1$ is important for its apoptosis-inducing activity, a carboxy-terminal deleted eIF5A1 was constructed. The truncated eIF5A1, coding for amino acids 1 to 127, was generated by PCR using pBS-rat eIF5A1 as template. The forward PCR primer was 5' GCCAAGCTTAATGGCAGATGATTTGG 3' (SEQ ID NO:22) and the reverse primer was 5' TCCGAATTCGTACTTCTGCTCAATC 3' (SEQ ID NO:32). The resulting 390 bp PCR product was digested with EcoR 1 and Hind 3 and subcloned into the EcoR 1 and Hind 3 sites of pHM6.

Transfection

RKO or RKO-E6 cells to be used in transfection experiments were cultured in 8 well chamber culture slides (Falcon) for cells to be used for Hoescht staining or 6 well plates for cells to be analyzed by flow cytometry. The cells were grown in MEM media supplemented with 10% FBS but lacking penicillin/streptomycin to 70 to 80% confluency. Transfection medium sufficient for one well of an 8 well culture slide was prepared by diluting 0.425 μg of plasmid DNA in 22 μl of serum-free MEM and incubating the mixture at room temperature for 15 minutes. 0.85 μl of the transfection reagent, LipofectAMINE (Gibco, BRL), was diluted in 22 μl of serum-free MEM and incubated for 5 minutes at room temperature. After 5 minutes the LipofectAMINE mixture was added to the DNA mixture and incubated at room temperature for 30 to 60 minutes. The cells to be transfected were washed once with serum-free MEM before adding 44 μl of MEM to the transfection medium and overlaying it over the cells. The cells were placed back in the growth chamber for 4 hours. After the incubation, 88 μl of MEM+20% FBS was added to the cells. The cells were then cultured for a further 44 hours and then stained with Hoescht 33258 as previously described. In another set of experiments, RKO or RKO-E6 cells in 8-well culture slides were treated with 0.25 μg/ml Actinomycin D 24 hours after transfection and stained with Hoescht 20 hours later. Transfections carried out in 6-well plates were performed in the same manner except that all the reagents were increased by 4.81 times. RKO cells transfected in 6 well plates were harvested 48 hours after transfection and fixed for analysis by flow cytometry as described below.

Determination of Transfection Efficiency

The efficiency of transfection was determined by staining pHM6-LacZ-transfected cells with 5-bromo-4-chloro-3-indolyl-beta-D-galactopyranoside (X-GAL). Blue-stained cells are LacZ-expressing transfected cells, and transfection efficiency was calculated as the number of blue stained cells divided by the total number of cells. Transfected cells were stained 48 hours following transfection. The cells were washed twice with PBS and then fixed for 10 minutes at room temperature in 0.5% gluteraldehyde/PBS. The cells were washed three times with 1 mM $MgCl_2$/PBS and then incubated with staining solution [5 mM $K_4Fe(CN)_6.3H_2O$, 5 mM $K_3Fe(CN)_6$, 1 mM $MgCl_2$, 0.1% X-GAL in PBS] until blue-stained cells appeared.

Hoescht Staining

The nuclear stain, Hoescht, was used to label the nuclei of transfected RKO and RKO-E6 cells in order to identify apoptotic cells based on nuclear fragmentation and condensation. A fixative, consisting of a 3:1 mixture of absolute methanol and glacial acetic acid, was prepared immediately before use. An equal volume of fixative was added to the media of cells growing on a culture slide and incubated for 2 minutes. The media/fixative mixture was removed from the cells and discarded, and 1 ml of fixative was added to the cells. After 5 minutes the fixative was discarded and 1 ml of fresh fixative was added to the cells and incubated for 5 minutes. The fixative was discarded and the cells were air-dried for 4 minutes before adding 1 ml of Hoescht stain (0.5 μg/ml Hoescht 33258 in PBS). After a 10 minute incubation in the dark, the staining solution was discarded and the slide was washed 3 times for 1 minute with deionized water. After washing, 1 ml of McIlvaine's buffer (0.021 M citric acid, 0.058 M $Na_2HPO_4.7H_2O$; pH 5.6) was added to the cells and incubated in the dark for 20 minutes. The buffer was discarded and the cells were air-dried for 5 minutes in the dark and the chambers separating the wells of the culture slide were removed. A few drops of Vectashield mounting media for fluorescence (Vector Laboratories) was added to the slide and overlayed with a coverslip. The stained cells were viewed under a fluorescent microscope using a UV filter. Cells with brightly stained or fragmented nuclei were scored as apoptotic.

DNA Fragmentation Detection by Flow Cytometry

DNA fragments generated during apoptosis were labeled with fluorescein-labeled deoxynucleotides using the Fluorescein-FragE™ DNA Fragmentation Detection Kit (Oncogene Research Products). Cells transfected with various constructs in 6 well culture plates were harvested by trypsinization 48 hours after transfection and fixed and labeled according to the manufacturer's instructions. Briefly, the cells were pelleted at 1000×g for 5 minutes at 4° C. and washed once in PBS (8 g/L NaCl, 0.2 g/L KCl, 1.44 g/L $Na_2HPO_4$, and 0.24 g/L $KH_2PO_4$). The cells were resuspended in 4% formaldehyde/PBS and incubated at room temperature for 10 minutes. The cells were pelleted again, resuspended in 1 ml of 80% ethanol, and stored at 4° C. On the day of analysis, 1 ml of fixed cells (at 1×106 cells/ml) was transferred to a microftige tube and the cells pelleted by centrifugation at 1000×g for 5 minutes. The pelleted cells were resuspended in 200 µl of 1×TBS (20 mM Tris pH 7.6, 140 mM NaCl) and incubated 10 to 15 minutes at room temperature. The cells were then pelleted again and resuspended in 100 µl of 20 pg/ml proteinase K and incubated for 5 minutes at room temperature. The cells were pelleted and resuspended in 100 µl of 1× TdT Equilibration buffer and incubated at room temperature for 10 to 30 minutes. The cells were then pelleted by centrifugation and resuspended in 60 µl of TdT Labeling Reaction Mixture and incubated for 1 to 1.5 hours in the dark. After the incubation, the cells were pelleted by centrifugation and washed twice in 200 µl of 1×TBS. The cells were resuspended in a final volume of 0.5 ml 1×TBS and analyzed on a flow cytometer equipped with a 488 nm argon ion laser source.

Protein Extraction and Western Blotting

Protein was isolated for Western blotting from transfected cells by washing the cells twice in PBS and then adding 150 µl of hot SDS gel-loading buffer (50 mM Tris-HCl pH 6.8, 100 mM dithiothreitol, 2% SDS, 0.1% bromophenol blue, and 10% glycerol). The cell lysate was collected in a microcentrifuge tube, heated at 95° C. for 10 minutes, and then centrifuged at 13,000×g for 10 minutes. The supernatant was transferred to a fresh microcentrifuge tube and stored at −20° C. until ready for use.

For Western blotting, 5 µg or 10 µg of total protein was separated on a 12% SDS-polyacrylamide gel. The separated proteins were transferred to a polyvinylidene difluoride membrane. The membrane was then incubated for one hour in blocking solution (5% skim milk powder, 0.02% sodium azide in PBS) and washed three times for 15 minutes in PBS-T (PBS+0.05% Tween-20). The membrane was stored overnight in PBS-T at 4° C. After being warmed to room temperature the next day, the membrane was blocked for 30 seconds in 1 µg/ml polyvinyl alcohol. The membrane was rinsed 5 times in deionized water and then blocked for 30 minutes in a solution of 5% milk in PBS. The primary antibody was preincubated for 30 minutes in a solution of 5% milk in PBS/0.025% Tween-20 prior to incubation with the membrane.

The membranes were blotted with either a monoclonal antibody from Oncogene which recognizes p53 (Ab-6), or a polyclonal antibody directed against a synthetic peptide (amino-CRLPEGDLGKEIEQKYD-carboxy) SEQ ID NO: 33 homologous to the c-terminal end of human eIF5A1 that was raised in chickens. The monoclonal antibody to p53 was used at a dilution of 0.1 µg/ml and the antibody against eIF5A1 was used at a dilution of 1:1000. After incubation with primary antibody for 60 to 90 minutes, the membrane was washed 3 times for 15 minutes in PBS-T. Secondary antibody was then diluted in 1% milk in PBS/0.025% Tween-20 and incubated with the membrane for 60 to 90 minutes. When p53 (Ab-6) was used as the primary antibody, the secondary antibody used was a goat anti-mouse IgG conjugated to alkaline phosphatase (Rockland) at a dilution of 1:1000. When anti-eIF5A1 was used as the primary antibody, a rabbit anti-chicken IgY conjugated to peroxidase (Gallus Immunotech) was used at a dilution of 1:10000. After incubation with the secondary antibody, the membrane was washed 3 times in PBS-T.

Two detection methods were used to develop the blots, a colourimetric method and a chemiluminescent method. The colourimetric method was used only when p53 (Ab-6) was used as the primary antibody in conjunction with the alkaline phosphatase-conjugated secondary antibody. Bound antibody was visualized by incubating the blot in the dark in a solution of 0.33 mg/mL nitro blue tetrazolium, 0.165 mg/mL 5-bromo-4-chloro-3-indolyl phosphate, 100 mM NaCl, 5 mM $MgCl_2$, and 100 mM Tris-HCl (pH 9.5). The color reaction was stopped by incubating the blot in 2 mM EDTA in PBS. A chemiluminescent detection method was used for all other primary antibodies, including anti-[HA]-peroxidase and anti-eIF5A1. The ECL Plus Western blotting detection kit (Amersham Pharmacia Biotech) was used to detect peroxidase-conjugated bound antibodies. In brief, the membrane was lightly blotted dry and then incubated in the dark with a 40:1 mix of reagent A and reagent B for 5 minutes. The membrane was blotted dry, placed between sheets of acetate, and exposed to X-ray film for time periods varying from 10 seconds to 30 minutes.

Figure 39:
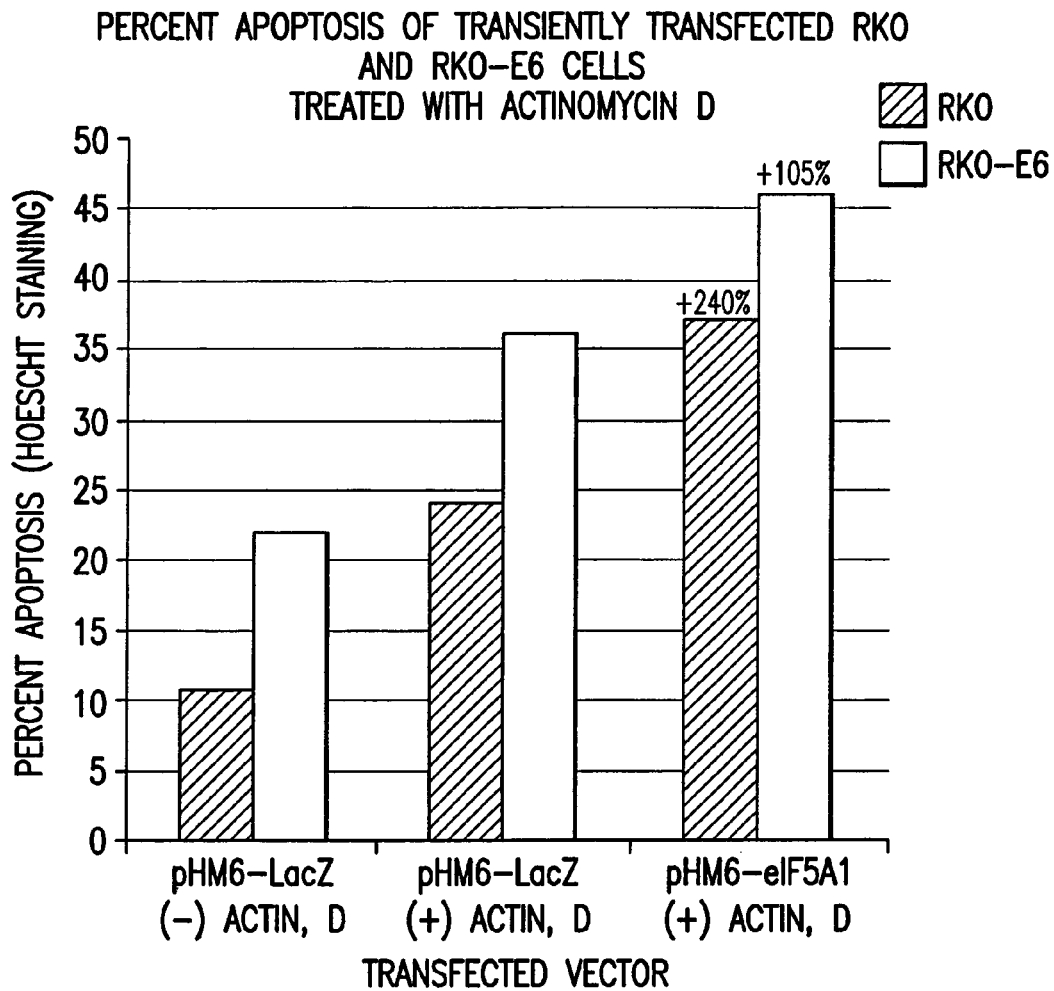
FIG. 39 is a graph depicting the percentage of apoptosis occurring in RKO and RKO-E6 cells following transient transfection. RKO and RKO-E6 cells were transiently transfected with pHM6-LacZ or pHM6-eIF5A1. RKO cells treated with Actinomycin D and transfected with pHM6-eIF5A1 showed a 240% increase in apoptosis relative to cells transfected with pHM6-LacZ that were not treated with Actinomycin D. RKO-E6 cells treated with Actinomycin D and transfected with pHM6-eIF5A1 showed a 105% increase in apoptosis relative to cells transfected with pHM6-LacZ that were not treated with Actinomycin D

FIG. 39 shows a graph depicting the percentage of apoptosis occurring in RKO and RKO-E6 cells following transient transfection. RKO and RKO-E6 cells were transiently transfected with pHM6-LacZ or pHM6-eIF5A1. 24 hours later, the cells were treated either with 0.25 µg/ml Actinomycin D or an equivalent volume of methanol (control). The cells were stained with Hoescht 20 hours later and were viewed under a fluorescent microscope using a UV filter. Cells that stained brightly due to condensed chromatin were scored as apoptotic. The experiments above reveal that RKO cells treated with Actinomycin D and transfected with pHM6-eIF5A1 showed a 240% increase in apoptosis relative to cells transfected with pHM6-LacZ that were not treated with Actinomycin D. RKO-E6 cells treated with Actinomycin D and transfected with pHM6-eIF5A1 showed a 105% increase in apoptosis relative to cells transfected with pHM6-LacZ that were not treated with Actinomycin D.

Figure 40:
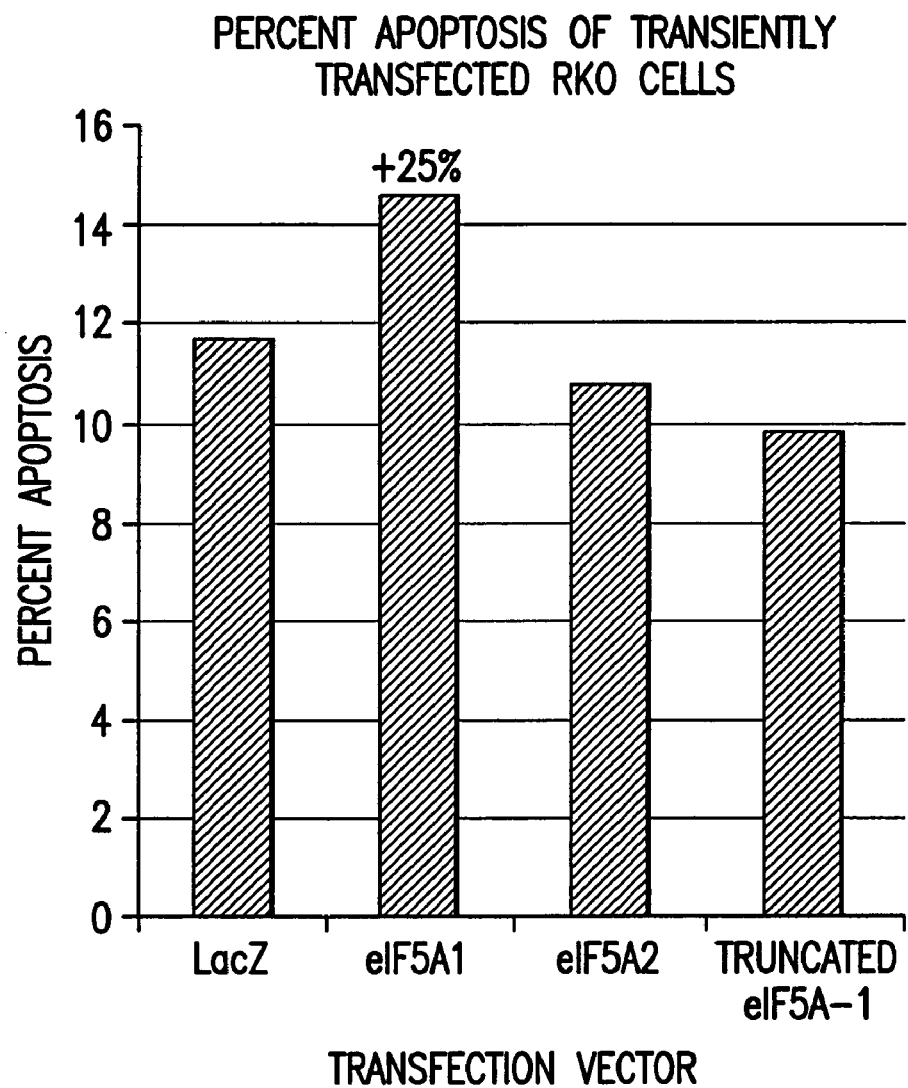
FIG. 40 is a graph depicting the percentage of apoptosis occurring in RKO cells following transient transfection. RKO cells were transiently transfected with pHM6-LacZ, pHM6-eIF5A1, pHM6-eIF5A2, or pHM6-truncated eIF5A1. Cells transfected with pHM6-eIF5A1 showed a 25% increase in apoptosis relative to control cells transfected with pHM6-LacZ. This increase was not apparent for cells transfected with pHM6-eIF5A2 or pHM6-truncated eIF5A1.

FIG. 40 provides a graph depicting the percentage of apoptosis occurring in RKO cells following transient transfection. RKO cells were transiently transfected with pHM6-LacZ, pHM6-eIF5A1, pHM6-eIF5A2, or pHM6-truncated eIF5A1. The cells were stained with Hoescht 44 hours later and were viewed under a fluorescent microscope using a UV filter. Cells that stained brightly due to condensed chromatin were scored as apoptotic. Cells transfected with pHM6-eIF5 µl showed a 25% increase in apoptosis relative to control cells transfected with pHM6-LacZ. This increase was not apparent for cells transfected with pHM6-eIF5A2 or pHM6-truncated eIF5A1.

Figure 41:
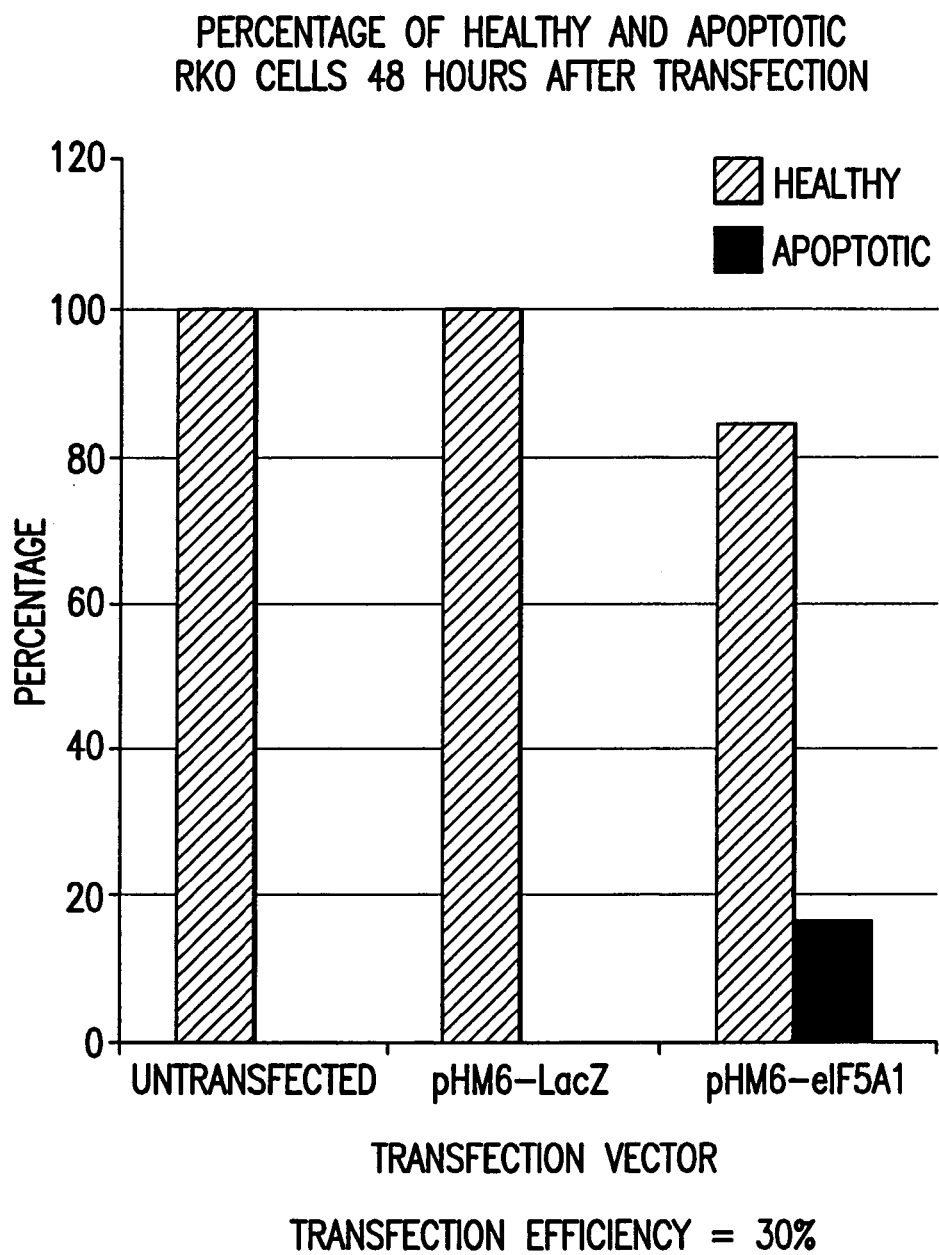
FIG. 41 is a graph depicting the percentage of apoptosis occurring in RKO cells following transient transfection. RKO cells were either left untransfected or were transiently transfected with pHM6-LacZ or pHM6-eIF5A1. After correction for transfection efficiency, 60% of the cells transfected with pHM6-eIF5A1 were apoptotic.

FIG. 41 provides a graph depicting the percentage of apoptosis occurring in RKO cells following transient transfection. RKO cells were either left untransfected or were transiently transfected with pHM6-LacZ or pHM6-eIF5A1. The cells were stained with Hoescht 44 hours later and were viewed under a fluorescent microscope using a UV filter. Cells that stained brightly due to condensed chromatin were scored as apoptotic. After correction for transfection efficiency, 60% of the cells transfected with pHM6-eIF5A1 were apoptotic.

Figures 42A, 42B:
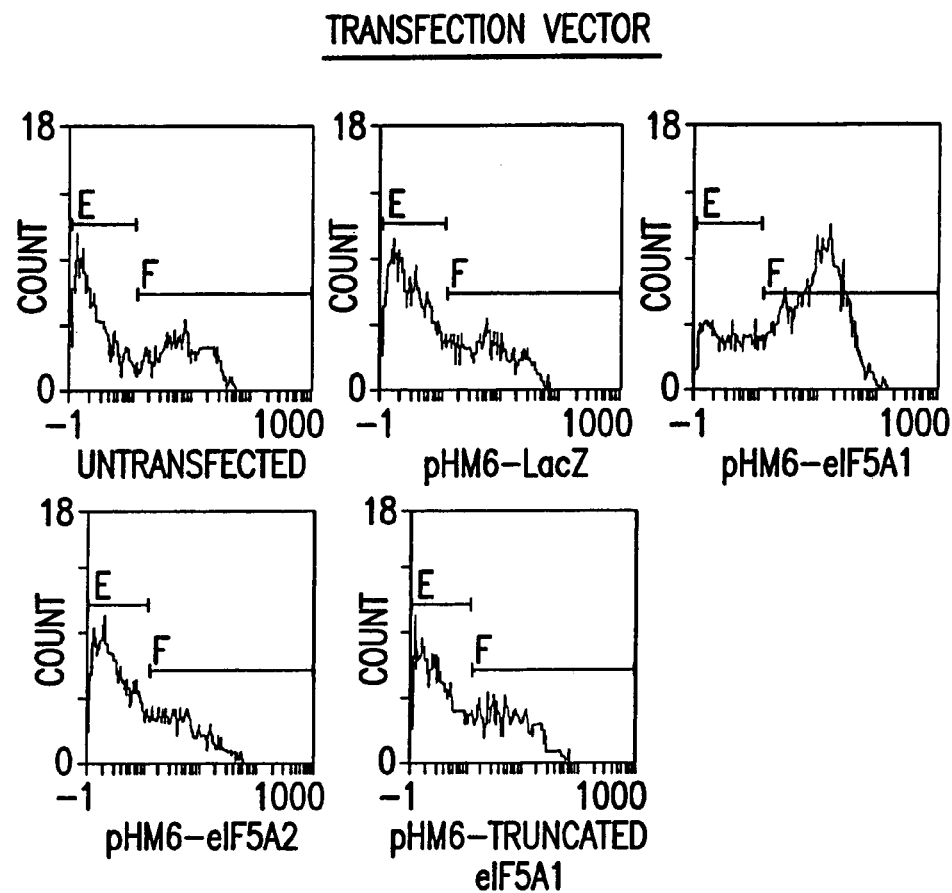
FIG. 42 provides the results of a flow cytometry analysis of RKO cell apoptosis following transient transfection. RKO cells were either left untransfected or were transiently transfected with pHM6-LacZ, pHM6-eIF5A1, pHM6-eIF5A2, or pHM6-truncated eIF5A1. The table depicts the percentage of cells undergoing apoptosis calculated based on the area under the peak of each gate. After correction for background apoptosis in untransfected cells and for transfection efficiency, 80% of cells transfected with pHM6-eIF5A1 exhibited apoptosis. Cells transfected with pHM6-LacZ, pHM6-eIF5A2 or pHM6-truncated eIF5A1 exhibited only background levels of apoptosis.

FIG. 42 provides flow cytometry analysis of RKO cell apoptosis following transient transfection. RKO cells were either left untransfected or were transiently transfected with pHM6-LacZ, pHM6-eIF5A1, pHM6-eIF5A2, or pHM6-truncated eIF5A1. 48 hours later the cells were harvested and fixed. Fragmented DNA reflecting apoptosis was labeled with fluorescein-conjugated deoxynucleotides and analyzed on a flow cytometer equipped with a 488 nm argon ion laser source. Fluorescence occurring under gate E is from non-apoptotic cells, and fluorescence occurring under gate F is from cells undergoing apoptosis. The table depicts the percentage of cells undergoing apoptosis calculated based on the area under the peak of each gate. After correction for background apoptosis in untransfected cells and for transfection efficiency, 80% of cells transfected with pHM6-eIF5A1 exhibited apoptosis. Cells transfected with pHM6-LacZ, pHM6-eIF5A2 or pHM6-truncated eIF5A1 exhibited only background levels of apoptosis.

Figure 43:
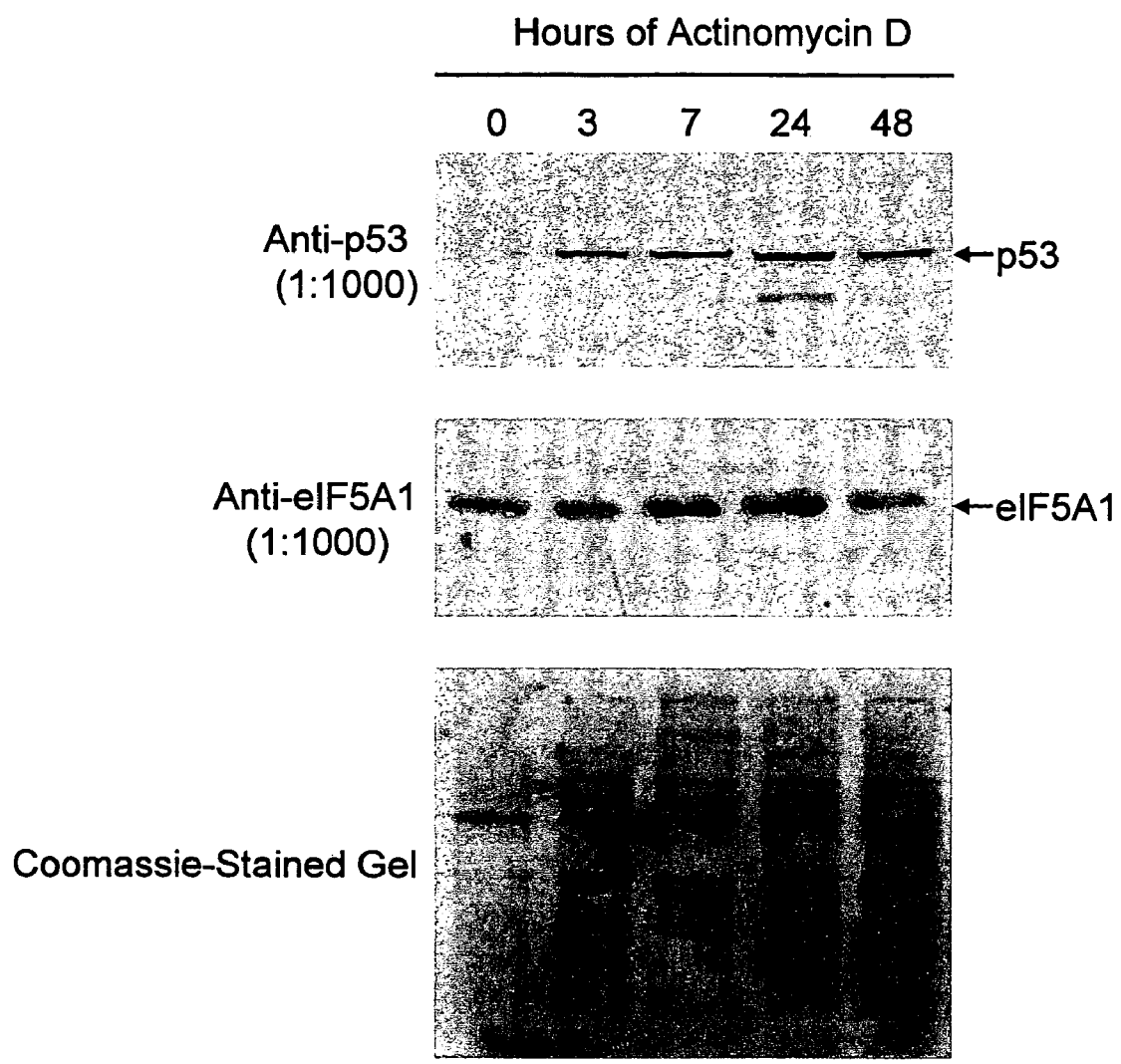
FIG. 43 provides Western blots of protein extracted from RKO cells treated with 0.25 µg/ml Actinomycin D for 0, 3, 7, 24, and 48 hours. The top panel depicts a Western blot using anti-p53 as the primary antibody. The middle panel depicts a Western blot using anti-eIF5A1 as the primary antibody. The bottom panel depicts the membrane used for the anti-eIF5A1 blot stained with Coomassie blue following chemiluminescent detection to demonstrate equal loading. p53 and eIF5A1 are both upregulated by treatment with Actinomycin D.
Figure 44:
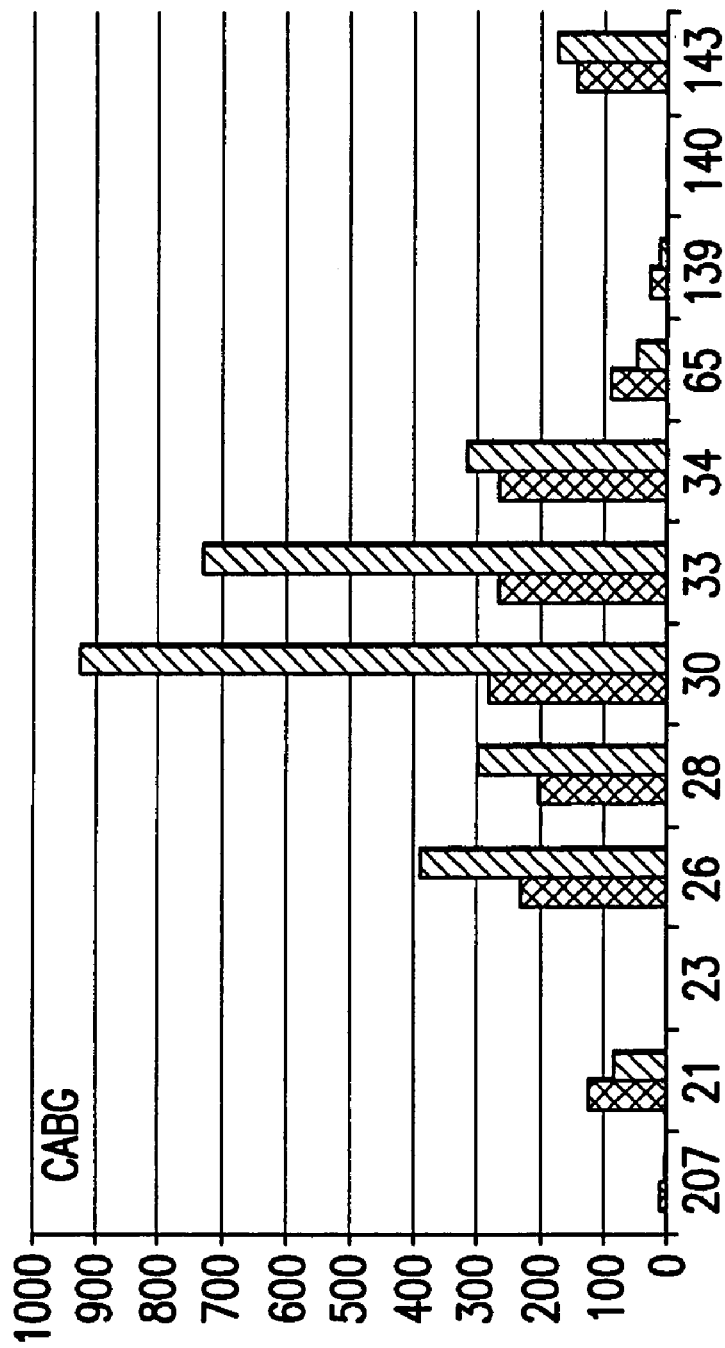
FIG. 44 is a bar graph showing that both apoptosis-specific eIF-5A (eIF5a) and proliferation eIF-5A (eIF5b) are expressed in heart tissue. The heart tissue was taken from patients receiving coronary artery bypass grafts (CABG). Gene expression levels of eIF5a (light gray bar) are compared to eIF5b (dark gray bar). The X-axis are patient identifier numbers. The Y-axis is pg/ng of 18s (picograms of message RNA over nanograms of ribosomal RNA 18S).
Figure 45:
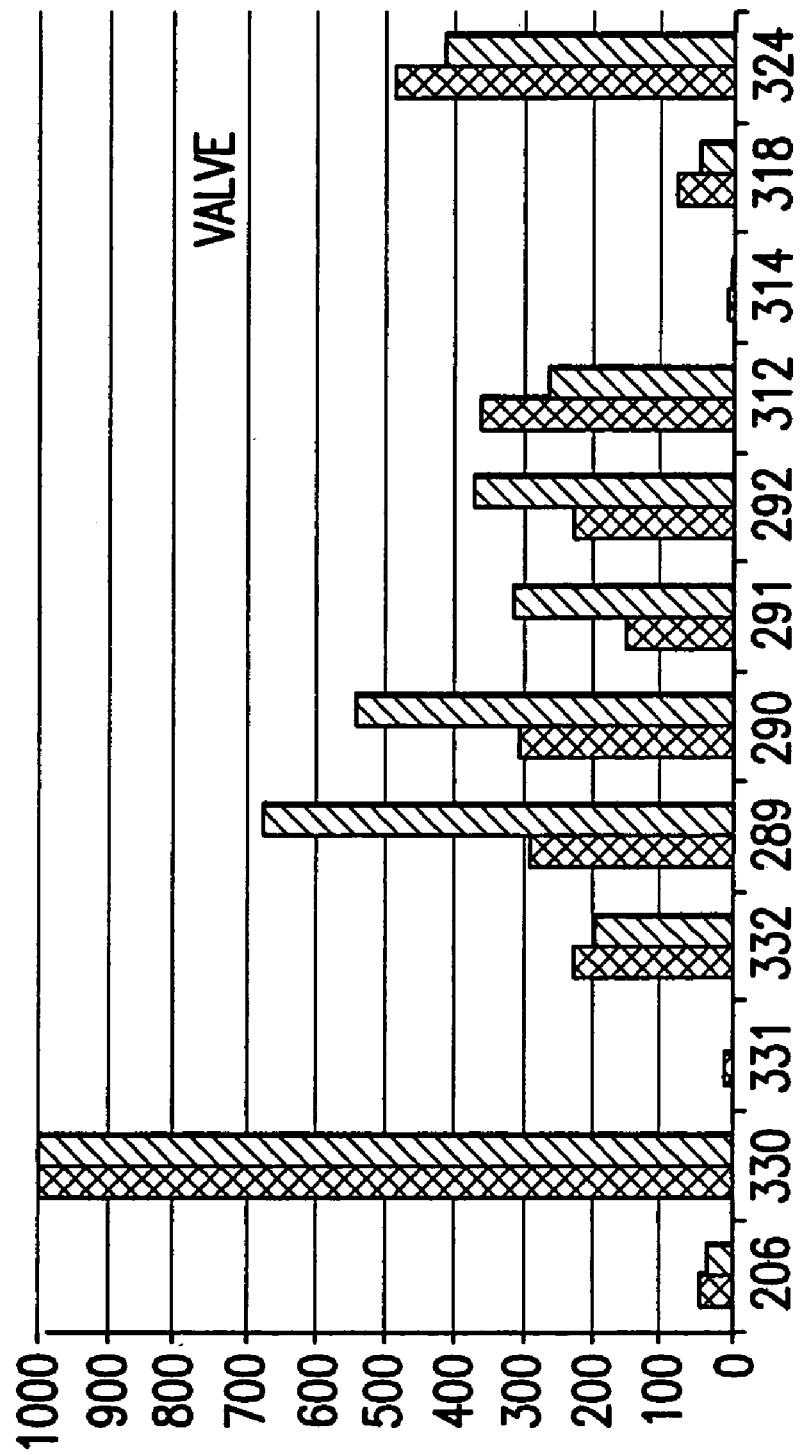
FIG. 45 is a bar graph showing that both apoptosis-specific eIF-5A (eIF5a) and proliferation eIF-5A (eIF5b) are expressed in heart tissue. The heart tissue was taken from patients receiving valve replacements. Gene expression levels of eIF5a (light gray bar) are compared to eIF5b (dark gray bar). The X-axis are patient identifier numbers. The Y-axis is pg/ng of 18s (picograms of message RNA over nanograms of ribosomal RNA 18S).

FIG. 43 provides Western blots of protein extracted from RKO cells treated with 0.25 μg/ml Actinomycin D for 0, 3, 7, 24, and 48 hours. 5 μg (for anti-eIF5A1) *or* 10 μg (for anti-p53) of total protein was separated on a 12% SDS-polyacrylamide gel and transferred to a polyvinylidene difluoride membrane. The top panel depicts a Western blot using anti-p53 as the primary antibody. The middle panel depicts a Western blot using anti-eIF5A1 as the primary antibody. The bottom panel depicts the membrane used for the anti-eIF5A1 blot stained with Coomassie blue following chemiluminescent detection to demonstrate equal loading. p53 and eIF5A1 are both upregulated by treatment with Actinomycin D.

Example 6

Figure 47:
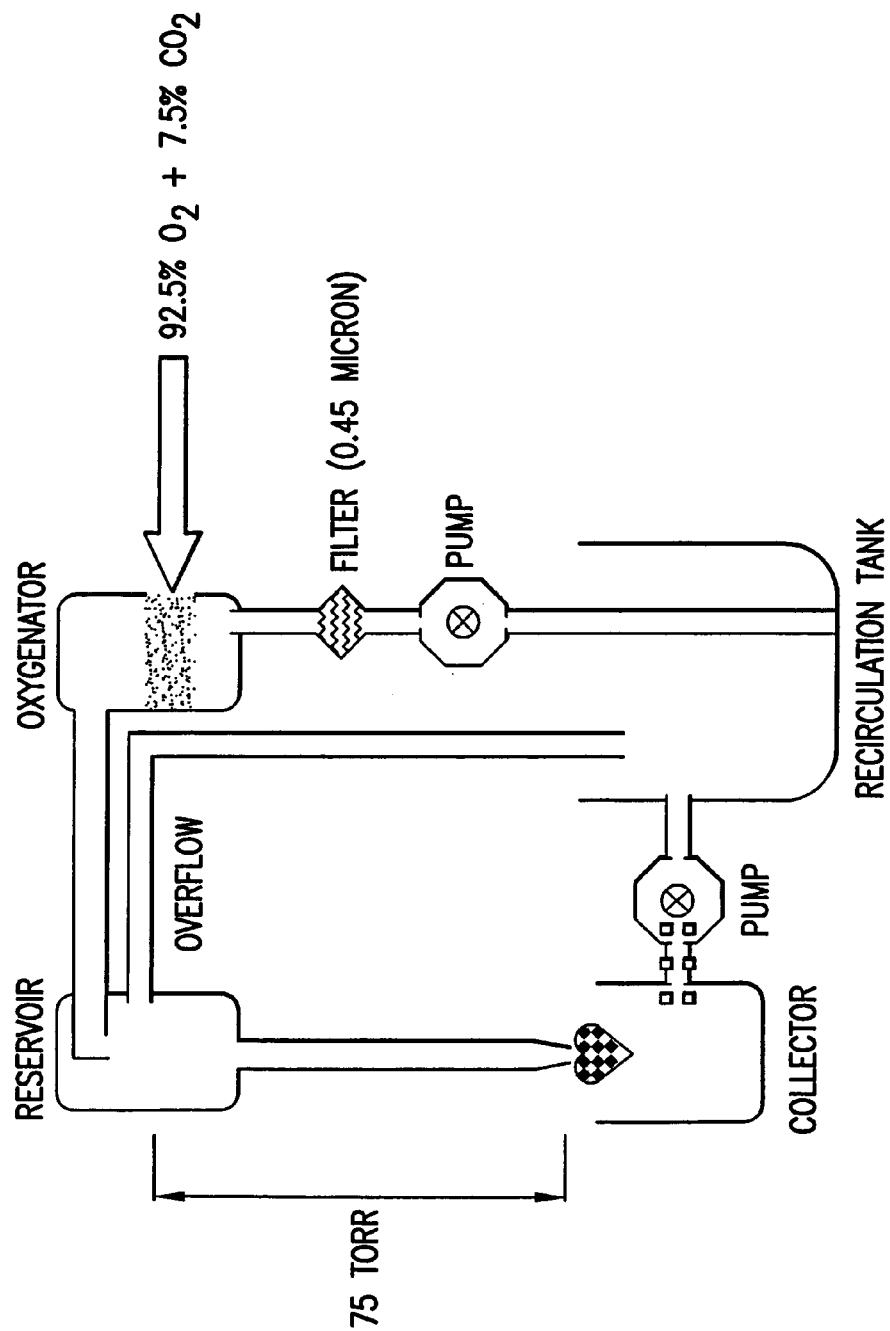
FIG. 47 depicts schematically an experiment performed on heart tissue. The heart tissue was exposed to normal oxygen levels and the expression levels of apoptosis-specific eIF-5A (eIf5a) and proliferating eIF-5A (eIF5b) measured. Later, the amount of oxygen delivered to the heart tissue was lowered, thus inducing hypoxia and ischemia, and ultimately, a heart attack in the heart tissue. The expression levels of apoptosis-specific eIF-5A (eIF5a) and proliferating eIF-5A (eIF5b) were measured and compared to the expression levels of the heart tissue before it was damaged by ischemia.
Figure 49:
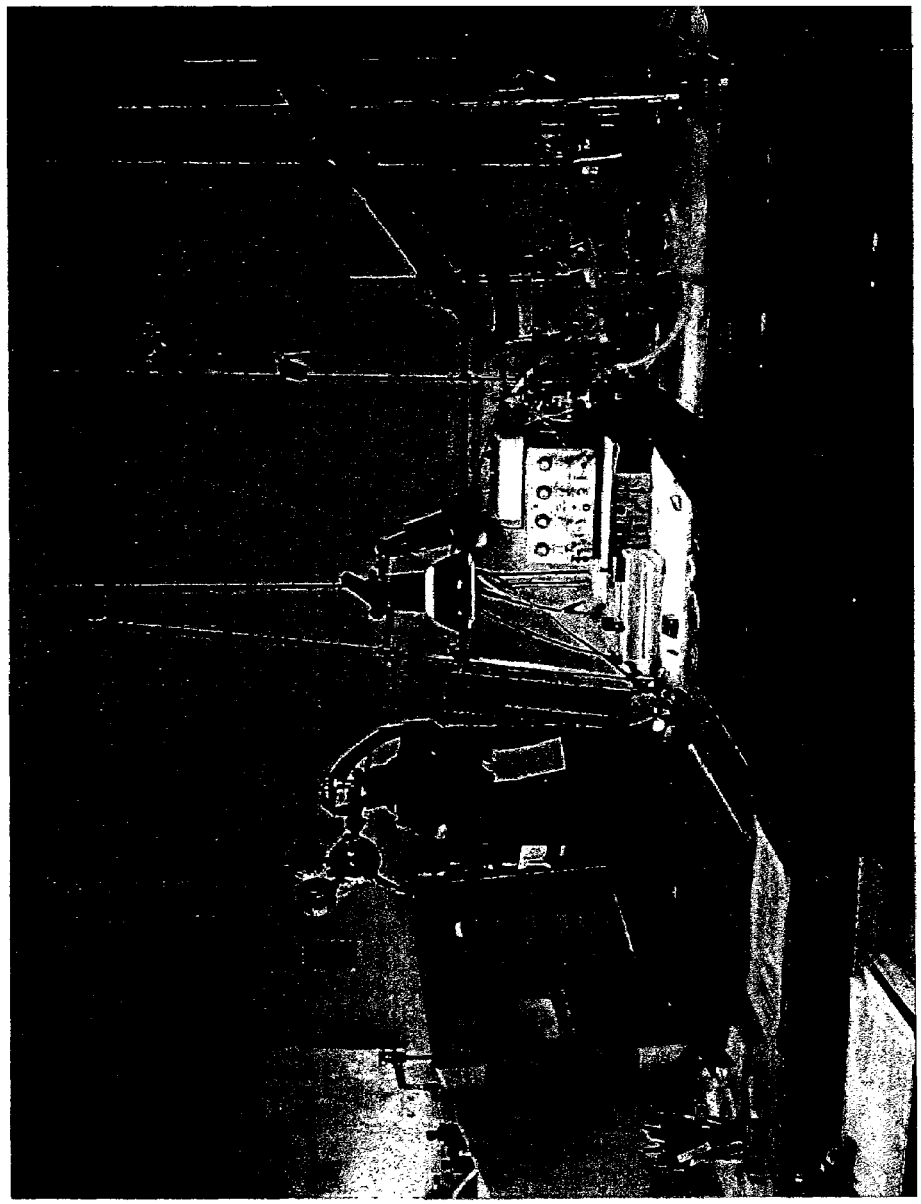
FIG. 49 shows the lab bench with the set up of the experiment depicted in FIG. 47.
Figure 50C:
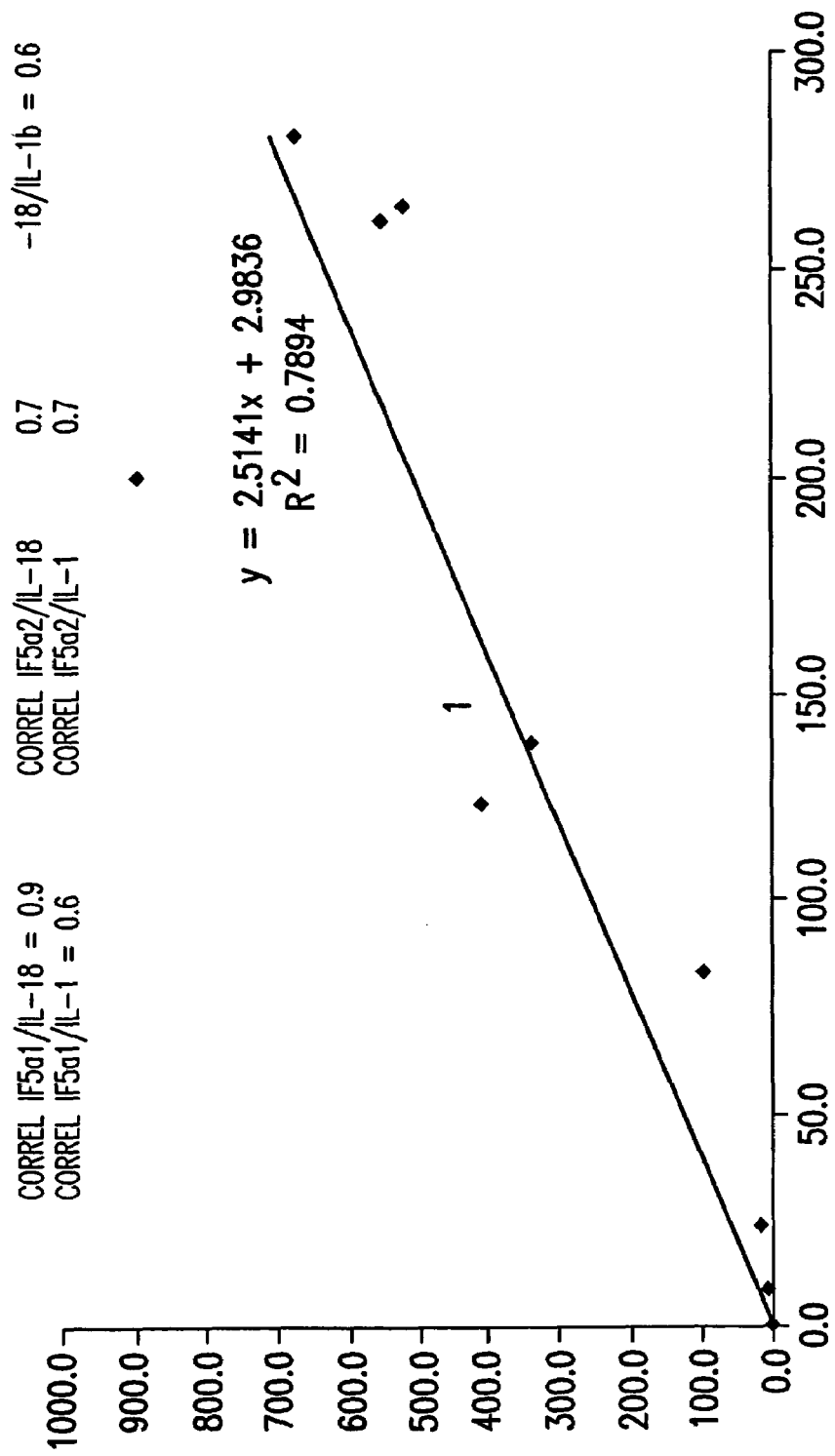
Figure 50D:
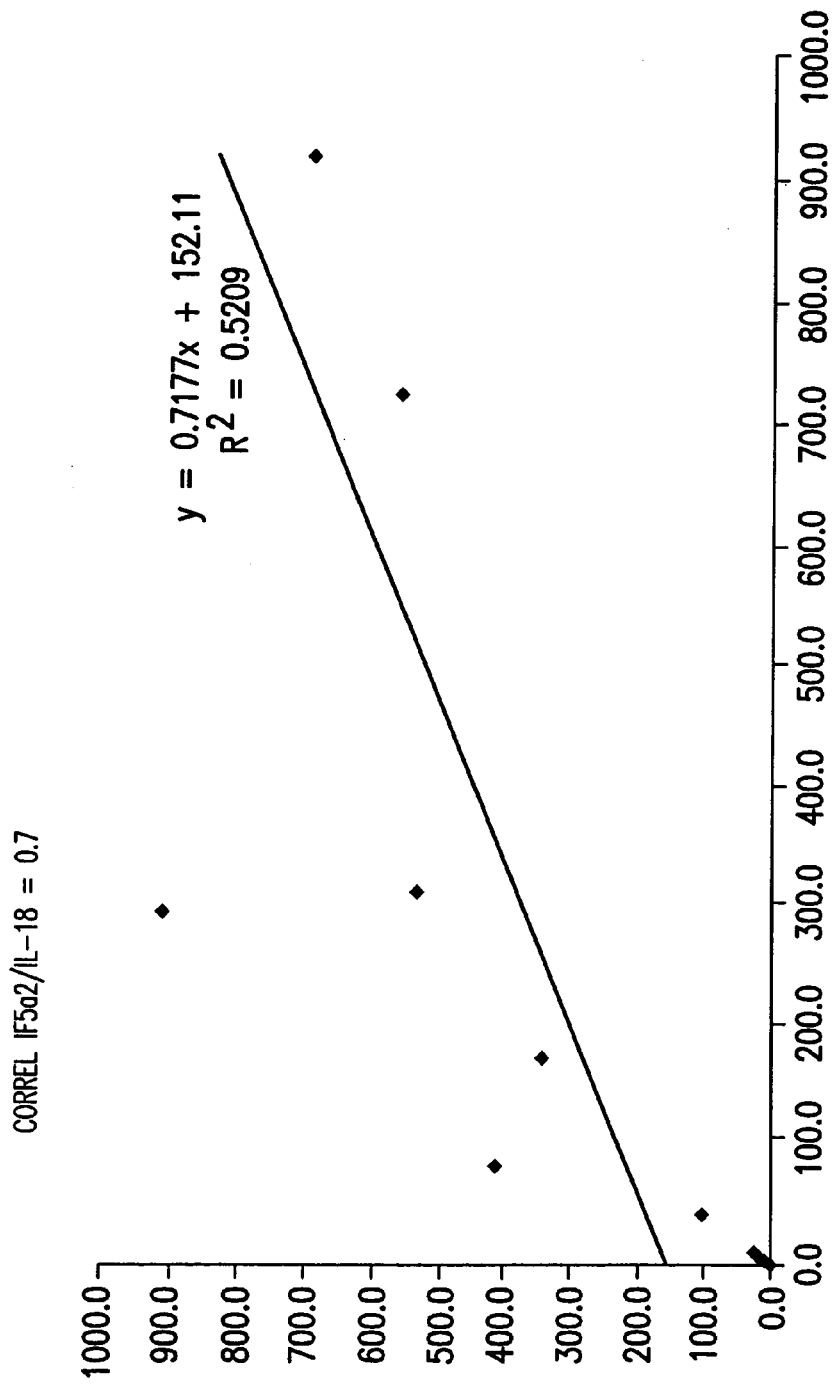
Figure 50E:
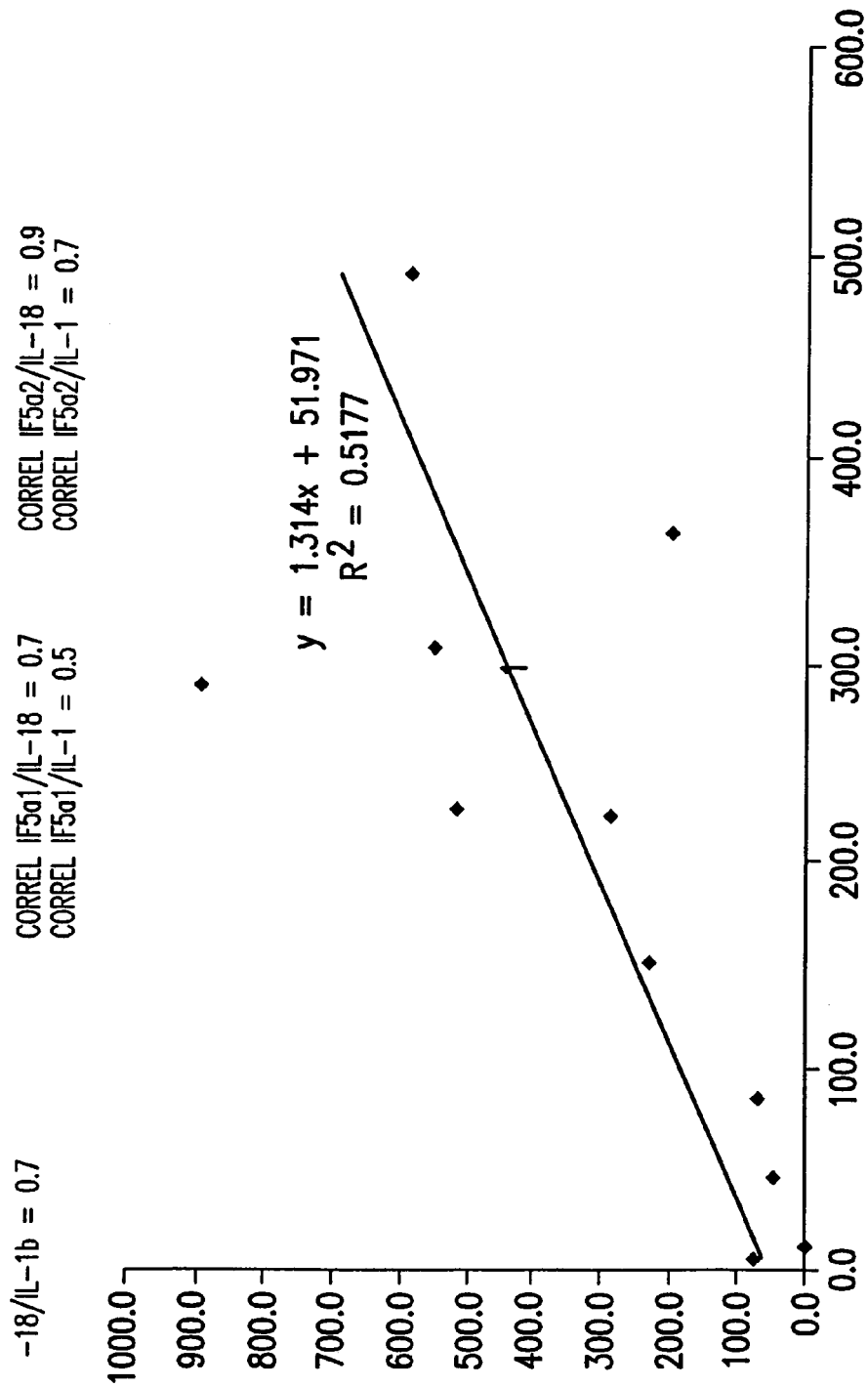
Figure 50F:
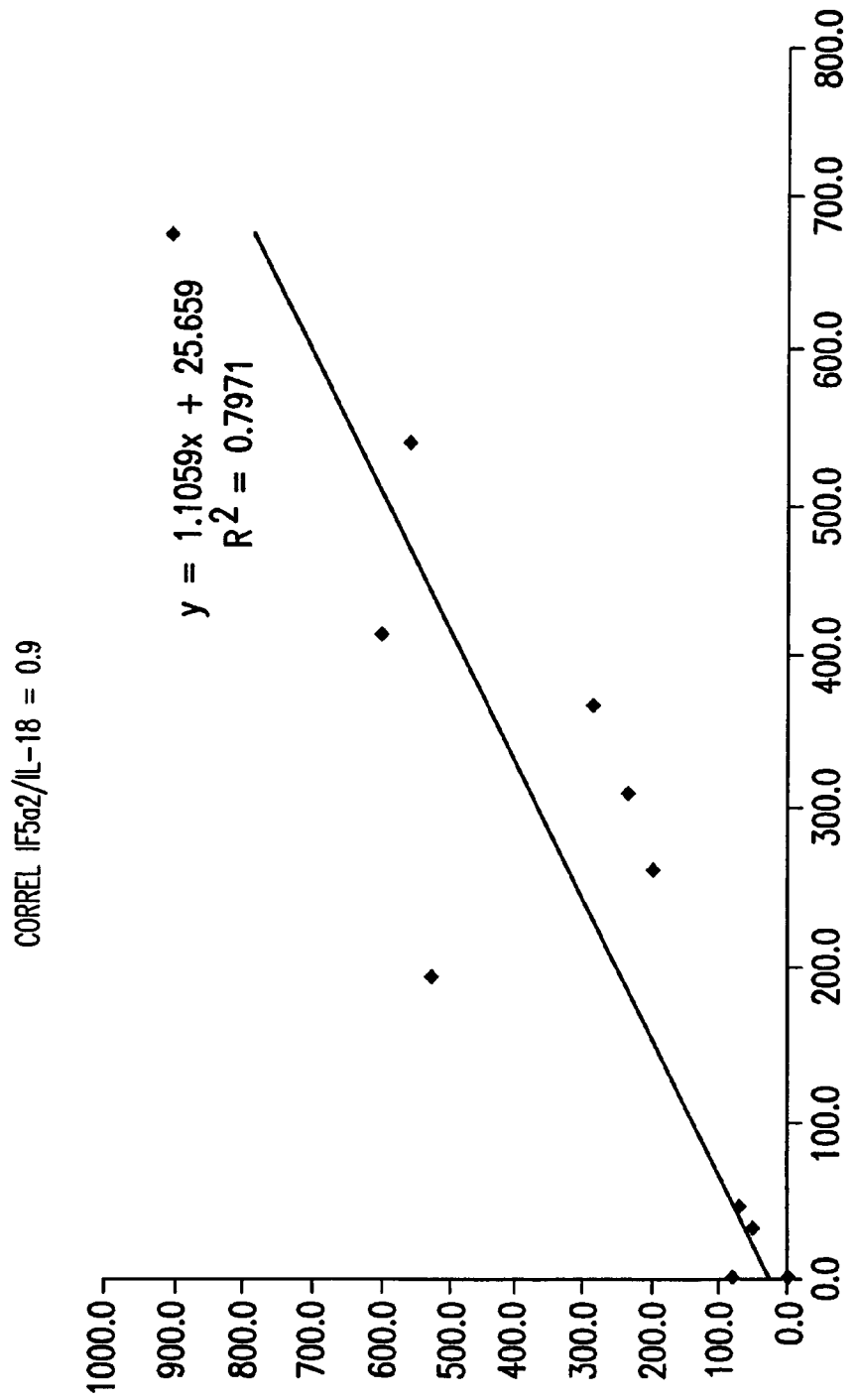
Figure 52:
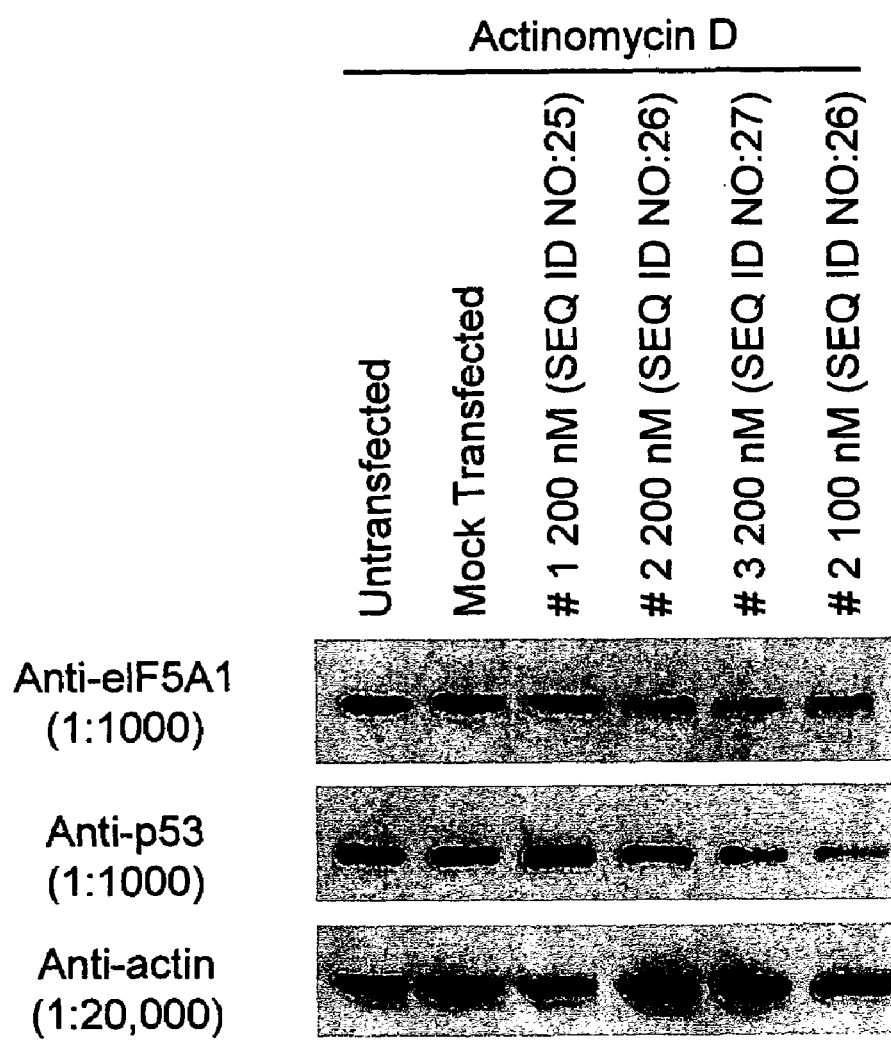
FIG. 52 shows that the antisense oligonucleotides of SEQ ID NO:25 and 26 have supressed the expression of apoptosis-specific eIF5A1. RKO cells were either left untransfected, mock transfected, or transfected with 200 nM of anti sense oligonucleotides to apoptosis specific eIF5A1 SEQ ID NO:25, 26, or 27. RKO cells were also transfected with 100 nM of antisense oligonucleotide eIF5A1 26. Forty-eight hours after transfection, the cells were treated with 0.25 µg/ml Actinomycin D. Twenty-four hours later, the cell extract was harvested and 5 µg of protein from each sample was separated on a SDS-PAGE gel, transferred to a PVDF membrane, and Western blotted with an antibody against eIF5A1. After chemiluminescent detection, the membrane was stripped and re-blotted with an antibody against p53. After chemiluminescent detection, the membrane was stripped again and re-blotted with an antibody against actin.
Figure 53A:
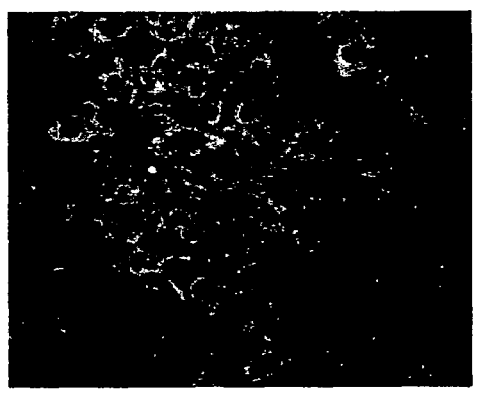
FIG. 53 shows that antisense oligonucleotides targeted against human apoptosis specific eIF5A1 were delivered into human lamina cribosa cells. The lamina cribosa cell line # 506 was either transfected with 100 nM of FITC-labeled antisense oligonucleotide using Oligofectamine transfection reagent (FIG. 53A) or transfected with 10 µM of naked FITC-labeled antisense oligonucleotide diluted directly in serum-free media (FIG. 53B). After 24 hours fresh media containing 10% FBS and fresh antisense oligonucleotide diluted to 10 µM was added to the cells. The cells in both FIGS. 53 (A) and (B), were fixed after a total of 48 hours and visualized on a fluorescent microscope under UV light using a fluorescein filter.
Figure 53B:
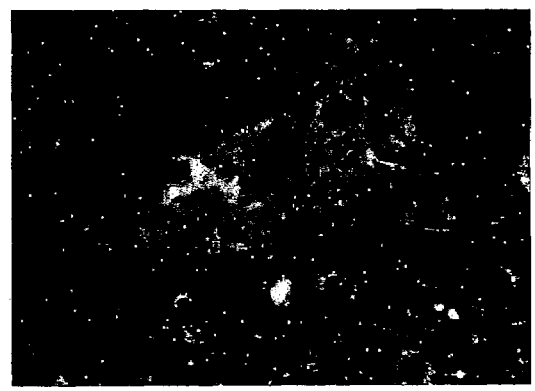
Figure 54:
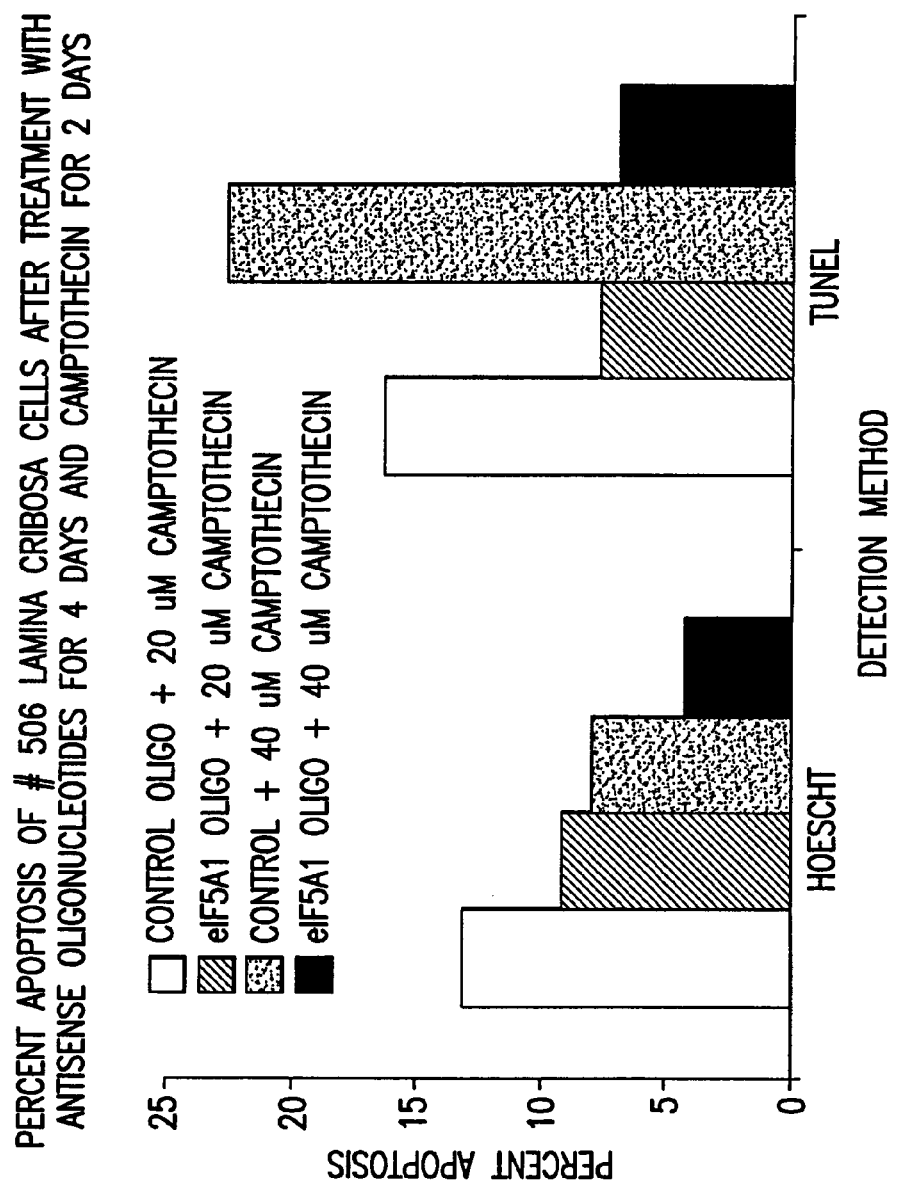
FIG. 54 shows the results of an study where the lamina cribosa cell line # 506 was transfected with 10 µM of either the control antisense oligonucleotide or antisense oligonucleotide eIF5A1 SEQ ID NO:26 for a total of 4 days. Forty-eight hours after beginning antisense oligonucleotide treatment, the cells were treated with either 20 µM or 40 µM camptothecin for 48 hours. Antisense oligonucleotide and camptothecin-containing media was changed daily. The percentage of apoptotic cells was determined by labelling the cells with Hoescht and TUNEL.
Figure 55:
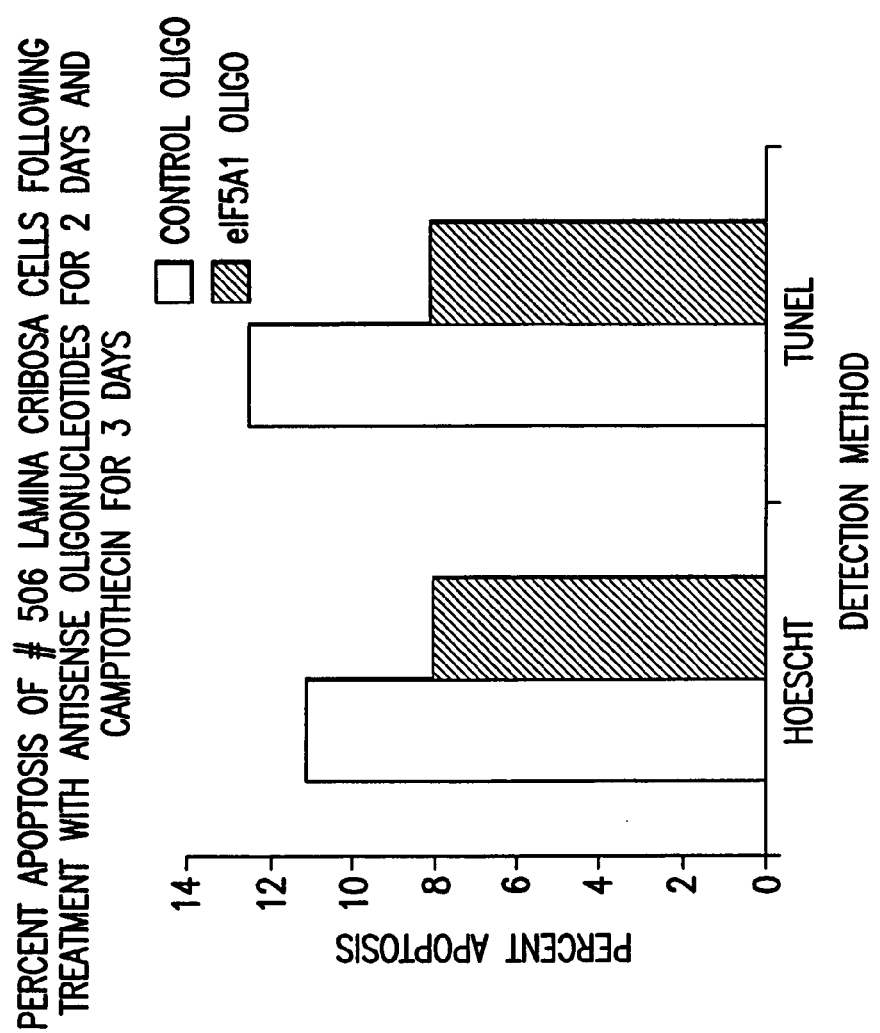
FIG. 55 shows the results of a study where the lamina cribosa cell line # 506 was transfected with 10 µM of either the control antisense oligonucleotide or antisense oligonucleotide eIF5A1 SEQ ID NO:26. Twenty-four hours later the media was changed and fresh antisense oligonucleotides were added. Forty-eight hours after beginning antisense oligonucleotide treatment, the antisense-oligonucleotides were removed and the cells were treated with 20 µM camptothecin for 3 days. The camptothecin-containing media was changed daily. The percentage of apoptotic cells was determined by labelling the cells with Hoescht and TUNEL.
Figure 56:
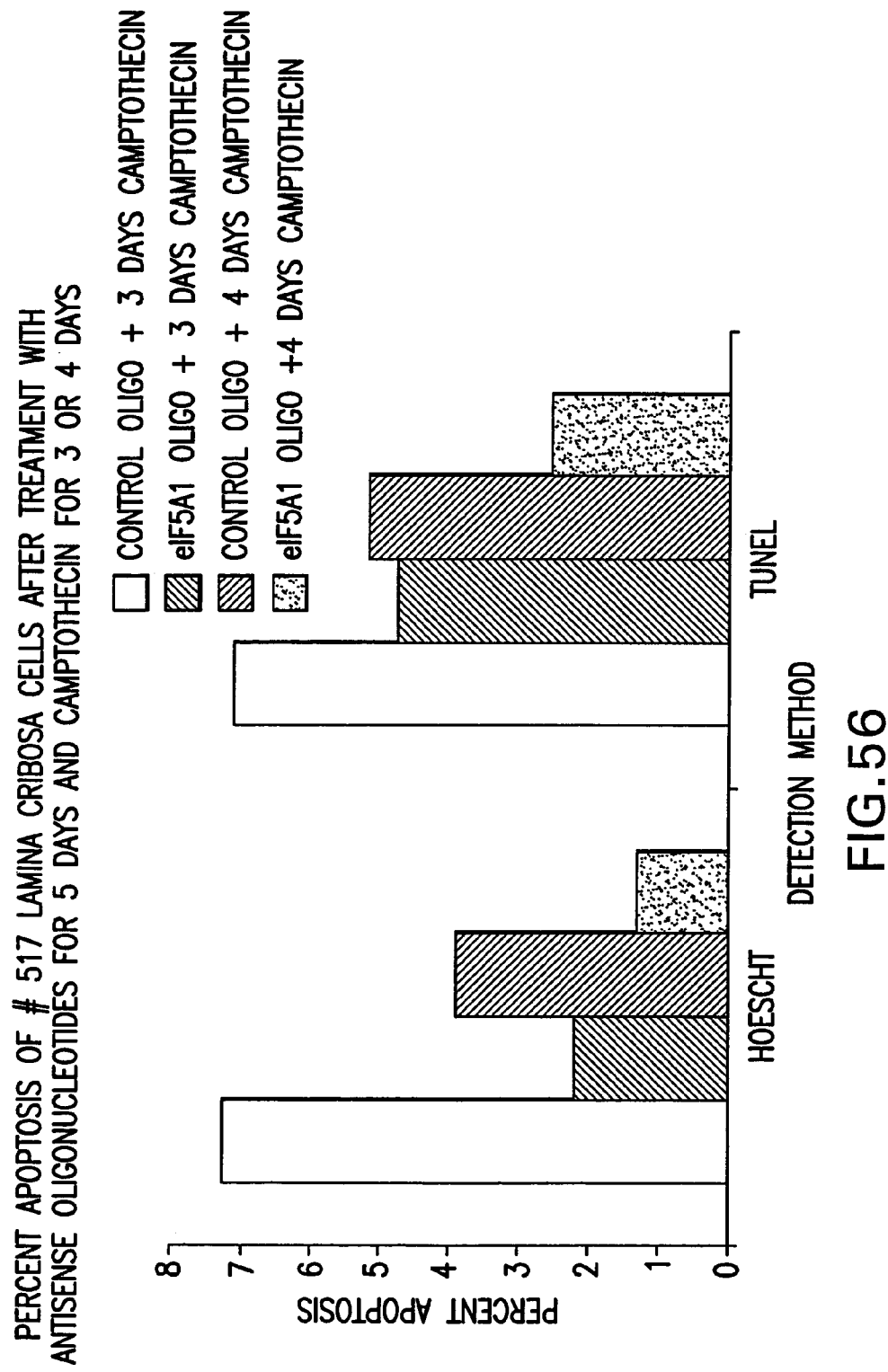
FIG. 56 shows the results of study where the lamina cribosa cell line # 517 was transfected with 1 µM of either the control antisense oligonucleotide or antisense oligonucleotide eIF5A1 SEQ ID NO:26 for a total of five days. Forty-eight hours after beginning antisense oligonucleotide treatment, the cells were treated with 20 µM camptothecin for either 3 or 4 days. Antisense oligonucleotide and camptothecin-containing media was changed daily. The percentage of apoptotic cells was determined by labelling the cells with Hoescht and TUNEL.
Figure 57:
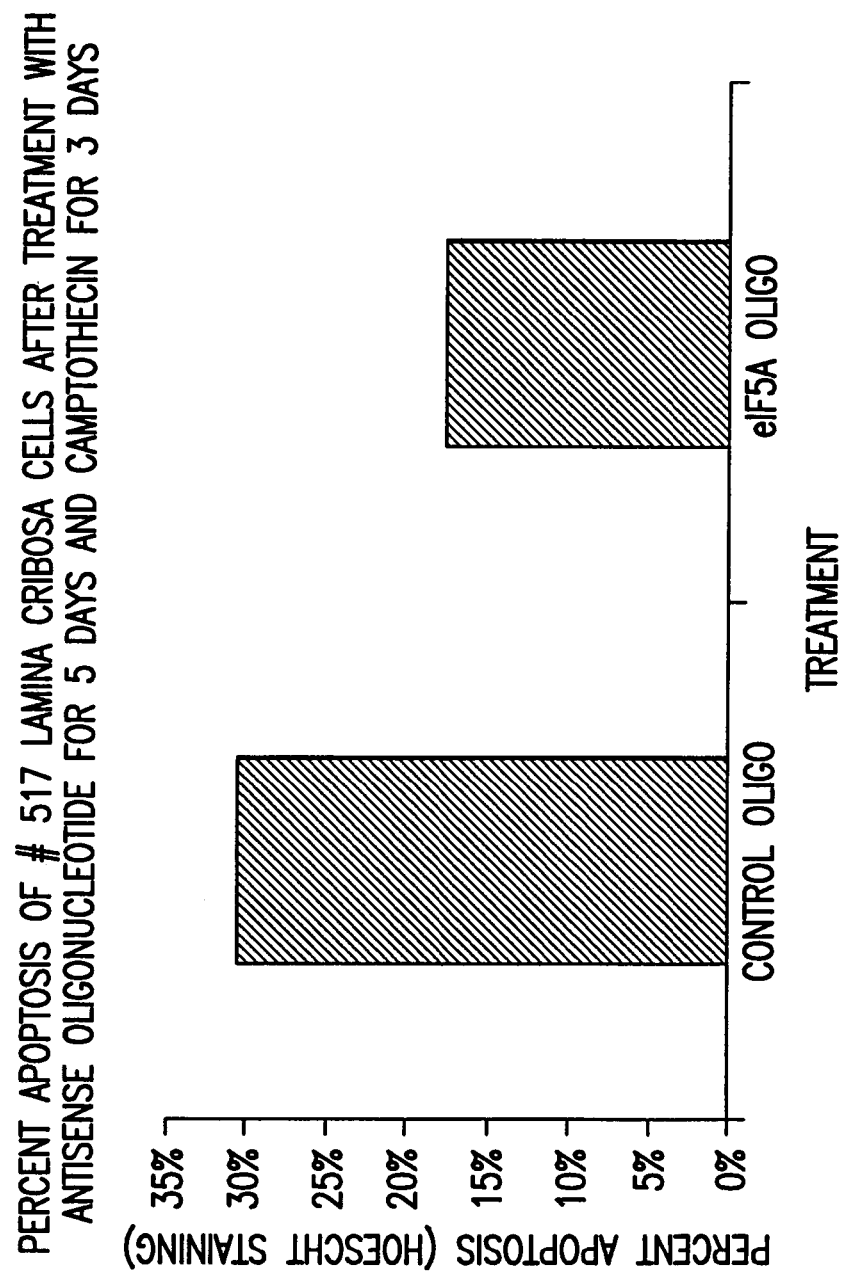
FIG. 57 shows the results of a study where the lamina cribosa cell line # 517 was transfected with 2.5 µM of either the control antisense oligonucleotide or antisense oligonucleotide eIF5A1 SEQ ID NO:26 for a total of five days. Forty-eight hours after beginning antisense oligonucleotide treatment, the cells were treated with 40 µM camptothecin for 3 days. Antisense oligonucleotide and camptothecin-containing media was changed daily. The percentage of apoptotic cells was determined by labelling the cells with Hoescht and TUNEL.

FIG. 47 depicts an experiment run on heart tissue to mimic the beating of a human heart and the subsequent induced heart attack. FIG. 49 shows the laboratory bench set up. A slice of human heart tissue removed during valve replacement surgery was hooked up to electrodes. A small weight was attached to the heart tissue to ease in measuring the strength of the heart beats. The electrodes provided an electrical stimulus to get the tissue to start beating. The levels of gene expression for both apoptosis-specific eIF-5A (eIF-5a) and proliferating eIF-5A (eIF5b) were measured in the heart tissue before ischemia was induced. See FIG. 46. In the pre-ischemic heart tissue low levels of both eIF-5a and 5eIFb were produced and their levels were in relative balance. During this time, oxygen and carbon dioxide were delivered in a buffer to the heart at 92.5% and 7.5%, respectively. Later, the oxygen levels was reduced and the nitrogen levels was increased, to induce ischemia and finally a "heart attack." The heart tissue stopped beating. The oxygen levels were then returned to normal, the heart tissue was pulsed again with an electrical stimulus to start the heart beating again. After the "heart attack" the expression levels of apoptosis-specific eIF-5a and proliferating eIF-5A (eIF5b) were again measured. This time, there was a significant increase in the level of expression of the apoptosis-specific eIF-5A levels, whereas the increase in the level of expression of proliferating eIF-5A (eIF5b) was noticeably less. See FIG. 46.

After the "heart attack" the heart did not beat as strong, as indicated by less compression/movement of the attached weight, thus indicating that the heart tissue cells were being killed rapidly due to the presence of apoptosis-specific eIF-5A.

Figure 48:
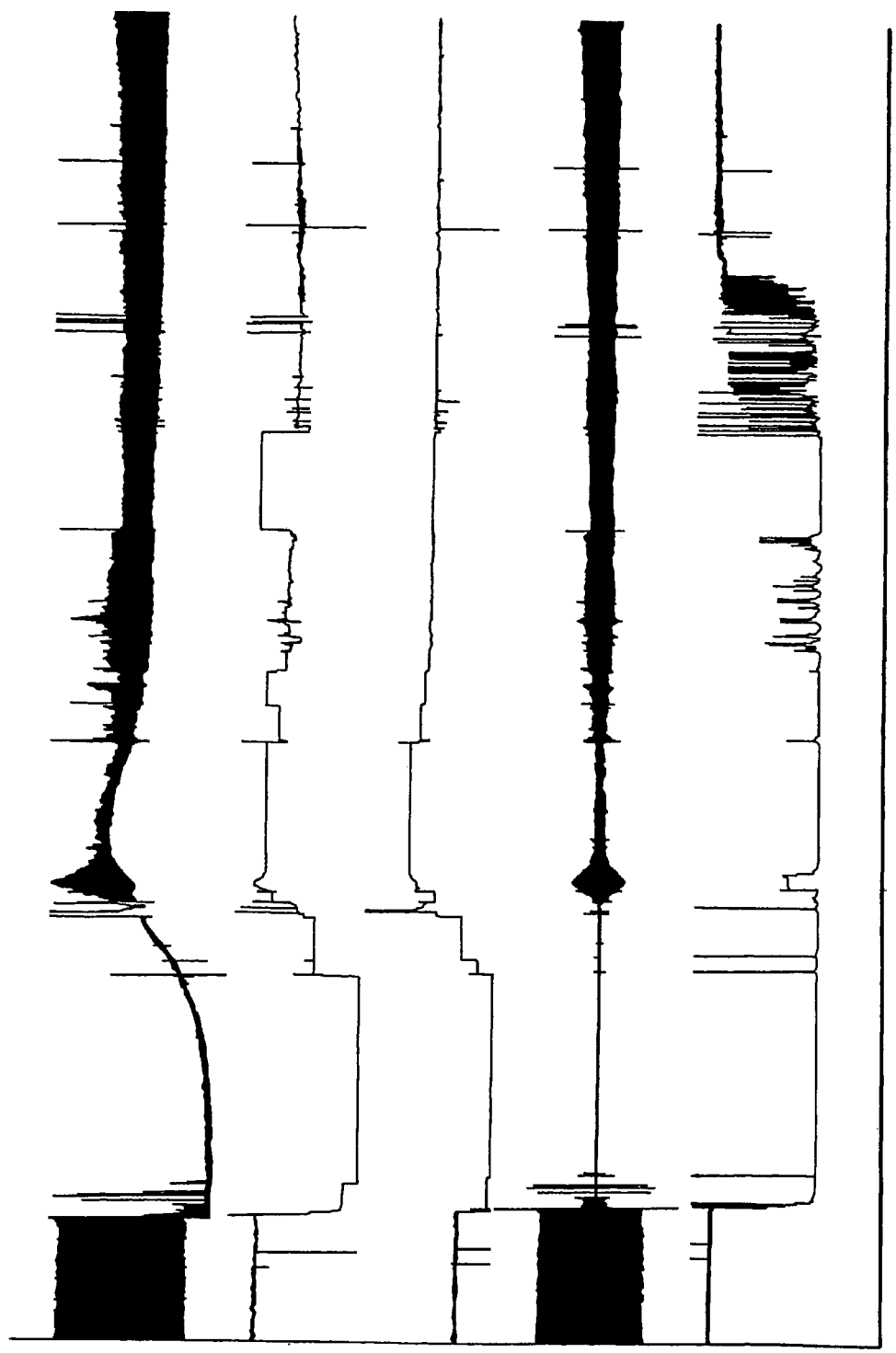
FIG. 48 shows EKGs of heart tissue before and after the ischemia was induced.

The EKG results are depicted in FIG. 48. On the left side of the panels a normal heart beat is shown (the pre-ischemic heart tissue). After the "heart attack" (straight line), and the re-initiation of the heart beat, the EKG shows decreased activity due to muscle cell death. The EKG shows relative loss in strength of heart beat.

Example 7

This example shows suppressed expression of apoptosis-specific eIF5A in lamina cribosa cells using antisense oligonucleotides targeted to apoptosis-specific eIF5A. It also shows reducing apoptosis in lamina cribosa cells using antisense oligonucleotides targeted to apoptosis-specific eIF5A (eIF5A1).

Human Lamina Cribosa and Astrocyte Culture

Paired human eyes were obtained within 48 hours post mortem from the Eye Bank of Canada, Ontario Division. Optic nerve heads (with attached pole) were removed and placed in Dulbecco's modified Eagle's medium (DMEM) supplemented with antibiotic/antimycotic, glutamine, and 10% FBS for 3 hours. The optic nerve head (ONH) button was retrieved from each tissue sample and minced with fine dissecting scissors into four small pieces. Explants were cultured in 12.5 cm$^2$ plastic culture flasks in DMEM medium. Growth was observed within one month in viable explants. Once the cells reached 90% confluence, they were trypsinized and subjected to differential subculturing to produce lamina cribrosa (LC) and astrocyte cell populations. Specifically, LC cells were subcultured in 25 cm$^2$ flasks in DMEM supplemented with gentamycin, glutamine, and 10% FBS, whereas astrocytes were expanded in 25 cm$^2$ flasks containing EBM complete medium (Clonetics) with no FBS. FBS was added to astrocyte cultures following 10 days of subculture. Cells were maintained and subcultured as per this protocol.

Cell populations obtained by differential subculturing were characterized for identity and population purity using differential fluorescent antibody staining on 8 well culture slides. Cells were fixed in 10% formalin solution and washed three times with Dulbecco's Phosphate Buffered Saline (DPBS). Following blocking with 2% nonfat milk in DPBS, antibodies were diluted in 1% BSA in DPBS and applied to the cells in 6 of the wells. The remaining two wells were treated with only 1% bovine serum albumin (BSA) solution and no primary antibody as controls. Cells were incubated with the primary antibodies for one hour at room temperature and then washed three times with DPBS. Appropriate secondary antibodies were diluted in 1% BSA in DPBS, added to each well and incubated for 1 hour. Following washing with DPBS, the chambers separating the wells of the culture slide were removed from the slide, and the slide was immersed in double distilled water and then allowed to air-dry. Fluoromount (Vector Laboratories) was applied to each slide and overlayed by 22×60 mm coverglass slips.

Immunofluorescent staining was viewed under a fluorescent microscope with appropriate filters and compared to the control wells that were not treated with primary antibody. All primary antibodies were obtained from Sigma unless otherwise stated. All secondary antibodies were purchased from Molecular Probes. Primary antibodies used to identify LC cells were: anti-collagen I, anti-collagen IV, anti-laminin, anti-cellular fibronectin. Primary antibodies used to identify astrocytes were: anti-galactocerebroside (Chemicon International), anti-A2B5 (Chemicon International), anti-NCAM, anti-human Von willebrand Factor. Additional antibodies used for both cell populations included anti-glial fibrillary (GFAP) and anti-alpha-smooth muscle actin. Cell populations were determined to be comprised of LC cells if they stained positively for collagen I, collagen IV, laminin, cellular fibronectin, alpha smooth muscle actin and negatively for glial fibrillary (GFAP). Cell populations were determined to be comprised of astrocytes if they stained positively for NCAM, glial fibrillary (GFAP), and negatively for galactocerebroside, A2B5, human Von willebrand Factor, and alpha smooth muscle actin.

In this preliminary study, two sets of human eyes were used to initiate cultures. LC cell lines # 506 and # 517 were established from the optic nerve heads of 83 and 17-year old males, respectively. Both LC cell lines have been fully characterized and found to contain greater than 90% LC cells.

RKO Cell Culture

RKO (American Type Culture Collection CRL-2577), a human colon carcinoma cell line expressing wild-type p53, was used to test the antisense oligonucleotides for the ability to suppress eIF5A1 protein expression. RKO were cultured in Minimum Essential Medium Eagle (MEM) with non-essential amino acids, Earle's salts, and L-glutamine. The culture media was supplemented with 10% fetal bovine serum (FBS) and 100 units of penicillin/streptomycin. The cells were grown at 37° C. in a humidified environment of 5% $CO_2$ and 95% air. The cells were subcultured every 3 to 4 days by detaching the adherent cells with a solution of 0.25% trypsin and 1 mM EDTA. The detached cells were dispensed at a split ratio of 1:10 to 1:12 into a new culture dish with fresh media.

Induction of Apoptosis

Apoptosis was induced in RKO and lamina cribosa cells using Actinomycin D, an RNA polymerase inhibitor, and camptothecin, a topoisomerase inhibitor, respectively. Actinomycin D was used at a concentration of 0.25 µg/ml and camptothecin was used at a concentration of 20, 40, or 50 µM.

Antisense Oligonucleotides

A set of three antisense oligonucleotides targeted against human eIF5A1 were designed by, and purchased from, Molecula Research Labs. The sequence of the first antisense oligonucleotide targeted against human apoptosis-specific eIF5A1 was 5'CCT GTC TCG AAG TCC AAG TC 3' (SEQ ID NO:25). The sequence of the second antisense oligonucleotide targeted against human apoptosis-specific eIF5A1 was 5' GGA CCT TGG CGT GGC CGT GC 3' (SEQ ID NO:26). The sequence of the third antisense oligonucleotide targeted against human apoptosis-specific eIF5A1 was 5'CTC GTA CCT CCC CGC TGT CC 3' (SEQ ID NO:27). The control oligonucleotide had the sequence 5'CGT ACC GGT ACG GTT CCA GG 3' (SEQ ID NO:34). A fluorescein isothiocyanate (FITC)-labelled antisense oligonucleotide (Molecula Research Labs) was used to monitor transfection efficiency and had the sequence 5' GGA CCT TGG CGT GGC CGT GCX 3' (SEQ ID NO:35) where X is the FITC label. All antisense oligonucleotides were fully phosphorothioated.

Transfection of Antisense Oligonucleotides

The ability of the eIF5A1 antisense oligonucleotides to block eIF5A1 protein expression was tested in RKO cells. RKO cells were transfected with antisense oligonucleotides using the transfection reagent, Oligofectamine (Invitrogen). Twenty four hours prior to transfection, the cells were split onto a 24 well plate at 157,000 per well in MEM media supplemented with 10% FBS but lacking penicillin/streptomycin. Twenty four hours later the cells had generally reached a confluency of approximately 50%. RKO cells were either mock transfected, or transfected with 100 nM or 200 nM of antisense oligonucleotide. Transfection medium sufficient for one well of an 24 well plate was prepared by diluting 0, 1.25, or 2.5 µl of a 20 µM stock of antisense oligonucleotide with serum-free MEM to a final volume of 42.5 µl and incubating the mixture at room temperature for 15 minutes. 1.5 µl of Oligofectamine was diluted in 6 µl of serum-free MEM and incubated for 7.5 minutes at room temperature. After 5 minutes the diluted Oligofectamine mixture was added to the DNA mixture and incubated together at room temperature for 20 minutes. The cells were washed once with serum-free MEM before adding 200 µl of MEM to the cells and overlaying 50 µl of transfection medium. The cells were placed back in the growth chamber for 4 hours. After the incubation, 125 µl of MEM+30% FBS was added to the cells. The cells were then cultured for a further 48 hours, treated with 0.25 µg/ml Actinomycin D for 24 hours, and then cell extract was harvested for Western blot analysis.

Transfection of lamina cribosa cells was also tested using 100 and 200 nM antisense oligonucleotide and Oligofectamine using the same procedure described for RKO cells. However, effective transfection of lamina cribosa cells was achieved by simply adding antisense oligonucleotide, diluted from 1 µM to 10 µM in serum-free media, to the cells for 24 hours and thereafter replacing the media with fresh antisense oligonucleotides diluted in serum-containing media every 24 hours for a total of two to five days.

The efficiency of antisense oligonucleotide transfection was optimized and monitored by performing transfections with an FITC-labelled antisense oligonucleotide having the same sequence as eIF5A1 antisense oligonucleotide SEQ ID NO:26 but conjugated to FITC at the 3' end. RKO and lamina cribosa cells were transfected with the FITC-labelled antisense oligonucleotide on an 8-well culture slide. Forty-eight hours later the cells were washed with PBS and fixed for 10 minutes in 3.7% formaldehyde in PBS. The wells were removed and mounting media (Vectashield) was added, followed by a coverslip. The cells were then visualized under UV light on a fluorescent microscope nucleus using a fluorescein filter (Green H546, filter set 48915) and cells fluorescing bright green were determined to have taken up the oligonucleotide.

Detection of Apoptosis

Following transfection of lamina cribosa cells with antisense oligonucleotides and induction of apoptosis with camptothecin, the percentage of cells undergoing apoptosis in cells treated with either control antisense oligonucleotide or antisense oligonucleotide eIF5A1 SEQ ID NO:26 was determined. Two methods were used to detect apoptotic lamina cribosa cells—Hoescht staining and DeadEnd™ Fluorometric TUNEL. The nuclear stain, Hoescht, was used to label the nuclei of lamina cribosa cells in order to identify apoptotic cells based on morphological features such as nuclear fragmentation and condensation. A fixative, consisting of a 3:1 mixture of absolute methanol and glacial acetic acid, was prepared immediately before use. An equal volume of fixative was added to the media of cells growing on a culture slide and incubated for 2 minutes. The media/ fixative mixture was removed from the cells and discarded and 1 ml of fixative was added to the cells. After 5 minutes the fixative was discarded and 1 ml of fresh fixative was added to the cells and incubated for 5 minutes. The fixative was discarded and the cells were air-dried for 4 minutes before adding 1 ml of Hoescht stain (0.5 µg/ml Hoescht 33258 in PBS). After a 10 minute incubation in the dark, the staining solution was discarded, the chambers separating the wells of the culture slide were removed, and the slide was washed 3 times for 1 minute with deionized water. After washing, a few drops of McIlvaine's buffer (0.021 M citric acid, 0.058 M $Na_2HPO_4 \cdot 7H_2O$; pH 5.6) was added to the cells and overlaid with a coverslip. The stained cells were viewed under a fluorescent microscope using a UV filter. Cells with brightly stained or fragmented nuclei were scored as apoptotic. A minimum of 200 cells were counted per well.

The DeadEnd™ Fluorometric TUNEL (Promega) was used to detect the DNA fragmentation that is a characteristic feature of apoptotic cells. Following Hoescht staining, the culture slide was washed briefly with distilled water, and further washed by immersing the slide twice for 5 minutes in PBS (137 mM NaCl, 2.68 mM KCl, 1.47 mM $KH_2PO_4$, 8.1 mM $Na_2HPO_4$), blotting the slide on paper towel between washes. The cells were permeabilized by immersing them in 0.2% Triton X-100 in PBS for 5 minutes. The cells were then washed again by immersing the slide twice for 5 minutes in PBS and blotting the slide on paper towel between washes. 25 µl of equilibration buffer [200 mM potassium cacodylate (pH 6.6), 25 mM Tris-HCl (pH 6.6), 0.2 mM dithiothreitol, 0.25 mg/ml bovine serum albumin, and 2.5 mM cobalt chloride] was added per well and incubated for 5 to 10 minutes. During equilibration, 30 µl of reaction mixture was prepared for each well by mixing in a ratio of 45:5:1, respectively, equilibration buffer, nucleotide mix [50 µM fluorescein-12-dUTP, 100 µM dATP, 10 mM Tris-HCl (pH 7.6), and 1 mM EDTA], and terminal deoxynucleotidyl transferase enzyme (Tdt, 25 U/µl). After the incubation in equilibration buffer, 30 µl of reaction mixture was added per well and overlayed with a coverslip. The reaction was allowed to proceed in the dark at 37° C. for 1 hour. The reaction was terminated by immersing the slide in 2×SSC [0.3 M NaCl, and 30 mM sodium citrate (pH 7.0)] and incubating for 15 minutes. The slide was then washed by immersion in PBS three times for 5 minutes. The PBS was removed by sponging around the wells with a Kim wipe, a drop of mounting media (Oncogene research project, JA1750-4 mL) was added to each well, and the slide was overlayed with a coverslip. The cells were viewed under a fluorescent microscope using a UV filter (UV-G 365, filter set 487902) in order to count the Hoescht-stained nuclei. Any cells with brightly stained or fragmented nuclei were scored as apoptotic. Using the same field of view, the cells were then viewed using a fluorescein filter (Green H546, filter set 48915) and any nuclei fluorescing bright green were scored as apoptotic. The percentage of apoptotic cells in the field of view was calculated by dividing the number of bright green nuclei counted using the fluorescein filter by the total number of nuclei counted under the UV filter. A minimum of 200 cells were counted per well.

FIGS. 54-57 depict the results of these studies. The percentage of apoptotic cells in samples having been transfected with apoptosis-specific eIF5A1 is clearly much less than seen in cells having been transfected with the control oligonucleotide.

Protein Extraction and Western Blotting

Protein from transfected RKO cells was harvested for Western blot analysis by washing the cells with PBS, adding 40 µl of hot lysis buffer [0.5% SDS, 1 mM dithiothreitol, 50 mM Tris-HCl (pH 8.0)] per well. The cells were scraped and the resulting extract was transferred to a microfuge tube, boiled for 5 minutes, and stored at −20° C. The protein was quantitated using the Bio-Rad Protein Assay (Bio-Rad) according to the manufacturer's instructions.

For Western blotting 5 µg of total protein was separated on a 12% SDS-polyacrylamide gel. The separated proteins were transferred to a polyvinylidene difluoride membrane. The membrane was then incubated for one hour in blocking solution (5% skim milk powder in PBS) and washed three times for 15 minutes in 0.05% Tween-20/PBS. The membrane was stored overnight in PBS-T at 4° C. After being warmed to room temperature the next day, the membrane was blocked for 30 seconds in 1 µg/ml polyvinyl alcohol. The membrane was rinsed 5 times in deionized water and then blocked for 30 minutes in a solution of 5% milk in 0.025% Tween-20/PBS. The primary antibody was preincubated for 30 minutes in a solution of 5% milk in 0.025% Tween-20/PBS prior to incubation with the membrane.

Several primary antibodies were used. A monoclonal antibody from Oncogene which recognizes p53 (Ab-6) and a polyclonal antibody directed against a synthetic peptide (amino-CRLPEGDLGKEIEQKYD-carboxy) (SEQ ID NO:33) homologous to the c-terminal end of human eIF5A1 that was raised in chickens (Gallus Immunotech). An anti-β-actin antibody (Oncogene) was also used to demonstrate equal loading of protein. The monoclonal antibody to p53 was used at a dilution of 0.05 µg/ml, the antibody against eIF5A1 was used at a dilution of 1:1000, and the antibody against actin was used at a dilution of 1:20,000. After incubation with primary antibody for 60 to 90 minutes, the membrane was washed 3 times for 15 minutes in 0.05% Tween-20/PBS. Secondary antibody was then diluted in 1% milk in 0.025% Tween-20/PBS and incubated with the membrane for 60 to 90 minutes. When p53 (Ab-6) was used as the primary antibody, the secondary antibody used was a rabbit anti-mouse IgG conjugated to peroxidase (Sigma) at a dilution of 1:5000. When anti-eIF5A1 was used as the primary antibody, a rabbit anti-chicken IgY conjugated to peroxidase (Gallus Immunotech) was used at a dilution of 1:5000. The secondary antibody used with actin was a goat anti-mouse IgM conjugated to peroxidase (Calbiochem) used at a dilution of 1:5000. After incubation with the secondary antibody, the membrane was washed 3 times in PBS-T.

The ECL Plus Western blotting detection kit (Amersham Pharmacia Biotech) was used to detect peroxidase-conjugated bound antibodies. In brief, the membrane was lightly blotted dry and then incubated in the dark with a 40:1 mix of reagent A and reagent B for 5 minutes. The membrane was blotted dry, placed between sheets of acetate, and exposed to X-ray film for time periods varying from 10 seconds to 30 minutes. The membrane was stripped by submerging the membrane in stripping buffer [100 mM 2-Mercaptoethanol, 2% SDS, and 62.5 mM Tris-HCl (pH 6.7)], and incubating at 50° C. for 30 minutes. The membrane was then rinsed in deionized water and washed twice for 10 minutes in large volumes of 0.05% Tween-20/PBS. Membranes were stripped and re-blotted up to three times.

We claim:

1. A method for inhibiting expression of human eIF5A1 set forth in SEQ ID NO: 47 in retinal ganglion cells, the method comprising administering to the retinal ganglion cells an antisense oligonucleotide targeted against the human eIF5A1, wherein the antisense oligonucleotide is selected from the group consisting of SEQ ID NOs: 41, 42 or 43, and wherein the antisense oligonucleotide is homologous to a polynucleotide encoding human eIF-5A1 set forth in SEQ ID NO: 45, wherein the antisense oligonucleotide inhibits expression of eIF5A1 in the cells.

2. The method of claim 1 wherein the antisense oligonucleotide is SEQ ID NO:42.

3. A method of inhibiting expression of human eIF5A1 set forth in SEQ ID NO: 47 in lamina cribosa cells, the method comprising administering to the lamina cribosa cells an antisense oligonucleotide targeted against human eIF5A1, wherein the antisense oligonucleotide is selected from the group consisting of SEQ ID NOs: 41, 42 or 43, and wherein the antisense oligonucleotide is homologous to a polynucleotide encoding human eIF-5A1 set forth in SEQ ID NO: 45 wherein the antisense oligonucleotide inhibits expression of eIF5A1 in the cells.

4. The method of claim 3 wherein the antisense oligonucleotide is SEQ ID NO:42.

5. A method of inhibiting expression of human eIF5A1 set forth in SEQ ID NO: 47 in astrocyte cells, the method comprising administering to the astrocyte cells an antisense oligonucleotide targeted against human eIF5A1, wherein the antisense oligonucleotide is selected from the group consisting of SEQ ID NOs: 41, 42 or 43, and wherein the antisense oligonucleotide is homologous to a polynucleotide encoding human eIF-5A1 set forth in SEQ ID NO: 45 wherein the antisense oligonucleotide inhibits expression of apoptosis-specific eIF5A1 in the cells.

6. The method of claim 5 wherein the antisense oligonucleotide comprises SEQ ID NO:42.

7. The method of claim 3 wherein the inhibiting expression of human eIF-5A1 reduces apoptosis in the lamina cribrosa cells.

* * * * *